United States Patent
Shiono et al.

(10) Patent No.: US 7,604,920 B2
(45) Date of Patent: Oct. 20, 2009

(54) POSITIVE RESIST COMPOSITION, METHOD OF FORMING RESIST PATTERN, POLYMERIC COMPOUND, AND COMPOUND

(75) Inventors: Daiju Shiono, Kawasaki (JP); Takahiro Dazai, Kawasaki (JP); Hiroaki Shimizu, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 0 days.

(21) Appl. No.: 12/186,233

(22) Filed: Aug. 5, 2008

(65) Prior Publication Data

US 2009/0042131 A1 Feb. 12, 2009

(30) Foreign Application Priority Data

Aug. 7, 2007 (JP) ............................. 2007-205500
Jan. 10, 2008 (JP) ............................. 2008-003339

(51) Int. Cl.
G03F 7/004 (2006.01)
G03F 7/30 (2006.01)
C08F 10/00 (2006.01)

(52) U.S. Cl. .............. 430/270.1; 430/326; 430/905; 430/910; 526/280; 526/281; 526/284

(58) Field of Classification Search .......... 430/270.1, 430/326, 905, 910; 526/280, 281, 284
See application file for complete search history.

(56) References Cited

U.S. PATENT DOCUMENTS

| | | | |
|---|---|---|---|
| 5,945,517 | A | 8/1999 | Nitta et al. |
| 6,153,733 | A | 11/2000 | Yukawa et al. |
| 6,423,467 | B1 * | 7/2002 | Kawauchi et al. ......... 430/270.1 |
| 7,179,579 | B2 * | 2/2007 | Uenishi ................. 430/270.1 |
| 7,323,287 | B2 | 1/2008 | Iwai et al. |
| 2005/0233242 | A1 * | 10/2005 | Yamanaka ............. 430/270.1 |
| 2007/0269741 | A1 * | 11/2007 | Iijima et al. ............. 430/270.1 |
| 2009/0061356 | A1 * | 3/2009 | Dazai et al. ............. 430/285.1 |

FOREIGN PATENT DOCUMENTS

| | | |
|---|---|---|
| JP | H09-208554 | 8/1997 |
| JP | H11-035551 | 2/1999 |
| JP | H11-035552 | 2/1999 |
| JP | H11-035573 | 2/1999 |
| JP | H11-322707 | 11/1999 |
| JP | 2003-241385 | 8/2003 |
| WO | WO 2004/074242 A2 | 9/2004 |

* cited by examiner

*Primary Examiner*—John S Chu
(74) *Attorney, Agent, or Firm*—Knobbe, Martens, Olson & Bear, LLP

(57) ABSTRACT

A compound represented by general formula (I) shown below; and a polymeric compound having a structural unit (a0) represented by general formula (a0-1) shown below:

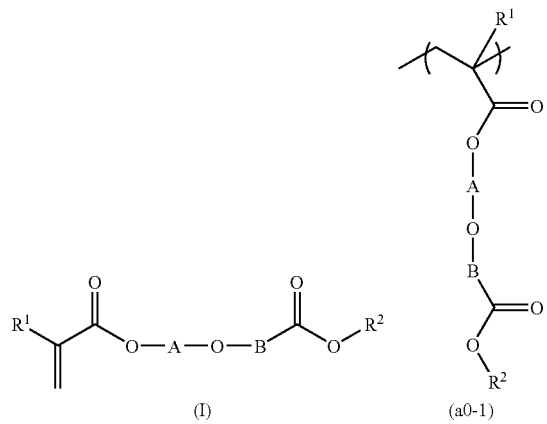

wherein $R^1$ represents a hydrogen atom, a lower alkyl group or a halogenated lower alkyl group; A represents a divalent hydrocarbon group of 2 or more carbon atoms which may have a substituent; B represents a divalent hydrocarbon group of 1 or more carbon atoms which may have a substituent; and $R^2$ represents an acid dissociable, dissolution inhibiting group.

8 Claims, No Drawings

POSITIVE RESIST COMPOSITION, METHOD OF FORMING RESIST PATTERN, POLYMERIC COMPOUND, AND COMPOUND

TECHNICAL FIELD

The present invention relates to a positive resist composition containing a novel polymeric compound, a method of forming a resist pattern using the positive resist composition, the polymeric compound, a compound useful as a monomer for the polymeric compound, a method of producing the compound, and a compound useful as an intermediate in the method.

Priority is claimed on Japanese Patent Application No. 2007-205500, filed Aug. 7, 2007, and Japanese Patent Application No. 2008-003339, filed Jan. 10, 2008, the contents of which are incorporated herein by reference.

BACKGROUND ART

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film.

A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have lead to rapid progress in the field of pattern miniaturization.

Typically, these miniaturization techniques involve shortening the wavelength of the exposure light source. Conventionally, ultraviolet radiation typified by g-line and i-line radiation has been used, but nowadays KrF excimer lasers and ArF excimer lasers are now starting to be introduced in mass production. Furthermore, research is also being conducted into lithography techniques that use exposure light source having a wavelength shorter than these excimer lasers, such as $F_2$ excimer lasers, electron beam, extreme ultraviolet radiation (EUV), and X ray.

Resist materials for use with these types of exposure light sources require lithography properties such as a high resolution capable of reproducing patterns of minute dimensions, and a high level of sensitivity to these types of exposure light sources. As a resist material which satisfies these conditions, a chemically amplified resist composition is used, which includes a base component that exhibits a changed solubility in an alkali developing solution under action of acid and an acid generator that generates acid upon exposure.

For example, a chemically amplified positive resist contains, as a base component (base resin), a resin which exhibits increased solubility in an alkali developing solution under action of acid, and an acid generator is typically used. With respect to a resist film formed by using such a resist composition, when acid is generated from the acid generator at exposed portions, the solubility of the resin component in an alkali developing solution is increased by the action of acid. As a result, the exposed portions become soluble in an alkali developing solution.

Currently, resins that contain structural units derived from (meth)acrylate esters within the main chain (acrylic resins) are now widely used as base resins for resists that use ArF excimer laser lithography, as they exhibit excellent transparency in the vicinity of 193 nm (see, for example, Patent Document 1).

Here, the term "(meth)acrylic acid" is a generic term that includes either or both of acrylic acid having a hydrogen atom bonded to the α-position and methacrylic acid having a methyl group bonded to the α-position. The term "(meth)acrylate ester" is a generic term that includes either or both of the acrylate ester having a hydrogen atom bonded to the α-position and the methacrylate ester having a methyl group bonded to the α-position. The term "(meth)acrylate" is a generic term that includes either or both of the acrylate having a hydrogen atom bonded to the α-position and the methacrylate having a methyl group bonded to the α-position.

[Patent Document 1] Japanese Unexamined Patent Application, First Publication No. 2003-241385

DISCLOSURE OF INVENTION

Means to Solve the Problems

In future, as further progress in lithography techniques, and expansion of the application field for lithography techniques are expected, development of a novel material for use in lithography is strongly desired.

The present invention takes the above circumstances into consideration, with an object of providing a novel polymeric compound which can be used as a base component for a positive resist composition; a compound useful as a monomer for the polymeric compound, and a method of producing the same; a compound useful as an intermediate in the aforementioned method; a positive resist composition containing the polymeric compound; and a method of forming a resist pattern using the positive resist composition.

Means to Solve the Problems

For solving the above-mentioned problems, the present inventors employ the following aspects.

Specifically, a first aspect of the present invention is a positive resist composition including a base component (A) which exhibits increased solubility in an alkali developing solution under action of acid and an acid-generator component (B) which generates acid upon exposure, the base component (A) including a polymeric compound (A1) having a structural unit (a0) represented by general formula (a0-1) shown below.

[Chemical Formula 1]

$$\begin{array}{c} R^1 \\ | \\ -\!\!\!-\!\!\!-\!\!\!CH_2\!\!-\!\!\!C\!\!-\!\!\!-\!\!\!- \\ | \\ C\!\!=\!\!O \\ | \\ O \\ | \\ A \\ | \\ O \\ | \\ B \\ | \\ C\!\!=\!\!O \\ | \\ O \\ | \\ R^2 \end{array}$$

(a0-1)

wherein $R^1$ represents a hydrogen atom, a lower alkyl group or a halogenated lower alkyl group; A represents a divalent hydrocarbon group of 2 or more carbon atoms which may have a substituent; B represents a divalent hydrocarbon group of 1 or more carbon atoms which may have a substituent; and $R^2$ represents an acid dissociable, dissolution inhibiting group.

A second aspect of the present invention is a method of forming a resist pattern, including: applying a positive resist composition of the first aspect to a substrate to form a resist film on the substrate; conducting exposure of the resist film; and alkali-developing the resist film to form a resist pattern.

A third aspect of the present invention is a polymeric compound (hereafter, referred to as "polymeric compound (A1)") having a structural unit (a0) represented by general formula (a0-1) shown below.

[Chemical Formula 2]

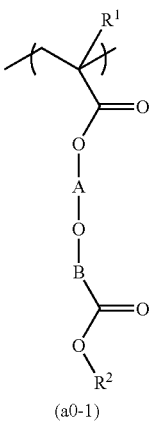

(a0-1)

wherein $R^1$ represents a hydrogen atom, a lower alkyl group or a halogenated lower alkyl group; A represents a divalent hydrocarbon group of 2 or more carbon atoms which may have a substituent; B represents a divalent hydrocarbon group of 1 or more carbon atoms which may have a substituent; and $R^2$ represents an acid dissociable, dissolution inhibiting group.

A fourth aspect of the present invention is a compound represented by general formula (I) shown below (hereafter, referred to as "compound (I)").

[Chemical Formula 3]

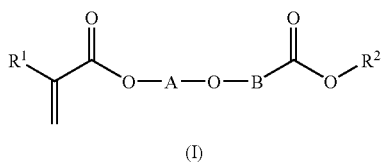

(I)

wherein $R^1$ represents a hydrogen atom, a lower alkyl group or a halogenated lower alkyl group; A represents a divalent hydrocarbon group of 2 or more carbon atoms which may have a substituent; B represents a divalent hydrocarbon group of 1 or more carbon atoms which may have a substituent; and $R^2$ represents an acid dissociable, dissolution inhibiting group.

A fifth aspect of the present invention is a method of producing a compound represented by general formula (I) shown below, including:

reacting a compound represented by general formula (I-1) shown below with a compound represented by general formula (I-2) shown below to obtain a compound represented by general formula (I-3) shown below; and reacting the compound represented by general formula (I-3) shown below with a compound represented by general formula (I-4) shown below, thereby obtaining a compound represented by general formula (I) shown below (hereafter, this method is referred to as "first production method").

[Chemical Formula 4]

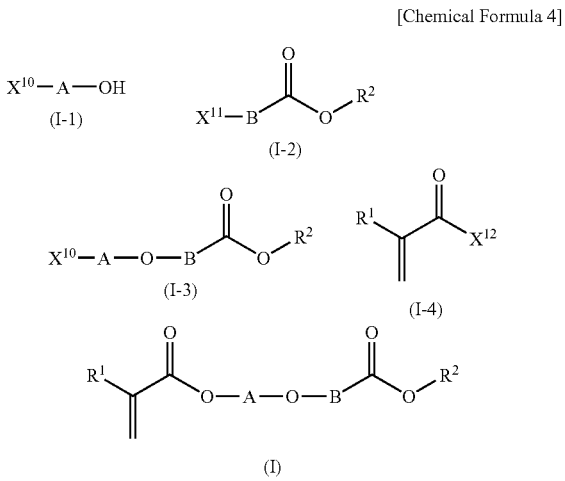

wherein $R^1$ represents a hydrogen atom, a lower alkyl group or a halogenated lower alkyl group; A represents a divalent hydrocarbon group of 2 or more carbon atoms which may have a substituent; B represents a divalent hydrocarbon group of 1 or more carbon atoms which may have a substituent; $R^2$ represents an acid dissociable, dissolution inhibiting group; each of $X^{10}$ and $X^{12}$ independently represents a hydroxyl group or a halogen atom, with the proviso that either one of $X^{10}$ and $X^{12}$ represents a hydroxyl group and the other represents a halogen atom; and $X^{11}$ represents a halogen atom.

A sixth aspect of the present invention is a method of forming a compound represented by general formula (I) shown below, including reacting a compound represented by general formula (I-5) shown below with a compound represented by general formula (I-2) shown below, thereby obtaining a compound represented by general formula (I) shown below (hereafter, this method is referred to as "second production method").

[Chemical Formula 5]

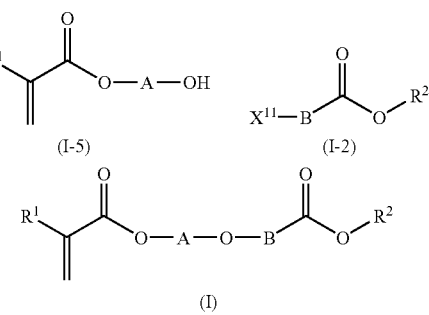

where $R^1$ represents a hydrogen atom, a lower alkyl group or a halogenated lower alkyl group; A represents a divalent hydrocarbon group of 2 or more carbon atoms which may have a substituent; B represents a divalent hydrocarbon group of 1 or more carbon atoms which may have a substituent; $R^2$ represents an acid dissociable, dissolution inhibiting group; and $X^{11}$ represents a halogen atom.

A seventh aspect of the present invention is a compound represented by general formula (II) shown below (hereafter, referred to as "compound (II)").

[Chemical Formula 6]

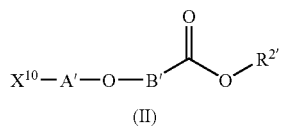

(II)

wherein A' represents a divalent hydrocarbon group of 2 or more carbon atoms which may have a substituent; B' represents a divalent hydrocarbon group of 1 or more carbon atoms which may have a substituent; $R^{2'}$ represents an acid dissociable, dissolution inhibiting group; and $X^{10}$ represents a hydroxyl group or a halogen atom.

In the present description and claims, the term "alkyl group" includes linear, branched or cyclic, monovalent saturated hydrocarbon, unless otherwise specified. Further, the term "alkylene group" includes linear, branched or cyclic divalent saturated hydrocarbon, unless otherwise specified.

A "lower alkyl group" is an alkyl group of 1 to 5 carbon atoms.

A "halogenated lower alkyl group" is a group in which a part or all of the hydrogen atoms of an alkyl group is substituted with halogen atoms. Examples of the halogen atoms include fluorine atoms, chlorine atoms, bromine atoms and iodine atoms.

The term "structural unit" refers to a monomer unit that contributes to the formation of a polymeric compound (polymer or copolymer).

The term "exposure" is used as a general concept that includes irradiation with any form of radiation.

EFFECT OF THE INVENTION

According to the present invention, there are provided a novel polymeric compound which can be used as a base component for a positive resist composition; a compound useful as a monomer for the polymeric compound, and a method of producing the same; a compound useful as an intermediate in the aforementioned method; a positive resist composition containing the polymeric compound; and a method of forming a resist pattern using the positive resist composition.

BEST MODE FOR CARRYING OUT THE INVENTION

First, the compound (I) according to the fourth aspect of the present invention will be described.

The compound (I) is represented by general formula (I) above.

In general formula (I), $R^1$ represents a hydrogen atom, a lower alkyl group or a halogenated lower alkyl group.

The lower alkyl group for $R^1$ is preferably a linear or branched alkyl group of 1 to 5 carbon atoms, and specific examples include a methyl group, ethyl group, propyl group, isopropyl group, n-butyl group, isobutyl group, tert-butyl group, pentyl group, isopentyl group, and neopentyl group.

The halogenated lower alkyl group for $R^1$ is a group in which a part or all of the hydrogen atoms of the aforementioned alkyl group is substituted with halogen atoms. Examples of halogen atoms include fluorine atoms, chlorine atoms, bromine atoms and iodine atoms, and fluorine atoms are particularly desirable.

As $R^1$, a hydrogen atom, a lower alkyl group or a fluorinated lower alkyl group is preferable, and in terms of industrial availability, a hydrogen atom or a methyl group is particularly desirable.

A represents a divalent hydrocarbon group of 2 or more carbon atoms which may have a substituent. When the hydrocarbon group "has a substituent", it means that a part or all of the hydrogen atoms of the hydrocarbon group is substituted with groups or atoms other than hydrogen atom.

The hydrocarbon group may be either an aliphatic hydrocarbon group or an aromatic hydrocarbon group.

In the present description and claims, the term "aliphatic" is a relative concept used in relation to the term "aromatic", and defines a group or compound that has no aromaticity. The term "aliphatic hydrocarbon group" refers to a hydrocarbon group that has no aromaticity.

The aliphatic hydrocarbon group for A may be either saturated or unsaturated, but is preferably saturated.

Specific examples of the aliphatic hydrocarbon group include linear or branched aliphatic hydrocarbon groups, and aliphatic hydrocarbon groups which contain a ring in the structure thereof.

The linear or branched aliphatic hydrocarbon group preferably has 2 to 10 carbon atoms, more preferably 2 to 8, still more preferably 2 to 5, and most preferably 2.

As the linear aliphatic hydrocarbon group, a linear alkylene group is preferable. Specific examples thereof include an ethylene group [—$(CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, a branched alkylene group is preferable. Specific examples include alkylalkylene groups, such as alkylmethylene groups (e.g., —CH($CH_3$)—, —CH($CH_2CH_3$)—, —C($CH_3$)$_2$—, —C($CH_3$)($CH_2CH_3$)—, —C($CH_3$)($CH_2CH_2CH_3$)— and —C($CH_2CH_3$)$_2$—), alkylethylene groups (e.g., —CH($CH_3$)$CH_2$—, —CH($CH_3$)CH($CH_3$)—, —C($CH_3$)$_2CH_2$—, —CH($CH_2CH_3$)$CH_2$— and —CH($CH_2CH_3$)$CH_2$—), alkyltrimethylene groups (e.g., —CH($CH_3$)$CH_2CH_2$— and —CH$_2$CH($CH_3$)$CH_2$—), and alkyltetramethylene groups (e.g., —CH($CH_3$)$CH_2CH_2CH_2$— and —CH$_2$CH($CH_3$)$CH_2CH_2$—). As the alkyl group within the alkylalkylene group, a linear alkyl group of 1 to 5 carbon atoms is preferable.

The linear or branched hydrocarbon group (chain-like hydrocarbon group) may or may not have a substituent. Examples of substituents include a fluorine atom, a fluorinated lower alkyl group of 1 to 5 carbon atoms, and an oxygen atom (═O).

As the hydrocarbon group containing a ring, a cyclic aliphatic hydrocarbon group (a group in which two hydrogen atoms have been removed from an aliphatic hydrocarbon ring), and a group in which the cyclic aliphatic hydrocarbon group is bonded to the terminal of the aforementioned chain-like aliphatic hydrocarbon group or interposed within the aforementioned chain-like aliphatic hydrocarbon group, can be exemplified.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic group, a group in which two hydrogen atoms have been removed from a monocycloalkane of 3 to 6 carbon atoms is preferable. Examples of the monocycloalkane include cyclopentane and cyclohexane.

As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The cyclic aliphatic hydrocarbon group may or may not have a substituent. Examples of substituents include a lower alkyl group of 1 to 5 carbon atoms, a fluorine atom, a fluorinated lower alkyl group of 1 to 5 carbon atoms, and an oxygen atom (=O).

As A, a linear aliphatic hydrocarbon group is preferable, more preferably a linear alkylene group, still more preferably a linear alkylene group of 2 to 5 carbon atoms, and most preferably an ethylene group.

B represents a divalent hydrocarbon group of 1 or more carbon atoms which may have a substituent.

As the hydrocarbon group for B, the same divalent hydrocarbon groups of 2 or more carbon atoms as the hydrocarbon groups for A, and a methylene group which may have a substituent, can be exemplified. As the substituent which a methylene group may have, the same as the substituents which the aforementioned chain-like aliphatic hydrocarbon group may have can be exemplified.

As B, a linear or branched aliphatic hydrocarbon group is preferable, and a methylene group or an alkylmethylene group is particularly desirable.

The alkyl group within the alkyl methylene group is preferably a linear alkyl group of 1 to 5 carbon atoms, more preferably a linear alkyl group of 1 to 3 carbon atoms, and most preferably a methyl group.

$R^2$ represents an acid dissociable, dissolution inhibiting group. When a polymeric compound obtained by using the compound (I) is blended with an acid generator component for a positive resist composition, the acid dissociable, dissolution inhibiting group exhibits an acid dissociability so as to be dissociated by action of acid generated from the acid generator component upon exposure, and an alkali dissolution-inhibiting effect that renders the entire polymeric compound insoluble in an alkali developing solution prior to dissociation.

As the acid dissociable, dissolution inhibiting group for $R^2$, any of those which have been proposed as acid dissociable, dissolution inhibiting groups for a base resin of a chemically amplified resist may be used. Generally, groups that form either a cyclic or chain-like tertiary alkyl ester with the carboxyl group of (meth)acrylic acid, and acetal-type acid dissociable, dissolution inhibiting groups such as alkoxyalkyl groups are widely known. In the present description, the term "(meth)acrylate ester" is a generic term that includes either or both of the acrylate ester having a hydrogen atom bonded to the α-position and the methacrylate ester having a methyl group bonded to the α-position.

Here, a tertiary alkyl ester describes a structure in which an ester is formed by substituting the hydrogen atom of a carboxyl group with a chain-like or cyclic tertiary alkyl group, and a tertiary carbon atom within the chain-like or cyclic tertiary alkyl group is bonded to the oxygen atom at the terminal of the carbonyloxy group (—C(O)—O—). In this tertiary alkyl ester, the action of acid causes cleavage of the bond between the oxygen atom and the tertiary carbon atom.

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid dissociable, dissolution inhibiting groups".

Examples of tertiary alkyl ester-type acid dissociable, dissolution inhibiting groups include aliphatic branched, acid dissociable, dissolution inhibiting groups and aliphatic cyclic group-containing acid dissociable, dissolution inhibiting groups.

The term "aliphatic branched" refers to a branched structure having no aromaticity.

The "aliphatic branched, acid dissociable, dissolution inhibiting group" is not limited to be constituted of only carbon atoms and hydrogen atoms (not limited to hydrocarbon groups), but is preferably a hydrocarbon group.

Further, the "hydrocarbon group" may be either saturated or unsaturated, but is preferably saturated.

As the aliphatic branched, acid dissociable, dissolution inhibiting group, for example, a group represented by the formula —C($R^{71}$)($R^{72}$)($R^{73}$) (wherein each of $R^{71}$ to $R^{73}$ independently represents a linear alkyl group of 1 to 5 carbon atoms) can be exemplified. The group represented by the formula —C($R^{71}$)($R^{72}$)($R^{73}$) preferably has 4 to 8 carbon atoms, and specific examples include a tert-butyl group, a tert-pentyl group and a tert-heptyl group.

The term "aliphatic cyclic group" refers to a monocyclic group or polycyclic group that has no aromaticity.

The "aliphatic cyclic group" may or may not have a substituent. Examples of substituents include lower alkyl groups of 1 to 5 carbon atoms, fluorine atom, fluorinated lower alkyl groups of 1 to 5 carbon atoms, and oxygen atom (=O).

The basic ring of the "aliphatic cyclic group" exclusive of substituents is not limited to be constituted from only carbon and hydrogen (not limited to hydrocarbon groups), but is preferably a hydrocarbon group. Further the "hydrocarbon group" may be either saturated or unsaturated, but is preferably saturated.

The "aliphatic cyclic group" is preferably a polycyclic group.

As such aliphatic cyclic groups, groups in which one or more hydrogen atoms have been removed from a monocycloalkane or a polycycloalkane such as a bicycloalkane, tricycloalkane or tetracycloalkane which may or may not be substituted with a lower alkyl group, a fluorine atom or a fluorinated lower alkyl group, may be exemplified. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, dicyclodecane, tricyclodecane or tetracyclododecane.

Examples of acid dissociable, dissolution inhibiting groups containing an aliphatic cyclic group include (i) a group which has a tertiary carbon atom on the ring structure of a monovalent aliphatic cyclic group; and (ii) a group which has a branched alkylene group containing a tertiary carbon atom, and a monovalent aliphatic cyclic group to which the tertiary carbon atom is bonded.

Specific examples of (i) a group which has a tertiary carbon atom on the ring structure of a monovalent aliphatic cyclic group include groups represented by general formulas (1-1) to (1-9) shown below.

Specific examples of (ii) a group which has a branched alkylene group containing a tertiary carbon atom, and a monovalent aliphatic cyclic group to which the tertiary carbon atom is bonded include groups represented by general formulas (2-1) to (2-6) shown below.

[Chemical Formula 7]

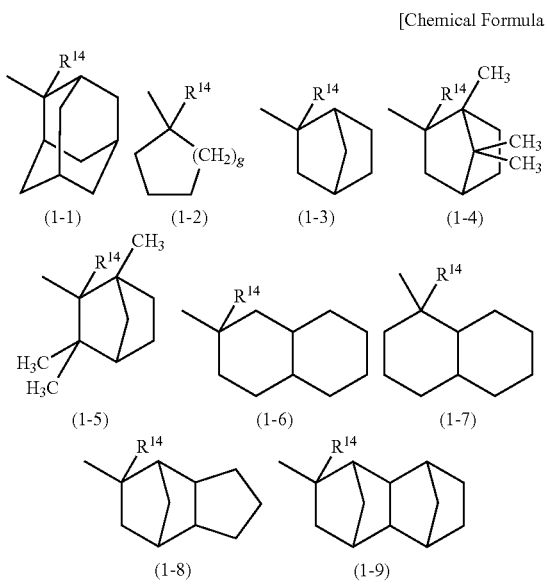

wherein $R^{14}$ represents a lower alkyl group; and g represents an integer of 0 to 8.

[Chemical Formula 8]

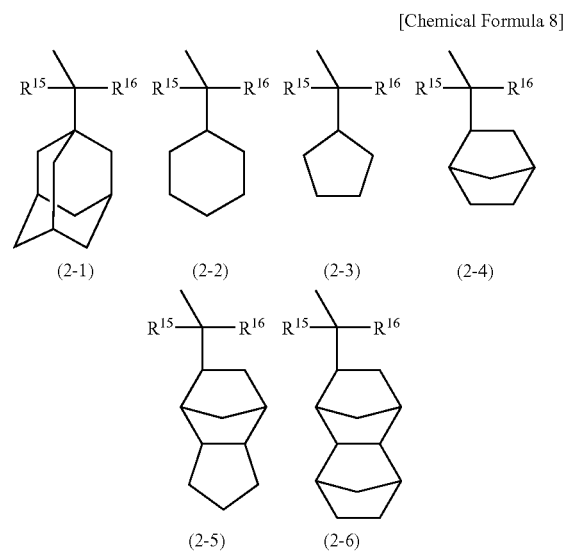

wherein each of $R^{15}$ and $R^{16}$ independently represents an alkyl group.

As the alkyl group for $R^{14}$ to $R^{16}$, a lower alkyl group is preferable, and a linear or branched alkyl group is more preferable. Specific examples include a methyl group, ethyl group, propyl group, isopropyl group, n-butyl group, isobutyl group, tert-butyl group, pentyl group, isopentyl group, a neopentyl group. Among these, a methyl group, ethyl group or n-butyl group is preferable, and a methyl group or ethyl group is more preferable.

g is preferably an integer of 0 to 3, more preferably 1 to 3, and still more preferably 1 or 2.

An "acetal-type acid dissociable, dissolution inhibiting group" generally substitutes a hydrogen atom at the terminal of an alkali-soluble group such as a carboxy group or hydroxyl group, so as to be bonded with an oxygen atom. When acid is generated upon exposure, the generated acid acts to break the bond between the acetal-type acid dissociable, dissolution inhibiting group and the oxygen atom to which the acetal-type, acid dissociable, dissolution inhibiting group is bonded.

Examples of acetal-type acid dissociable, dissolution inhibiting groups include groups represented by general formula (p1) shown below.

[Chemical Formula 9]

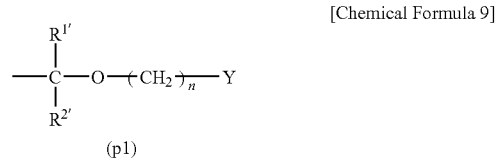

wherein each of $R^{1\prime}$ and $R^{2\prime}$ independently represents a hydrogen atom or a lower alkyl group; n represents an integer of 0 to 3; and Y represents a lower alkyl group or an aliphatic cyclic group.

In general formula (p1) above, n is preferably an integer of 0 to 2, more preferably 0 or 1, and most preferably 0.

As the lower alkyl group for $R^{1\prime}$ and $R^{2\prime}$, the same as the lower alkyl groups for R above can be exemplified. As the lower alkyl group for $R^{1\prime}$ and $R^{2\prime}$, a methyl group or ethyl group is preferable, and a methyl group is particularly desirable.

In the present invention, it is preferable that at least one of $R^{1\prime}$ and $R^{2\prime}$ be a hydrogen atom. That is, it is preferable that the acid dissociable, dissolution inhibiting group (p1) is a group represented by general formula (p1-1) shown below.

[Chemical Formula 10]

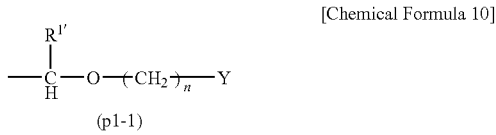

wherein $R^{1\prime}$, n and Y are as defined above.

As the lower alkyl group for Y, the same as the lower alkyl groups for R above can be exemplified.

As the aliphatic cyclic group for Y, any of the aliphatic monocyclic/polycyclic groups which have been proposed for conventional ArF resists and the like can be appropriately selected for use. For example, the same groups described above in connection with the "aliphatic cyclic group" can be exemplified.

Further, as the acetal-type, acid dissociable, dissolution inhibiting group, groups represented by general formula (p2) shown below can also be exemplified.

[Chemical Formula 11]

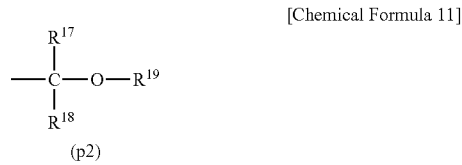

wherein each of $R^{17}$ and $R^{18}$ independently represents a linear or branched alkyl group or a hydrogen atom; and $R^{19}$ represents a linear, branched or cyclic alkyl group; or each of $R^{17}$ and $R^{19}$ independently represents a linear or branched alkylene group, wherein the terminal of $R^{17}$ is bonded to the terminal of $R^{19}$ to form a ring.

The alkyl group for $R^{17}$ and $R^{18}$ preferably has 1 to 15 carbon atoms, and may be either linear or branched. As the alkyl group, an ethyl group or a methyl group is preferable, and a methyl group is most preferable.

It is particularly desirable that either one of $R^{17}$ and $R^{18}$ be a hydrogen atom, and the other be a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cycloalkyl group, it preferably has 4 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be exemplified. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane. Of these, a group in which one or more hydrogen atoms have been removed from adamantane is preferable.

In general formula (p2) above, each of $R^{17}$ and $R^{19}$ may independently represent a linear or branched alkylene group (preferably an alkylene group of 1 to 5 carbon atoms), and the terminal of $R^{19}$ may be bonded to the terminal of $R^{17}$.

In such a case, a cyclic group is formed by $R^{17}$, $R^{19}$, the oxygen atom having $R^{19}$ bonded thereto and the carbon atom having the oxygen atom and $R^{17}$ bonded thereto. Such a cyclic group is preferably a 4 to 7-membered ring, and more preferably a 4 to 6-membered ring. Specific examples of the cyclic group include tetrahydropyranyl group and tetrahydrofuranyl group.

Specific examples of acetal-type acid dissociable, dissolution inhibiting groups include groups represented by formulas (3-1) to (3-12) shown below.

[Chemical Formula 12]

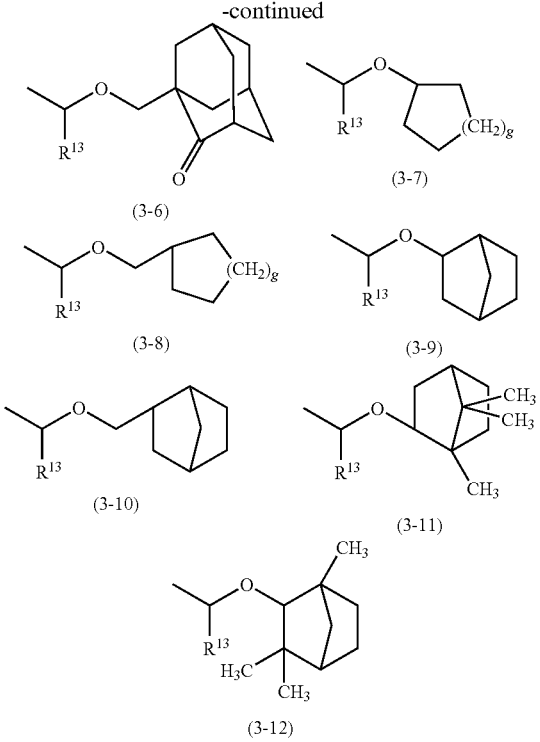

wherein $R^{13}$ represents a hydrogen atom or a methyl group; and g is as defined above.

In the present invention, $R^2$ is preferably a tertiary alkyl ester-type acid dissociable, dissolution inhibiting group, more preferably the aforementioned group (i) which has a tertiary carbon atom on the ring structure of a monovalent aliphatic cyclic group. Among the aforementioned groups (i), a group represented by general formula (1-1) above is preferable.

As the compound (I), a compound represented by general formula (I') or (II') shown below is preferable, and a compound represented by general formula (I') shown below is particularly desirable.

[Chemical Formula 13]

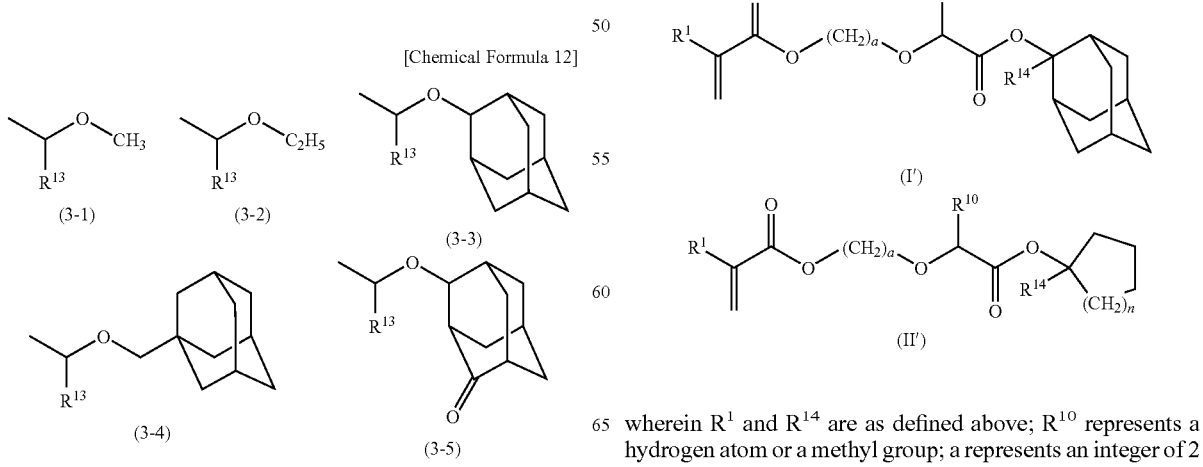

wherein $R^1$ and $R^{14}$ are as defined above; $R^{10}$ represents a hydrogen atom or a methyl group; a represents an integer of 2 to 10; and n represents an integer of 0 to 3.

a is preferably an integer of 2 to 5, and most preferably 2.

The method for producing the compound (I) is not particularly limited, and the compound (I) can be produced by the first production method or second production method described below.

The compound (I) of the present invention is a novel compound which is conventionally unknown.

The compound (I) can be preferably used for producing a polymeric compound usable as a base component of a positive resist composition. That is, the compound (I) is a polymeric compound, and can be used as a monomer for a polymeric compound (polymer or copolymer).

By using the compound (I) as a monomer, the polymeric compound (A1) of the present invention having a structural unit (a0) represented by general formula (a0-1) above can be produced.

<<First Production Method>>

Next the first production method (the method according to the fifth aspect of the present invention) will be described.

The first production method includes reacting a compound represented by general formula (I-1) above (hereafter, referred to as "compound (I-1)") with a compound represented by general formula (I-2) above hereafter, referred to as "compound (I-2)") to obtain a compound represented by general formula (I-3) above (hereafter, referred to as "compound (I-3)") (hereafter, this step is referred to as "step 1"); and reacting the compound (I-3) with a compound represented by general formula (I-4) above (hereafter, referred to as "compound (I-4)"), thereby obtaining a compound (I) (hereafter, this step is referred to as the "step 2").

In general formulas (I-1) to (I-4), $R^1$, A, B and $R^2$ are respectively as defined for $R^1$, A, B and $R^2$ in general formula (I) above.

Each of $X^{10}$ and $X^{12}$ independently represents a hydroxyl group or a halogen atom, with the proviso that either one of $X^{10}$ and $X^{12}$ represents a hydroxyl group and the other represents a halogen atom; and $X^{11}$ represents a halogen atom. Examples of the halogen atom include a bromine atom, a chlorine atom, an iodine atom and a fluorine atom.

As the halogen atom for $X^{10}$ and $X^{12}$, in terms of reactivity, a bromine atom or chlorine atom is preferable.

As $X^{11}$, in terms of reactivity, a bromine atom or chlorine atom is preferable, and a bromine atom is particularly desirable.

"Step 1"

The compound (I-1) can be reacted with the compound (I-2) by a conventional method. For example, the compound (I-1) can be contacted with the compound (I-2) in a reaction solvent in the presence of a base. Such a method can be conducted by adding the compound (I-2) to a solution obtained by dissolving the compound (I-1) in a reaction solvent, in the presence of a base.

As the compound (I-1) and the compound (I-2), commercially available compounds may be used. Alternatively, the compound (I-1) and the compound (I-2) may be synthesized.

When $X^{10}$ is a hydroxyl group, the compound (I-1) is a divalent alcohol, and when $X^{10}$ is a halogen atom, the compound (I-1) is a halogenated alcohol. The compound (I-1) is not particularly limited as long as it is a divalent alcohol or a halogenated alcohol. Specific examples of the divalent alcohol include ethylene glycol, propylene glycol, 1,4-butanediol and 1,5-pentanediol. Specific examples of the halogenated alcohol include 2-bromo-1-ethanol, 3-chloro-1-propanol, 4-chloro-1-butanol, and 5-chloro-1-pentanol.

Examples of the compound (I-2) include 2-methyl-2-adamantyloxycarbonylmethylchloride, 2-ethyl-2-adamantyloxycarbonylmethylchloride, 1-methyl-1-cyclohexyloxycarbonylmethylchloride, 1-ethyl-1-cyclohexyloxycarbonylmethylchloride, 1-methyl-1-cyclopentyloxycarbonylmethylchloride and 1-ethyl-1-cyclopentyloxycarbonylmethylchloride.

As the reaction solvent, any reaction solvent capable of dissolving the compounds (I-1) and (I-2) as raw materials can be used, and specific examples include tetrahydrofuran (THF), acetone, dimethylformamide (DMF), dimethylacetamide, dimethylsulfoxide (DMSO) and acetonitrile.

Examples of the base include inorganic bases such as sodium hydride and $K_2CO_3$, and organic bases such as triethylamine, 4-dimethylaminopyridine (DMAP) and pyridine.

Especially in step 1, sodium hydride is preferably used.

The amount of the compound (I-2) added is preferably 1 to 100 times the molar amount of the compound (I-1), more preferably 1 to 50 times the molar amount of the compound (I-1).

The reaction temperature is preferably 0 to 50° C., more preferably 5 to 40° C., and most preferably room temperature.

The reaction time varies, depending on the reactivity of the compound (I-1) and the compound (I-2), the reaction temperature, and the like. However, in general, the reaction time is preferably 1 to 24 hours, more preferably 3 to 12 hours.

After the reaction, the reaction liquid can be directly used in the following step, or the compound (I-3) within the reaction liquid may be separated and purified. The separation and purification can be conducted by a conventional method. For example, any one of concentration, solvent extraction, crystallization, recrystallization and chromatography can be used alone, or two or more of these methods may be used in combination.

"Step 2"

The method of reacting the compound (I-3) with the compound (I-4) is not particularly limited. For example, the compound (I-4) can be added to a solution in which the compound (I-3) obtained in the first step is dissolved, in the presence of a base.

As the solution in which the compound (I-3) is dissolved, the reaction liquid obtained in step 1 may be directly used, or the compound (I-3) separated and purified from the reaction liquid may be dissolved in a reaction solvent.

As the reaction solvent any reaction solvent capable of dissolving the compound (I-3) as a raw material can be used, and the same as those exemplified above for the reaction solvent in the step 1 can be mentioned.

As the base, the same as those exemplified above for the base in the step 1 can be mentioned. Especially in the step 2, triethylamine is preferably used.

As the compound (I-4), when a divalent alcohol is used as the compound (I-1), a compound in which $X^{12}$ is a halogen atom is used, and when a halogenated alcohol is used as the compound (I-1), a compound in which $X^{12}$ is a hydroxyl group is used.

The amount of the compound (I-4) added is preferably 1 to 2 times the molar amount of the compound (I-3), more preferably 1 to 1.5 times the molar amount of the compound (I-3).

The reaction temperature is preferably 0 to 50° C., more preferably 5 to 40° C., and most preferably room temperature.

The reaction time varies, depending on the reactivity of the compound (I-3) and the compound (I-4), the reaction temperature, and the like. However, in general, the reaction time is preferably 1 to 24 hours, more preferably 3 to 12 hours.

After the reaction, the compound (I) within the reaction liquid may be separated and purified. The separation and purification can be conducted by a conventional method. For example, any one of concentration, solvent extraction, crystallization, recrystallization and chromatography can be used alone, or two or more of these methods may be used in combination.

The structures of the compounds obtained in the steps above can be confirmed by a general organic analysis method such as $^1$H-nuclear magnetic resonance (NMR) spectrometry, $^{13}$C-NMR spectrometry, $^{19}$F-NMR spectrometry, absorption (IR) spectrometry, mass spectrometry (MS), elementary analysis and X-ray diffraction analysis.

<<Second Production Method>>

Next, the second production method (the method according to the sixth aspect of the present invention) will be described.

The second production method includes reacting a compound represented by general formula (I-5) above (hereafter, referred to as "compound (I-5)") with a compound (I-2), thereby obtaining a compound (I) (hereafter, this step is referred to as the "step 1'").

In general formulas (I-2) and (I-5) above, $R^1$, A, B and $R^2$ are respectively as defined for $R^1$, A, B and $R^2$ in general formula (I) above.

$X^{11}$ is a halogen atom. Examples of the halogen atom include a bromine atom, a chlorine atom, an iodine atom and a fluorine atom.

As $X^{11}$, in a terms of reactivity, a bromine atom or chlorine atom is preferable, and a bromine atom is particularly desirable.

"Step 1'"

The compound (I-5) can be reacted with the compound (I-2) by a conventional method. For example, the compound (I-5) can be contacted with the compound (I-2) in a reaction solvent in the presence of a base. Such a method can be conducted by adding the compound (I-2) to a solution obtained by dissolving the compound (I-5) in a reaction solvent, in the presence of a base.

As the compound (I-5) and the compound (I-2), commercially available compounds may be used. Specific examples of the compound (I-5) include 2-hydroxyethyl(meth)acrylate, 3-hydroxypropyl(meth)acrylate and 4-hydroxybutyl (meth)acrylate.

As the reaction solvent, any reaction solvent capable of dissolving the compound (I-5) and (I-2) as raw materials can be used, and specific examples include tetrahydrofuran (THF), acetone, dimethylformamide (DMF), dimethylacetamide, dimethylsulfoxide (DMSO) and acetonitrile.

Examples of the base include inorganic bases such as sodium hydride, $K_2CO_3$ and $Cs_2CO_3$, and organic bases such as triethylamine, 4-dimethylaminopyridine (DMAP) and pyridine. Especially in step 1', sodium hydride is preferably used.

The amount of the compound (I-2) added is preferably 1 to 2 times the molar amount of the compound (I-5), more preferably 1 to 1.5 times the molar amount of the compound (I-5).

The reaction temperature is preferably 0 to 50° C., more preferably 5 to 40° C., and most preferably room temperature.

The reaction time varies, depending on the reactivity of the compound (I-5) and the compound (I-2), the reaction temperature, and the like. However, in general, the reaction time is preferably 1 to 24 hours, more preferably 3 to 12 hours.

After the reaction, the compound (I) within the reaction liquid may be separated and purified. The separation and purification can be conducted by a conventional method. For example, any one of concentration, solvent extraction, crystallization, recrystallization and chromatography can be used alone, or two or more of these methods may be used in combination.

The structure of the compound obtained in the step above can be confirmed by a general organic analysis method such as $^1$H-NMR spectrometry, $^{13}$C-NMR spectrometry, $^{19}$F-NMR spectrometry, infrared absorption (IR) spectrometry, mass spectrometry (MS), elementary analysis and X-ray diffraction analysis.

<<Compound (II)>>

Next, the compound (II) according to the seventh aspect of the present invention will be described.

The compound (II) is represented by general formula (II) above,

In general formula (II) above, $X^{10}$, A', B' and $R^2$ are respectively as defined for $X^{10}$, A, B and $R^2$ in general formula (I) above.

The compound (II) can be produced in the same manner as the compound (I-3). That is, the compound (II) can be produced by conducting the step 1 of the first production method.

The compound (II) can be used as the compound (I-3) in the first production method.

<<Polymeric Compound (A1)>>

Next, the polymeric compound (A1) according to the third aspect of the present invention will be described.

The polymeric compound (A1) has a structural unit (a0) represented by general formula (a0-1) above.

In general formula (a0-1), $R^1$, A, B and $R^2$ are respectively as defined for $R^1$, A, B and $R^2$ in general formula (I) above.

As the structural unit (a0-1) a structural unit represented by general formula (a0-1-1-) shown below is particularly desirable.

[Chemical Formula 14]

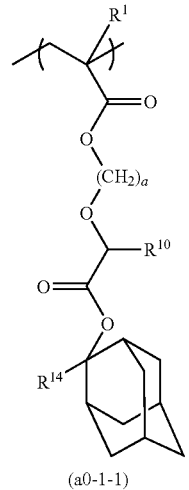

(a0-1-1)

wherein $R^1$, a, $R^{10}$ and $R^{14}$ are respectively as defined for $R^1$, a, $R^{10}$ and $R^{14}$ in general formula (I').

As the structural unit (a0) included in the polymeric compound (A1), one type may be used, or two or more types may be used in combination.

The polymeric compound (A1) may be either a polymer consisting of the structural unit (a0), or a copolymer including a structural unit other than the structural unit (a0).

With respect to the amount of the structural unit (a0) in the polymeric compound (A1), the total amount of the structural unit (a0) and the below-described structural unit (a1) (the amount of the structural unit (a0) when the polymeric compound (A1) has no structural unit (a1)) based on the combined total of all structural units constituting the polymeric compound (A1) is preferably 10 to 80 mol %, more preferably 20 to 70 mol %, and most preferably 25 to 50 mol %. By making the amount of the structural unit (a0) satisfy the lower limit of the above-mentioned range, a pattern can be easily formed using a resist composition prepared from the polymeric compound (A1). On the other hand, by making the amount of the structural unit (a0) satisfy the upper limit of the above-mentioned range, a good balance can be achieved with the other structural units.

Especially, the amount of the structural unit (a0) based on the combined total of all structural units constituting the polymeric compound (A1) is preferably 10 mol % or more, more preferably 20 mol % or more, as various lithography properties (such as resolution and line edge roughness) of a positive resist composition containing the polymeric compound (A1) are improved.

When the polymeric compound (A1) is a copolymer including a structural unit other than the structural unit (a0), the structural unit other than the structural unit (a0) is not particularly limited, and any structural unit conventionally used for a base resin of a chemically amplified resist can be used.

As preferable structural units, structural units derived from an acrylate ester, such as the below-described structural units (a1) to (a3) can be exemplified.

It is preferable that the polymeric compound (A1) have a structural unit (a2), as well as the structural unit (a0).

Further, it is preferable that the polymeric compound (A1) have a structural unit (a3), as well as the structural unit (a0), or the structural units (a0) and (a2).

In the present descriptions and claims, the term "structural unit derived from an acrylate ester" refers to a structural unit which is formed by the cleavage of the ethylenic double bond of an acrylate ester.

The term "acrylate ester" is a generic term that includes acrylate esters having a hydrogen atom bonded to the carbon atom on the α-position, and acrylate esters having a substituent (an atom other than a hydrogen atom or a group) bonded to the carbon atom on the α-position. As the substituent, a lower alkyl group or a halogenated lower alkyl group can be mentioned. With respect to the "structural unit derived from an acrylate ester", the "α-position (the carbon atom on the α-position)" refers to the carbon atom having the carbonyl group bonded thereto, unless specified otherwise.

With respect to the acrylate ester, as the lower alkyl group and halogenated lower alkyl group for the substituent at the α-position, the same as the lower alkyl group and halogenated lower alkyl group for $R^1$ defined above can be exemplified.

It is preferable that a hydrogen atom, a lower alkyl group or a halogenated lower alkyl group is bonded to the α-position of the acrylate ester, more preferably a hydrogen atom, a lower alkyl group or a fluorinated lower alkyl group. In terms of industrial availability, a hydrogen atom or a methyl group is particularly desirable.

<Structural Unit (a2)>

The structural unit (a2) is a structural unit derived from an acrylate ester containing a lactone-containing cyclic group.

The term "lactone-containing cyclic group" refer to a cyclic group including one ring containing a —O—C(O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings.

When the polymeric compound (A1) is used for forming a resist film, the lactone-containing cyclic group of the structural unit (a2) is effective in improving the adhesion between the resist film and the substrate, and increasing the compatibility with the developing solution containing water.

As the structural unit (a2), there is no particular limitation, and an arbitrary structural unit may be used.

Specific examples of lactone-containing monocyclic groups include groups in which one hydrogen atom has been removed from γ-butyrolactone. Further, specific examples of lactone-containing polycyclic groups include groups in which one hydrogen atom has been removed from a lactone ring-containing bicycloalkane, tricycloalkane or tetracycloalkane.

More specifically, examples of the structural unit (a2) include structural units represented by general formulas (a2-1) to (a2-5) shown below.

[Chemical Formula 15]

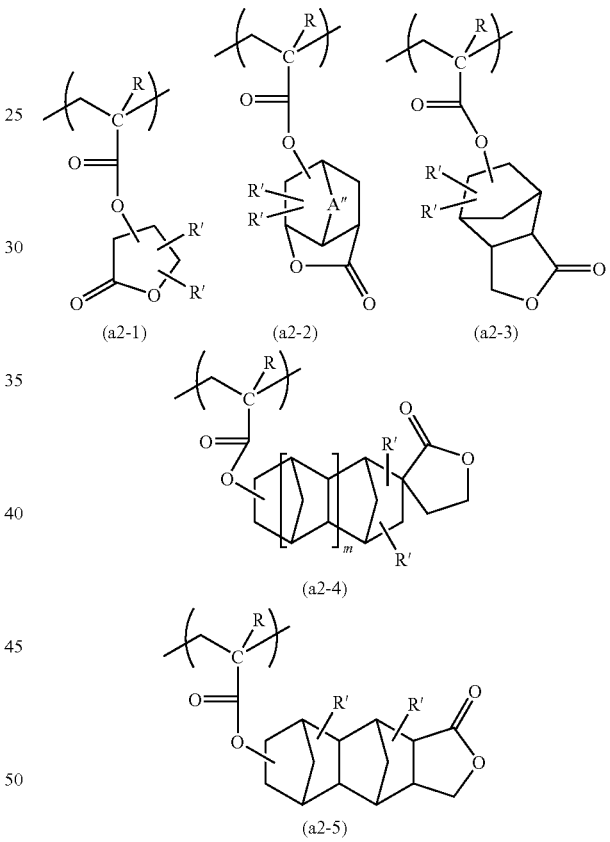

wherein R represents a hydrogen atom, a lower alkyl group or a halogenated lower alkyl group; R' represents a hydrogen atom, a lower alkyl group, an alkoxy group of 1 to 5 carbon atoms or —COOR" (wherein R" represents a hydrogen atom or a linear, branched or cyclic alkyl group of 1 to 15 carbon atoms); m represents 0 or 1; and A" represents an alkylene group of 1 to 5 carbon atoms or an oxygen atom.

In general formulas (a2-1) to (a2-5), R is the same as $R^1$ in the structural unit (a0).

The lower alkyl group for R' is the same as the lower alkyl group for $R^1$ defined above.

When R" is a linear or cyclic alkyl group, it preferably has 1 to 10 carbon atoms, more preferably 1 to 5 carbon atoms.

When R" is a cyclic alkyl group, it preferably has 3 to 15 carbon atoms, more preferably 4 to 12 carbon atoms, and most preferably 5 to 10 carbon atoms. Examples thereof include groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

Specific examples of alkylene groups of 1 to 5 carbon atoms for A" include a methylene group, ethylene group, n-propylene group and isopropylene group.

In the structural units represented by general formulas (a2-1) to (a2-5), in consideration of industrial availability, R' is preferably a hydrogen atom.

In general formula (a2-1), the bonding position of the oxygen atom (—O—) on the γ-butyrolactone ring is not particularly limited, but is preferably the α-position or the β-position.

Specific examples of structural units represented by general formulas (a2-1) to (a2-5) above are shown below.

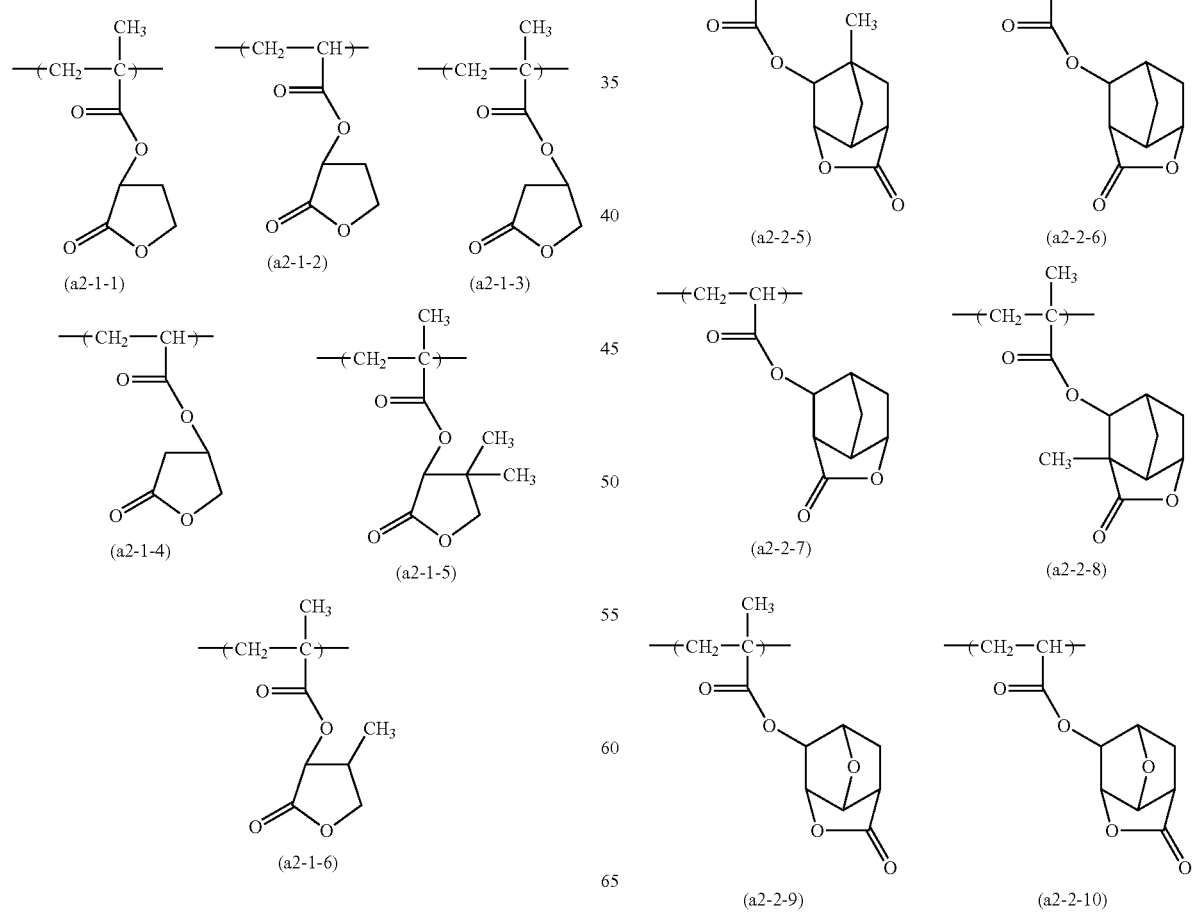

-continued
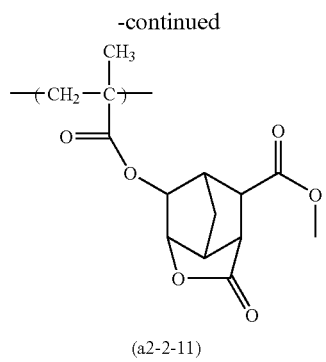
(a2-2-11)
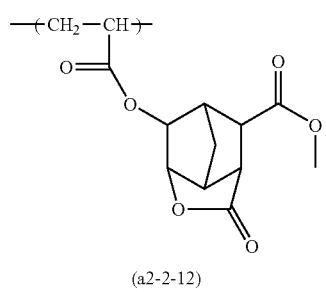
(a2-2-12)
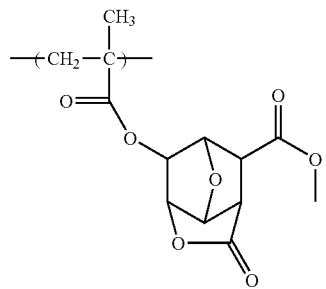
(a2-2-13)
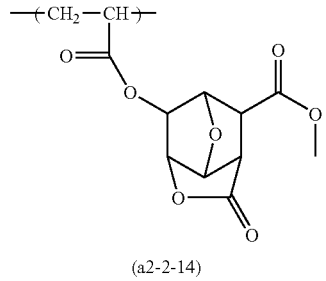
(a2-2-14)
[Chemical Formula 18]
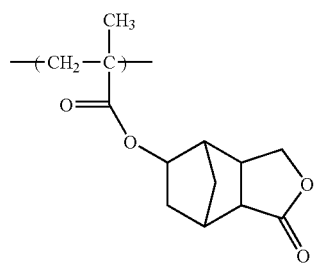
(a2-3-1)
-continued
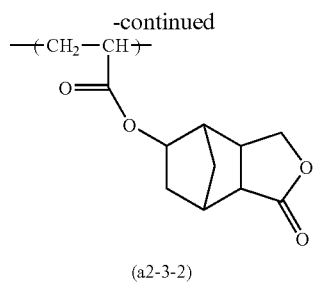
(a2-3-2)
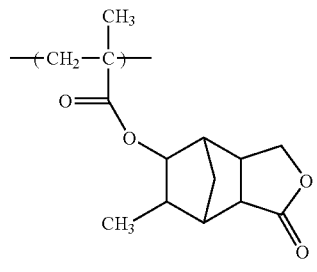
(a2-3-3)
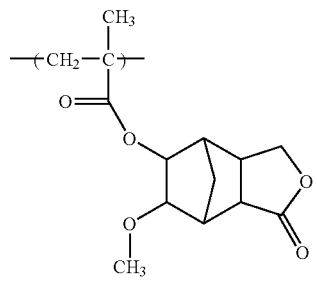
(a2-3-4)
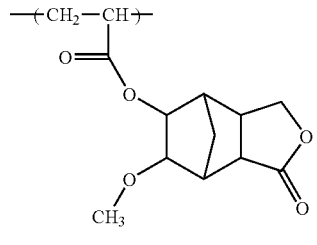
(a2-3-5)
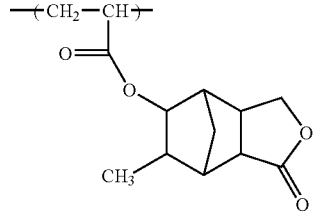
(a2-3-6)
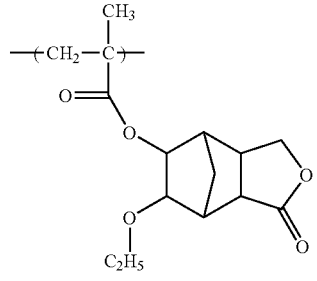
(a2-3-7)

-continued
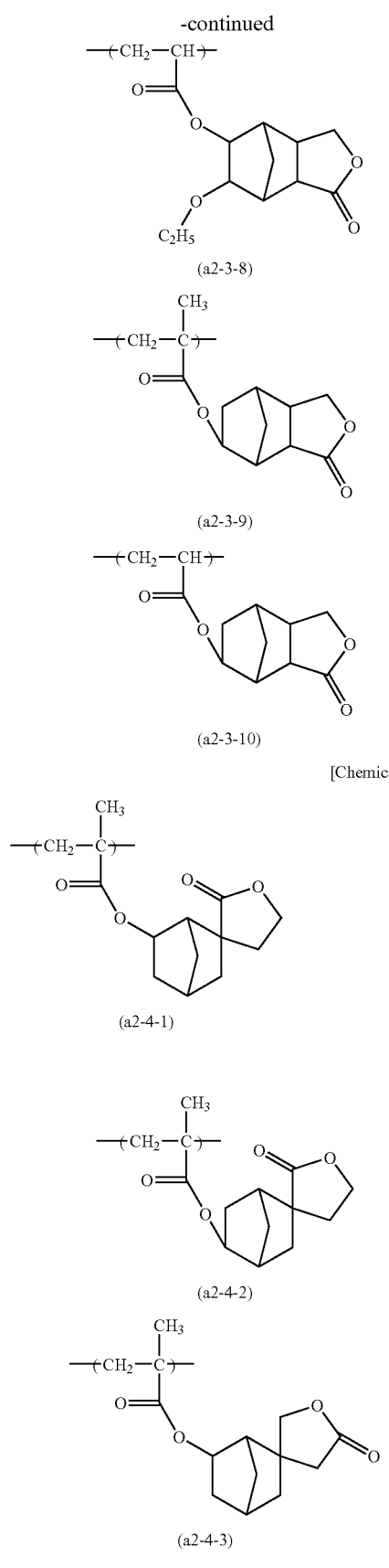
[Chemical Formula 19]
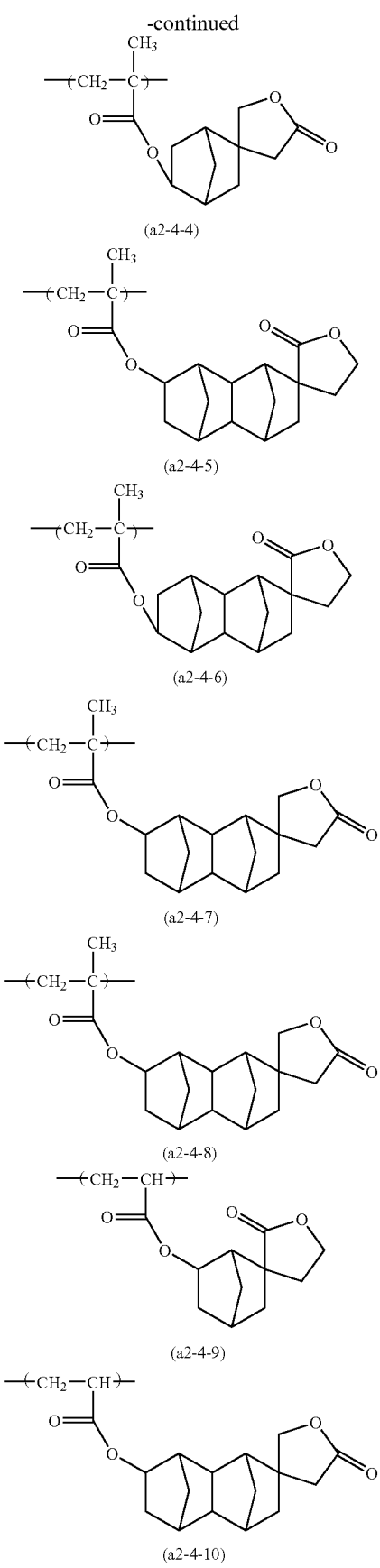

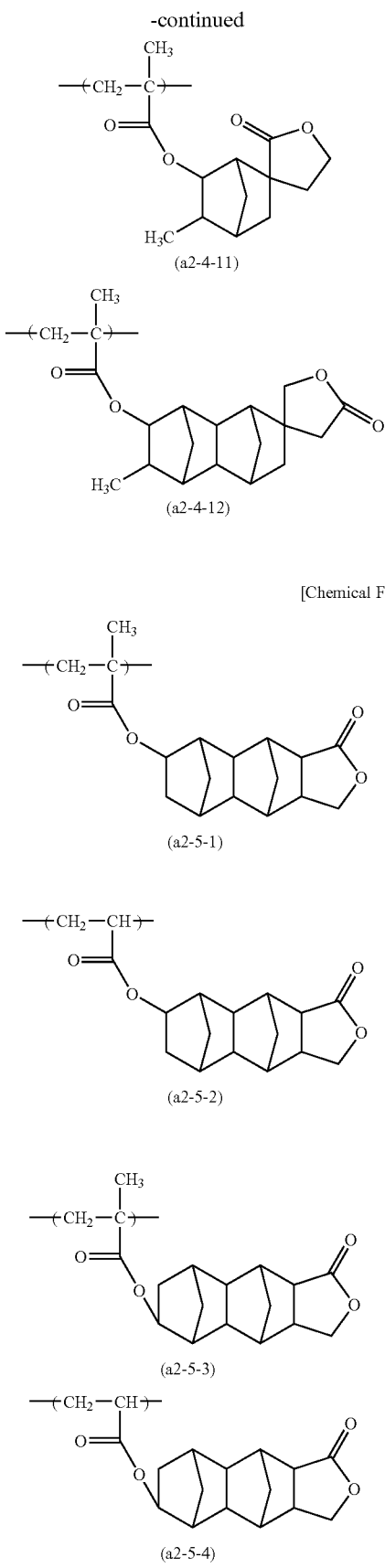

(a2-4-11)
(a2-4-12)

[Chemical Formula 20]

(a2-5-1)
(a2-5-2)
(a2-5-3)
(a2-5-4)

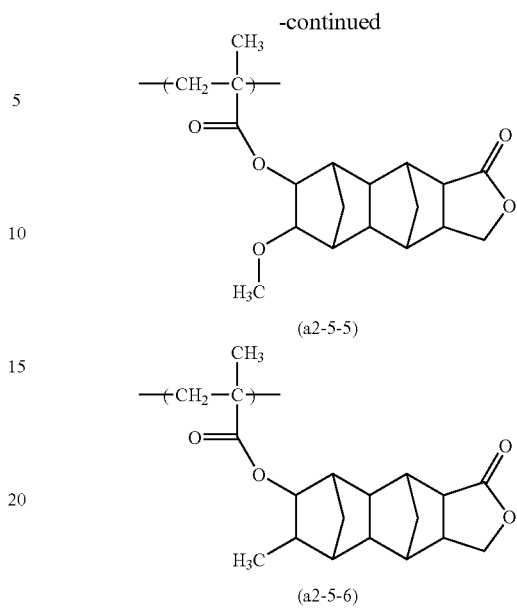

(a2-5-5)
(a2-5-6)

As the structural unit (a2), at least one structural unit selected from the group consisting of formulas (a2-1) to (a2-5) is preferable, and at least one structural unit selected from the group consisting of formulas (a2-1) to (a2-3) is more preferable. Specifically, it is preferable to use at least one structural unit selected from the group consisting of formulas (a2-1-1), (a2-1-2), (a2-1-3), (a2-1-4), (a2-2-1), (a2-2-2), (a2-3-1), (a2-3-2), (a2-3-9) and (a2-3-10).

As the structural unit (a2), one type of structural unit may be used, or two or more types may be used in combination.

In the polymeric compound (A1), the amount of the structural unit (a2) based on the combined total of all structural units constituting the polymeric compound (A1) is preferably 5 to 60 mol %, more preferably 10 to 55 mol %, and still more preferably 20 to 55 mol %. By making the amount of the structural unit (a2) at least as large as the lower limit of the above-mentioned range, the effect of using the structural unit (a2) can be satisfactorily achieved. On the other hand, by making the amount of the structural unit (a2) no more than the upper limit of the above-mentioned range, a good balance can be achieved with the other structural units.

<Structural Unit (a3)>

The structural unit (a3) is a structural unit derived from an acrylate ester containing a polar group-containing aliphatic hydrocarbon group.

When the polymeric compound (A1) has the structural unit (a3), the hydrophilicity of the polymeric compound (A1) is improved, and hence, the compatibility of the polymeric compound (A1) with the developing solution is improved. As a result, the alkali solubility of the exposed portions improves, which contributes to favorable improvements in the resolution.

Examples of the polar group include a hydroxyl group, cyano group, carboxyl group, or hydroxyalkyl group in which some of the hydrogen atoms of the alkyl group have been substituted with fluorine atoms, although a hydroxyl group is particularly desirable.

Examples of the aliphatic hydrocarbon group include linear or branched hydrocarbon groups (and preferably alkylene groups) of 1 to 10 carbon atoms, and polycyclic aliphatic hydrocarbon groups (polycyclic groups). These polycyclic groups can be selected appropriately from the multitude of groups that have been proposed for the resins of resist compositions designed for use with ArF excimer lasers. The polycyclic group preferably has 7 to 30 carbon atoms.

Of the various possibilities, structural units derived from an acrylate ester that include an aliphatic polycyclic group that contains a hydroxyl group, cyano group, carboxyl group or a hydroxyalkyl group in which some of the hydrogen atoms of the alkyl group have been substituted with fluorine atoms are particularly desirable. Examples of polycyclic groups include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2), and (a3-3) shown below are preferable.

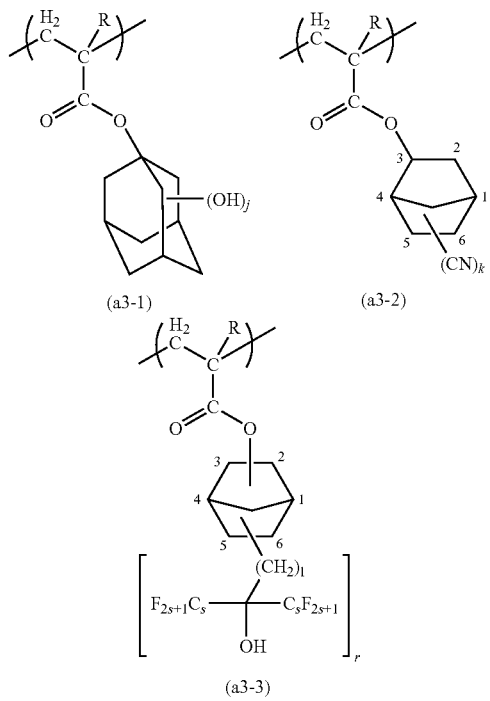

[Chemical Formula 21]

(a3-1)   (a3-2)

(a3-3)

wherein R is as defined above; j is an integer of 1 to 3; k is an integer of 1 to 3; t' is an integer of 1 to 3; l is an integer of 1 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbonyl group.

In formula (a3-3), t' is preferably 1, l is preferably 1 and s is preferably 1. Further, in formula (a3-3), it is preferable that a 2-norbonyl group or 3-norbonyl group be bonded to the terminal of the carboxy group of the acrylic acid. The fluorinated alkyl alcohol is preferably bonded to the 5th or 6th position of the norbonyl group.

As the structural unit (a3), one type of structural unit may be used, or two or more types may be used in combination.

In the polymeric compound (A1), the amount of structural unit (a3) based on the combined total of all structural units constituting the polymeric compound (A1) is preferably 5 to 50 mol %, more preferably 5 to 40 mol %, and still more preferably 5 to 35 mol %. By making the amount of the structural unit (a3) at least as large as the lower limit of the above-mentioned range, the effect of using the structural unit (a3) can be satisfactorily achieved. On the other hand, by making the amount of the structural unit (a3) no more than the upper limit of the above-mentioned range, a good balance can be achieved with the other structural units.

<Structural Unit (a1)>

The polymeric compound (A1) may also have a structural unit (a1) derived from an acrylate ester having an acid dissociable, dissolution inhibiting group, which is other than the structural units (a0), as long as the effects of the present invention are not impaired.

As the acid dissociable, dissolution inhibiting group with the structural unit (a1), the same as the acid dissociable, dissolution inhibiting group for $R^2$ defined above can be exemplified.

As the structural unit (a1), it is preferable to use at least one member selected from the group consisting of structural units represented by formula (a1-0-1) shown below and structural units represented by formula (a1-0-2) shown below.

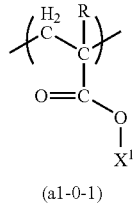

[Chemical Formula 22]

(a1-0-1)

wherein R represents a hydrogen atom, a lower alkyl group or a halogenated lower alkyl group; and $X^1$ represents an acid dissociable, dissolution inhibiting group.

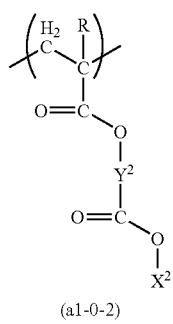

(a1-0-2)

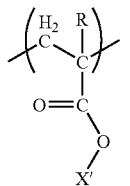

(a1-1)

(a1-2)

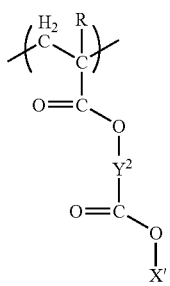

(a1-3)

wherein R represents a hydrogen atom, a lower alkyl group or a halogenated lower alkyl group; $X^2$ represents an acid dissociable, dissolution inhibiting group; and $Y^2$ represents an alkylene group or an aliphatic cyclic group.

In general formula (a1-0-1) shown above, lower alkyl group and halogenated lower alkyl group for R are the same as the lower alkyl group and halogenated lower alkyl group which can be bonded to the α-position of the aforementioned acrylate ester.

$X^1$ is not particularly limited as long as it is an acid dissociable, dissolution inhibiting group. Examples thereof include the aforementioned tertiary alkyl ester-type acid dissociable, dissolution inhibiting groups and acetal-type acid dissociable, dissolution inhibiting groups, and tertiary alkyl ester-type acid dissociable, dissolution inhibiting groups are preferable.

In general formula (a1-0-2), R is as defined above.

$X^2$ is the same as $X^1$ in general formula (a1-0-1).

$Y^2$ is preferably an alkylene group of 1 to 10 carbon atoms or a divalent aliphatic cyclic group. As the aliphatic cyclic group, the same as those exemplified above in connection with the explanation of "aliphatic cyclic group" can be used, except that two hydrogen atoms have been removed therefrom.

When $Y^2$ represents an alkylene group of 1 to 10 carbon atoms, it is more preferable that the number of carbons is 1 to 6, still more preferably 1 to 4, and most preferably 1 to 3.

When $Y^2$ represents a divalent aliphatic cyclic group, it is particularly desirable that the divalent aliphatic cyclic group be a group in which two or more hydrogen atoms have been removed from cyclopentane, cyclohexane, norbornane, isobornane, adamantane, tricyclodecane or tetracyclododecane.

Specific examples of the structural unit (a1) include structural units represented by general formulas (a1-1) to (a1-4) shown below.

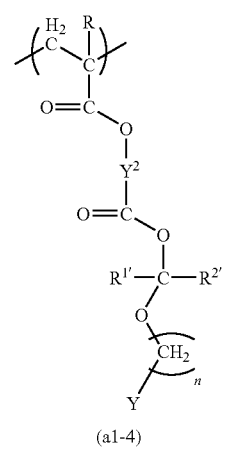

(a1-4)

wherein X' represents a tertiary alkyl ester-type acid dissociable, dissolution inhibiting group; Y represents a lower alkyl group of 1 to 5 carbon atoms or an aliphatic cyclic group; n represents an integer of 0 to 3; $Y^2$ is as defined above; R is as defined above; and each of $R^{1\prime}$ and $R^{2\prime}$ independently represents a hydrogen atom or a lower alkyl group of 1 to 5 carbon atoms.

As the tertiary alkyl ester-type acid dissociable, dissolution inhibiting group for X', the same as the tertiary alkyl ester-type acid dissociable, dissolution inhibiting groups for $X^1$ can be exemplified.

$R^{1\prime}$, $R^{2\prime}$, n and Y are respectively as defined for $R^{1\prime}$, $R^{2\prime}$, n and Y in general formula (p1) exemplified above in connection with the "acetal-type acid dissociable, dissolution inhibiting group".

$Y^2$ is as defined for $Y^2$ in general formula (a1-0-2).

Specific examples of structural units represented by general formula (a1-1) to (a1-4) are shown below.

[Chemical Formula 25]
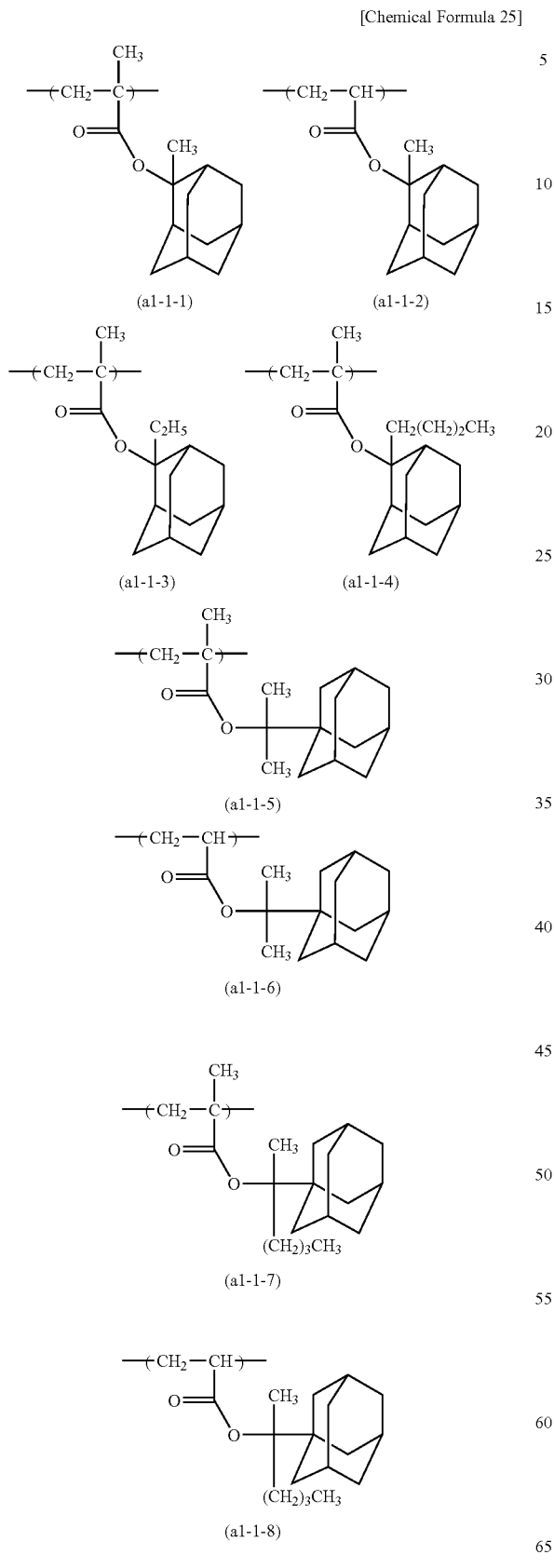
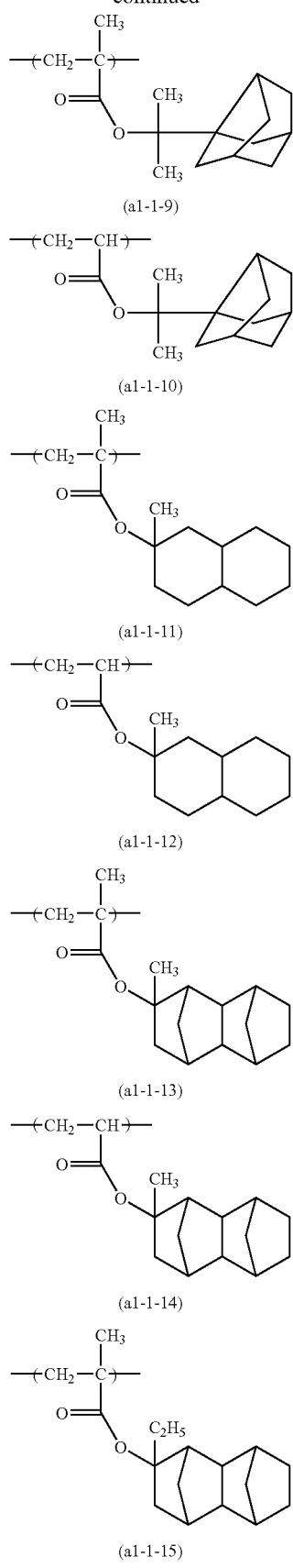

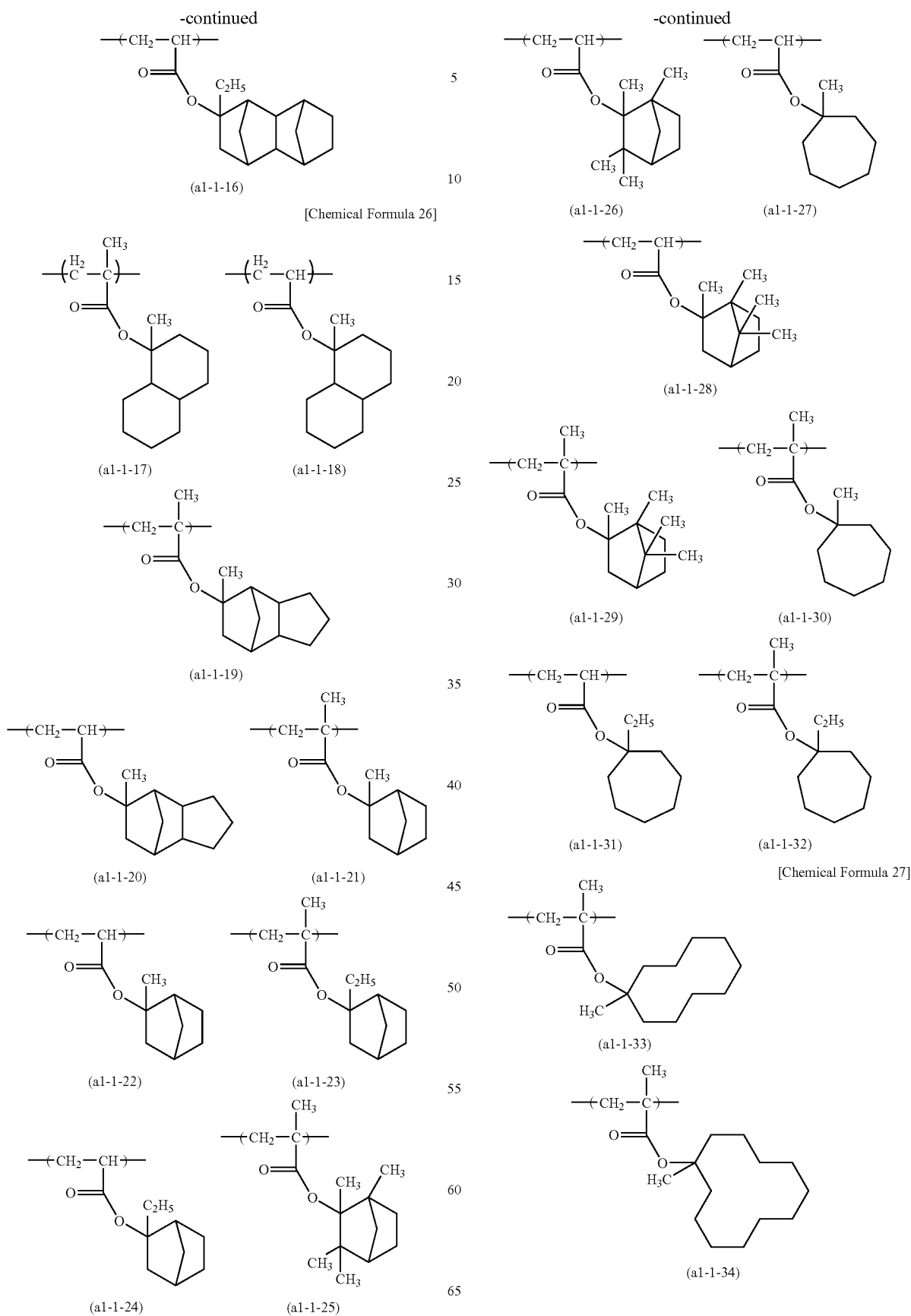

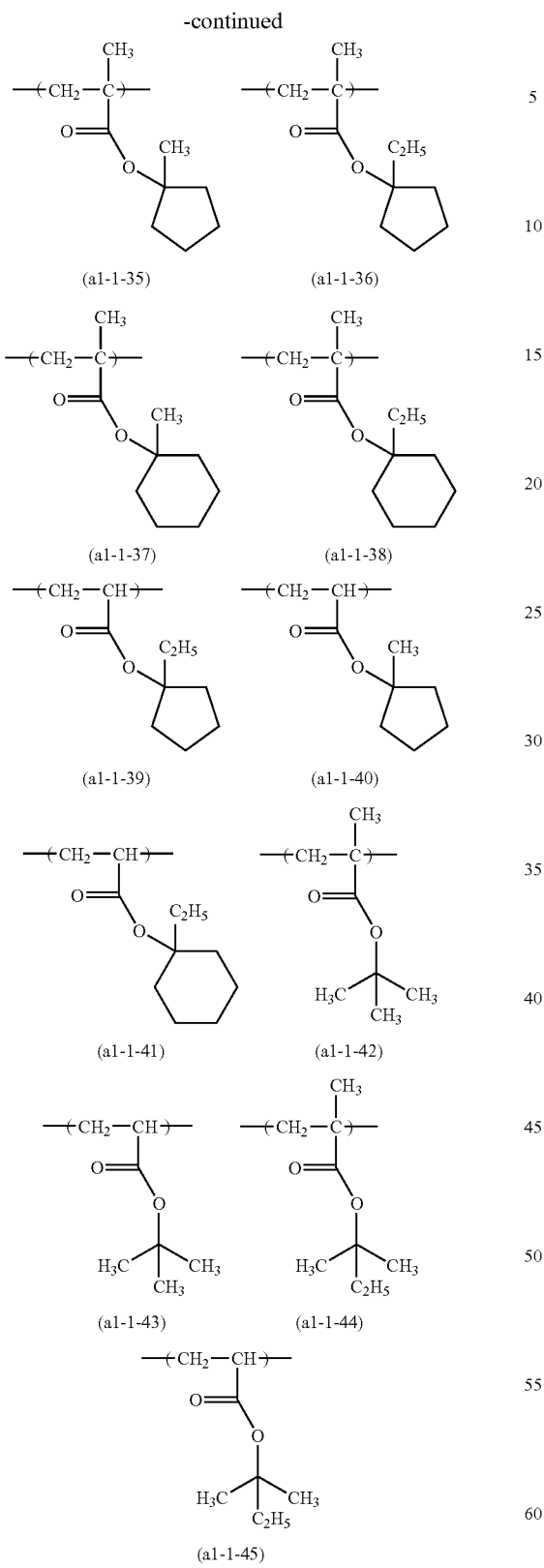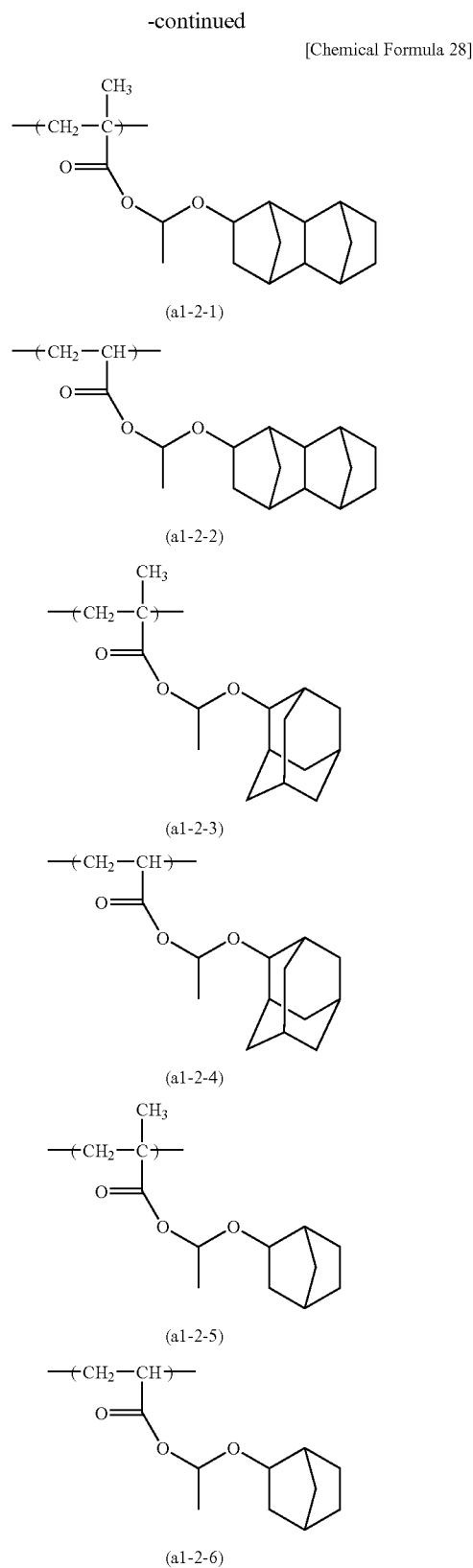

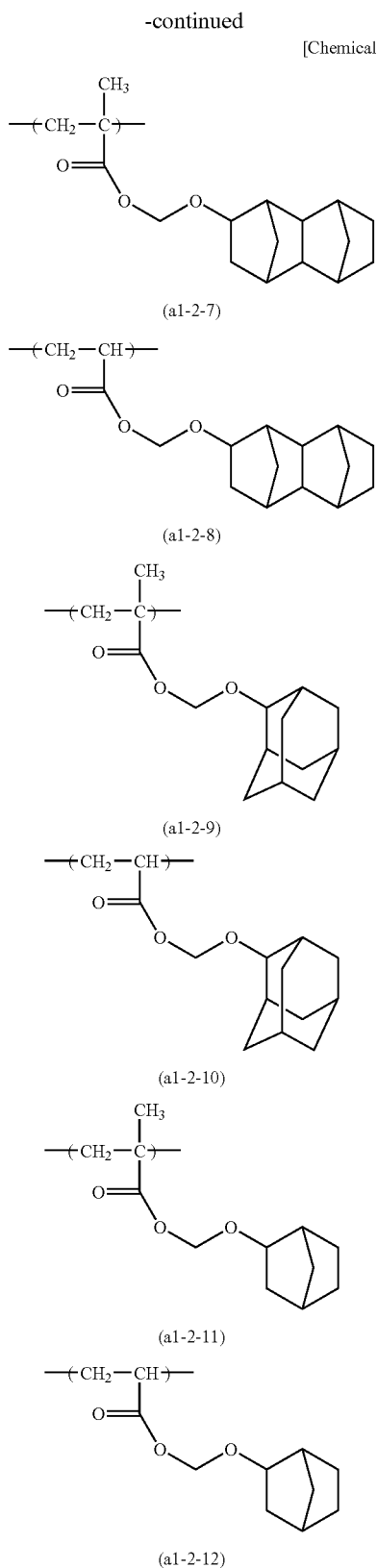
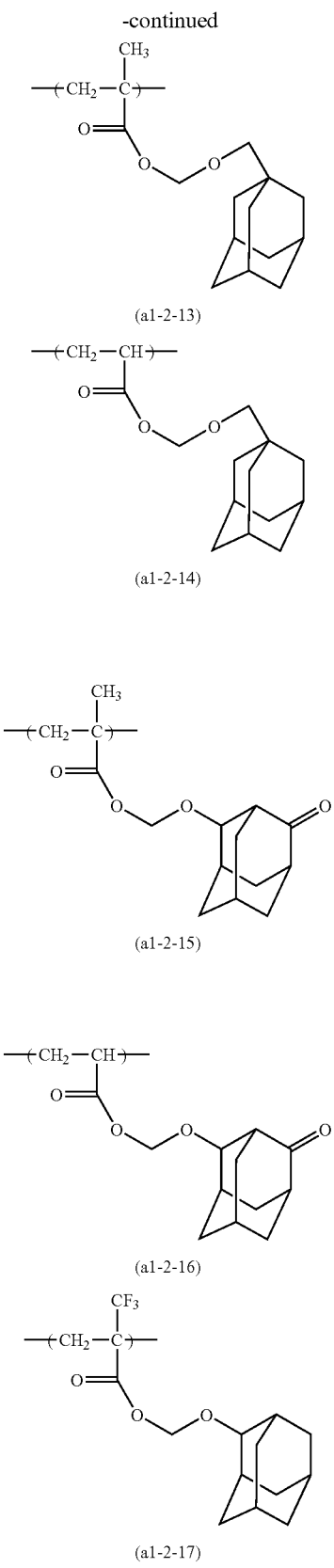

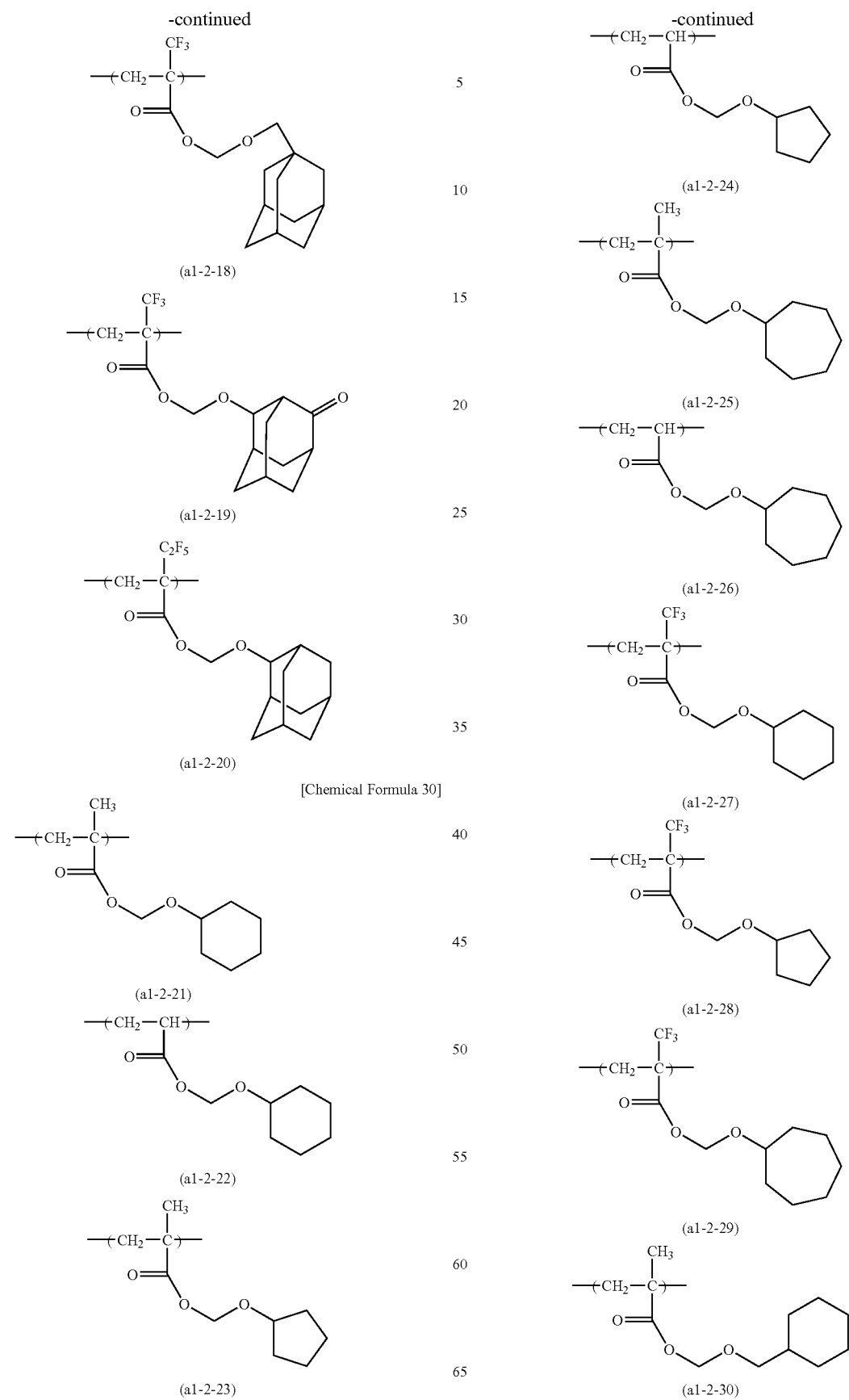

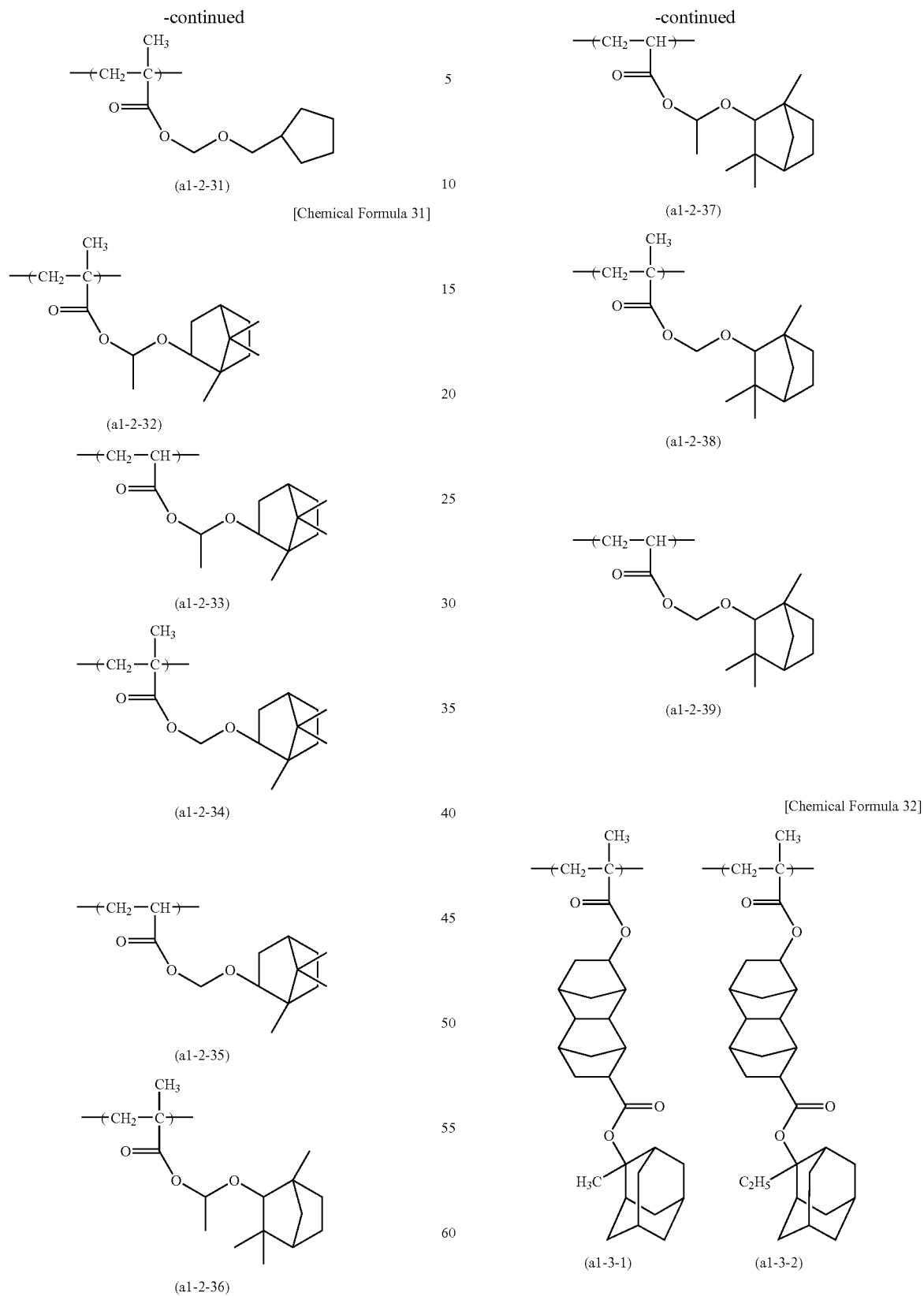

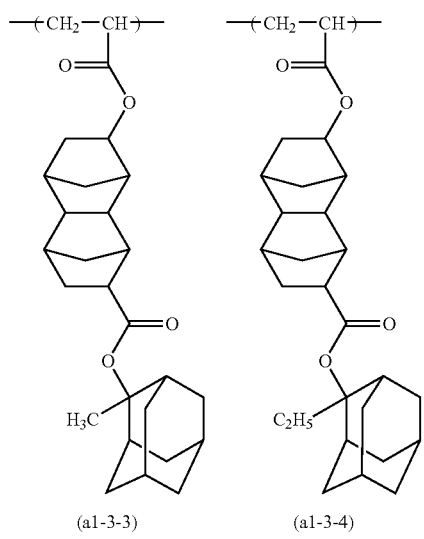
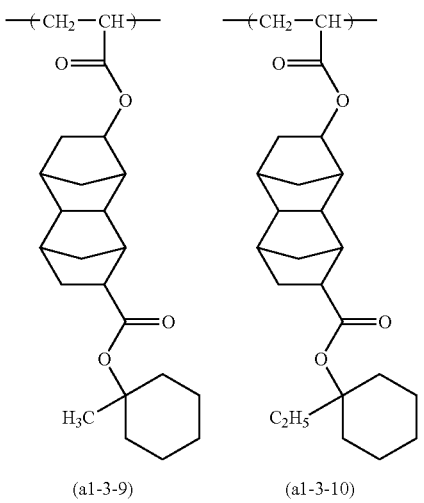

(a1-3-15) (a1-3-16) (a1-3-21) (a1-3-22)

(a1-3-17) (a1-3-18) (a1-3-23) (a1-3-24)

[Chemical Formula 33]

(a1-3-19) (a1-3-20)

[Chemical Formula 34]

(a1-4-1) (a1-4-2) (a1-4-3)

-continued
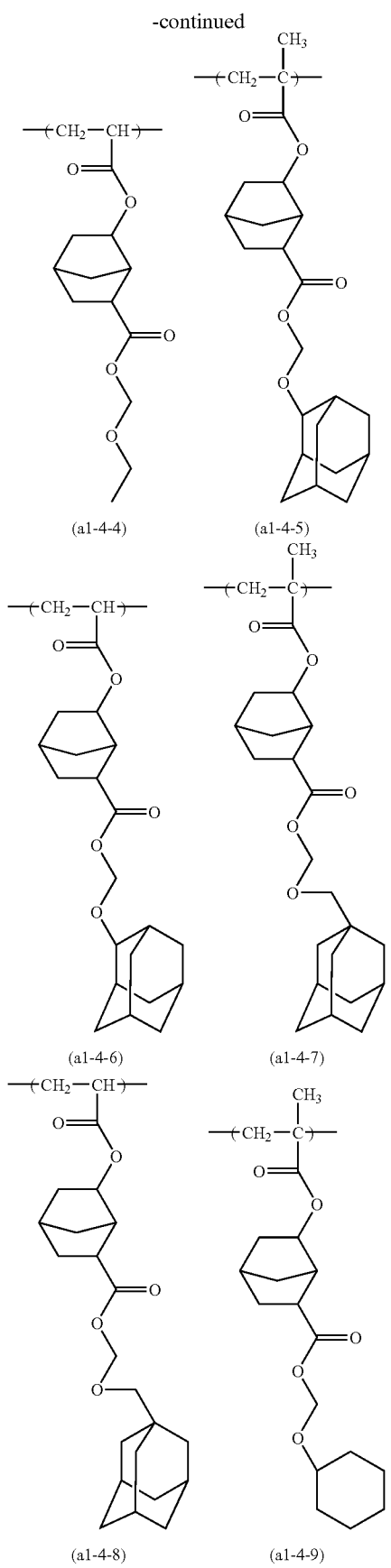
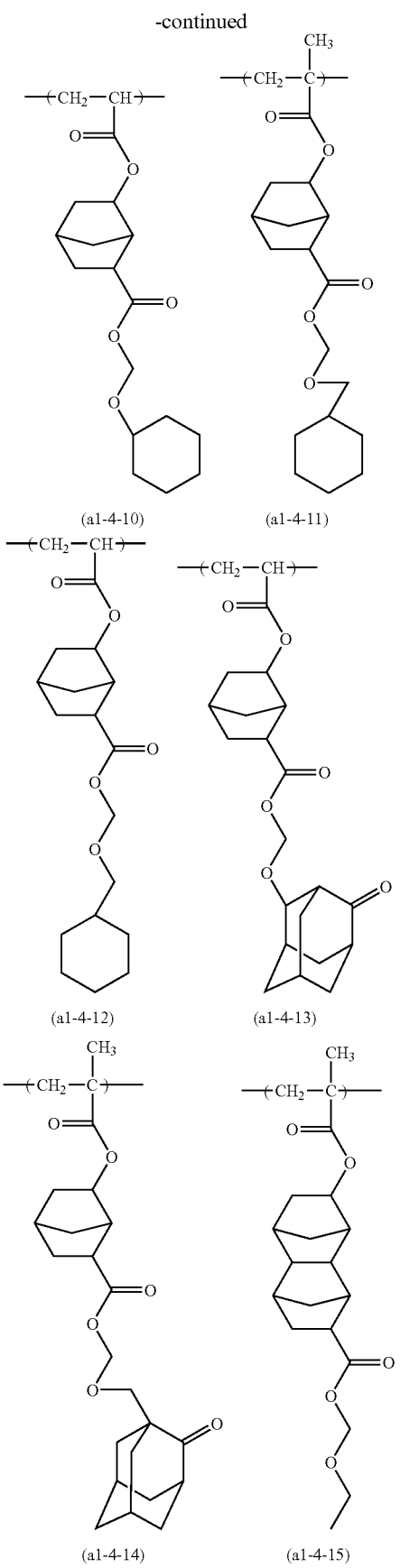

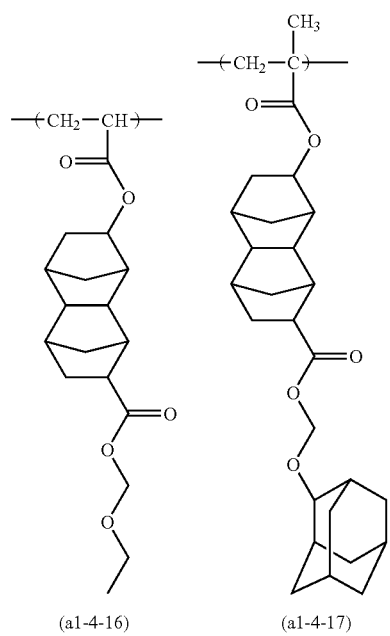
(a1-4-16)    (a1-4-17)
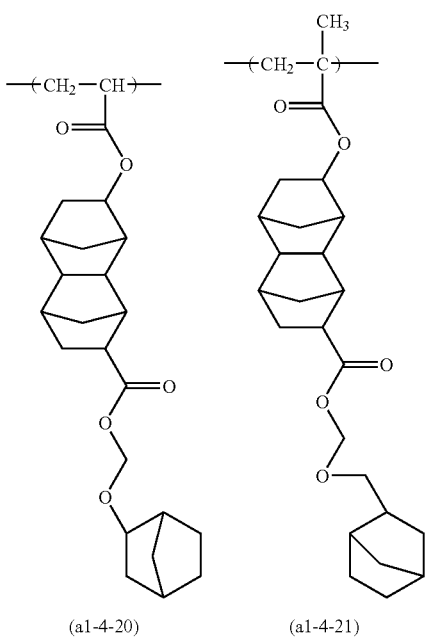
(a1-4-20)    (a1-4-21)
[Chemical Formula 35]
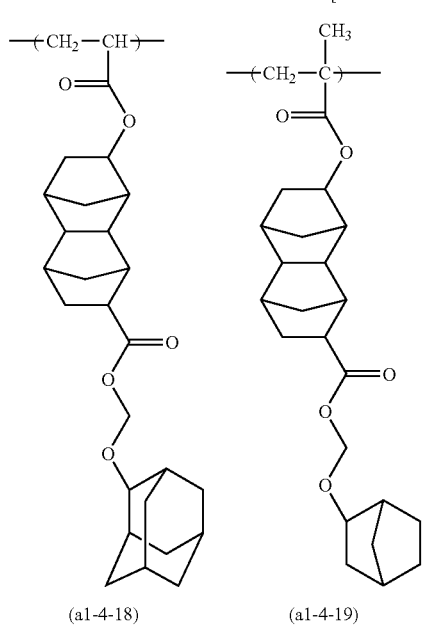
(a1-4-18)    (a1-4-19)
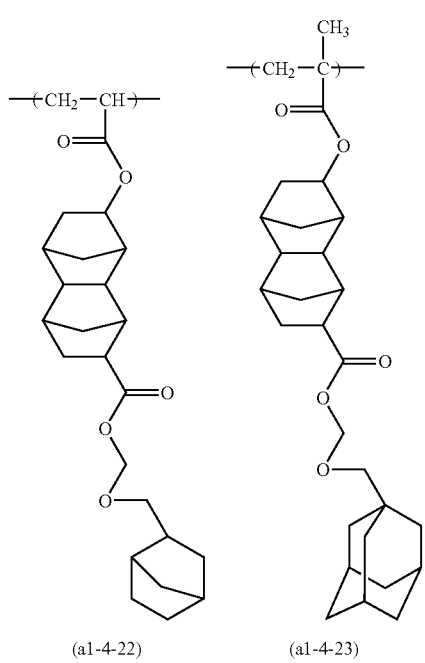
(a1-4-22)    (a1-4-23)

-continued
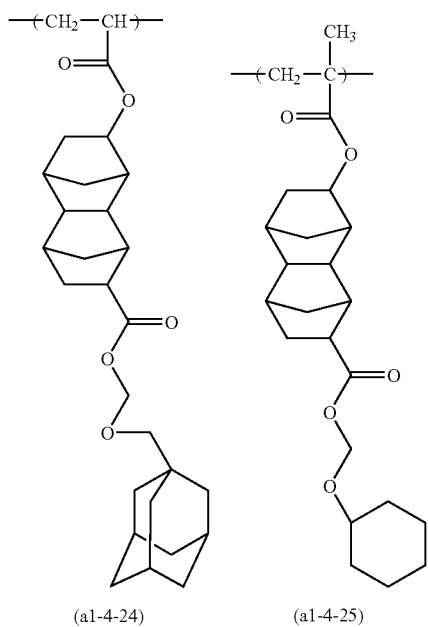
(a1-4-24)  (a1-4-25)
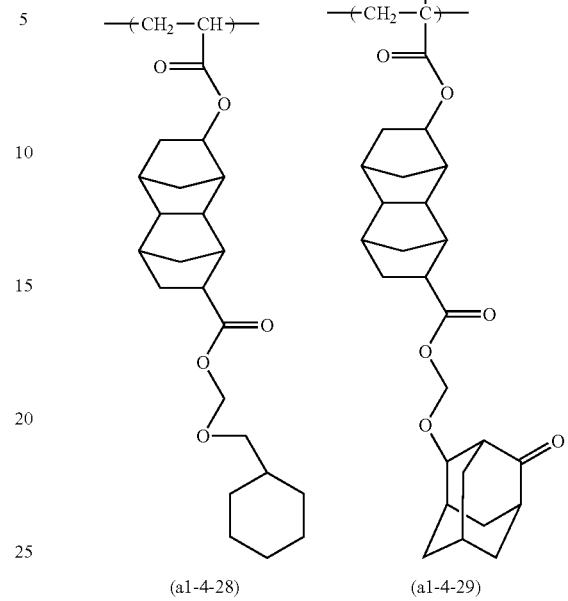
(a1-4-28)  (a1-4-29)
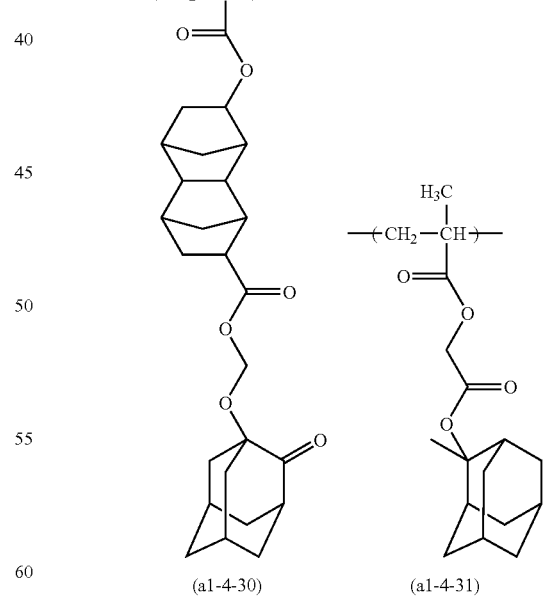
(a1-4-26)  (a1-4-27)  (a1-4-30)  (a1-4-31)

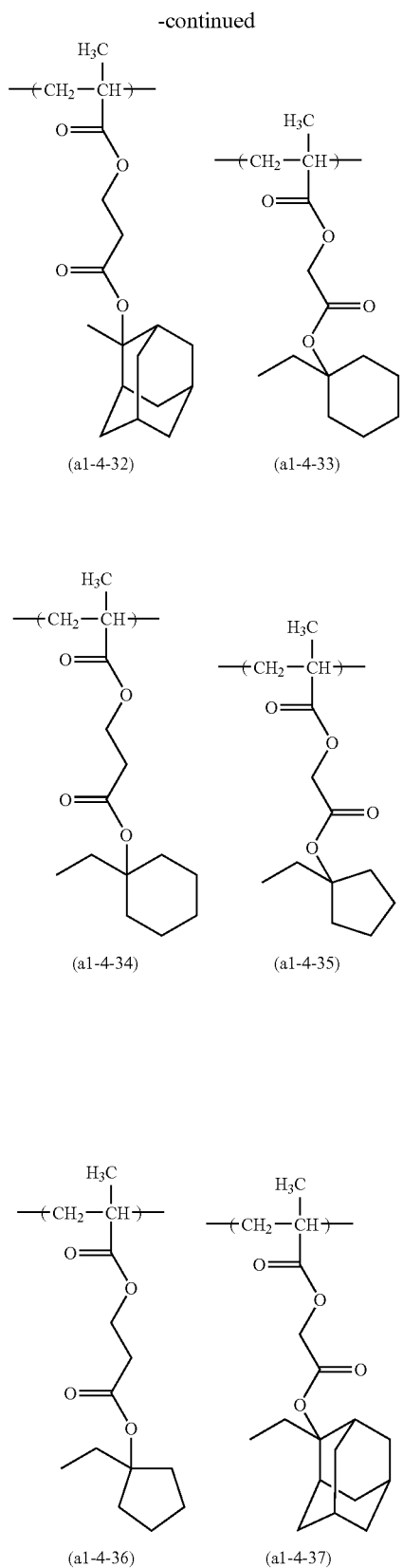
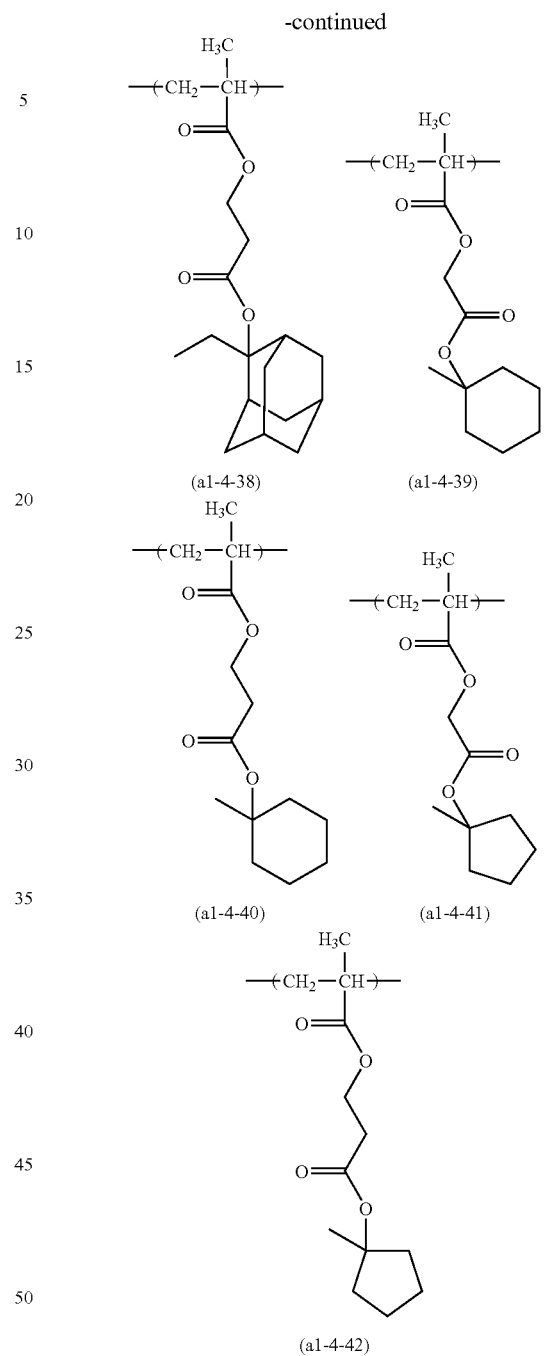

Among these, structural units represented by general formula (a1-1) are preferable. More specifically, at least one structural unit selected from the group consisting of structural units represented by formulas (a1-1-1) to (a-1-1-6) and (a1-1-35) to (a1-1-41) is more preferable.

Further, as the structural unit (a1), structural units represented by general formula (a1-1-01) shown below which includes the structural units represented by formulas (a1-1-1) to (a1-1-4), and structural units represented by general formula (a1-1-02) shown below which includes the structural units represented by formulas (a1-1-35) to (a1-1-41) are also preferable.

[Chemical Formula 36]

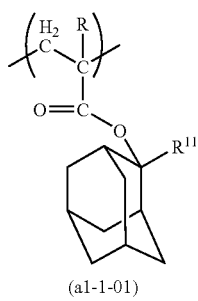

(a1-1-01)

wherein R represents a hydrogen atom, a lower alkyl group or a halogenated lower alkyl group; and $R^{11}$ represents a lower alkyl group.

[Chemical Formula 37]

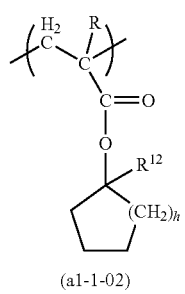

(a1-1-02)

wherein R represents a hydrogen atom, a lower alkyl group or a halogenated lower alkyl group; $R^{12}$ represents a lower alkyl group; and h represents an integer of 1 to 3.

In general formula (a1-1-01), R is as defined above.

The lower alkyl group for $R^{11}$ is the same as the lower alkyl group for R above, and is preferably a methyl group or an ethyl group.

In general formula (a1-1-02), R is as defined above.

The lower alkyl group for $R^{12}$ is the same as the lower alkyl group for R above. $R^{12}$ is preferably a methyl group or an ethyl group, and most preferably an ethyl group.

h is preferably 1 or 2, and most preferably 2.

In the polymeric compound (A1), as the structural unit (a1), one type may be used alone, or two or more types may be used in combination.

With respect to the amount of the structural unit (a1) in the polymeric compound (A1), as described above, the total amount of the structural unit (a0) and the below-described structural unit (a1) based on the combined total of all structural units constituting the polymeric compound (A1) is preferably 10 to 80 mol %, more preferably 20 to 70 mol %, and most preferably 25 to 50 mol %. By making the amount of the structural unit (a1) satisfy the lower limit of the above-mentioned range, a pattern can be easily formed using a resist composition prepared from the polymeric compound (A1). On the other hand, by making the amount of the structural unit (a1) satisfy the upper limit of the above-mentioned range, a good balance can be achieved with the other structural units.

<Structural Unit (a4)>

The polymeric compound (A1) may also have a structural unit (a4) which is other than the above-mentioned structural units (a0) to (a3), as long as the effects of the present invention are not impaired.

As the structural unit (a4), any other structural unit which cannot be classified as one of the above structural units (a0) to (a3) can be used without any particular limitations, and any of the multitude of conventional structural units used within resist resins for ArF excimer lasers or KrF excimer lasers (and particularly for ArF excimer lasers) can be used.

As the structural unit (a4), a structural unit which contains a non-acid-dissociable aliphatic polycyclic group, and is also derived from an acrylate ester is preferable. Examples of this polycyclic group include the same groups as those described above in connection with the aforementioned structural unit (a1), and any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecanyl group, adamantyl group, tetracyclododecanyl group, isobornyl group, and norbornyl group is particularly desirable. These polycyclic groups may be substituted with a linear or branched alkyl group of 1 to 5 carbon atoms.

Specific examples of the structural unit (a4) include units with structures represented by general formulas (a4-1) to (a4-5) shown below.

[Chemical Formula 38]

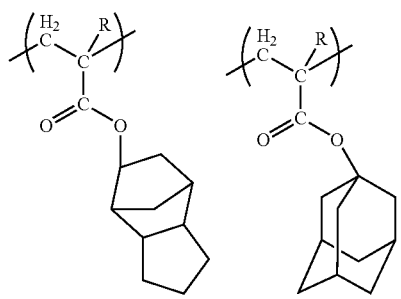

(a4-1)         (a4-2)

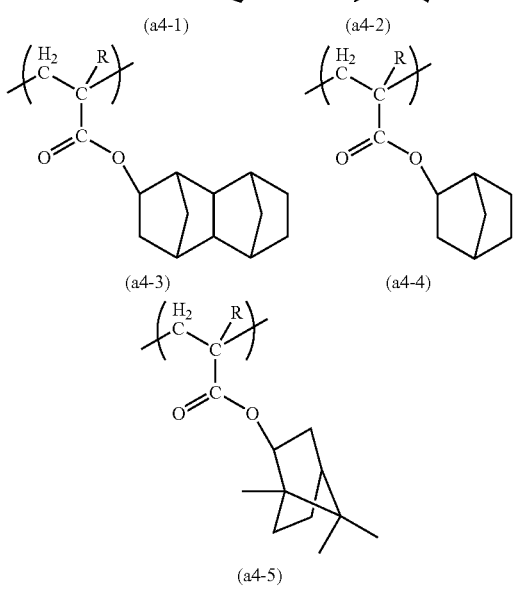

(a4-3)         (a4-4)

(a4-5)

wherein R is as defined above.

When the structural unit (a4) is included in the polymeric compound (A1), the amount of the structural unit (a4) based on the combined total of all the structural units that constitute the polymeric compound (A1) is preferably within the range from 1 to 30 mol %, and more preferably from 20 to 20 mol %.

In the present invention, the polymeric compound (A1) is preferably a copolymer having the structural unit (a0), (a2) and (a3). Examples of such a copolymer include a copolymer consisting of the structural units (a0), (a2) and (a3), a copolymer consisting of the structural units (a0), (a2), (a3) and (a4), and a copolymer consisting of the structural units (a0), (a2), (a3) and (a1).

In the present invention, as the polymeric compound (A1), it is particularly desirable to use a copolymer having a combination of structural units shown in formula (A1-11) below.

[Chemical Formula 39]

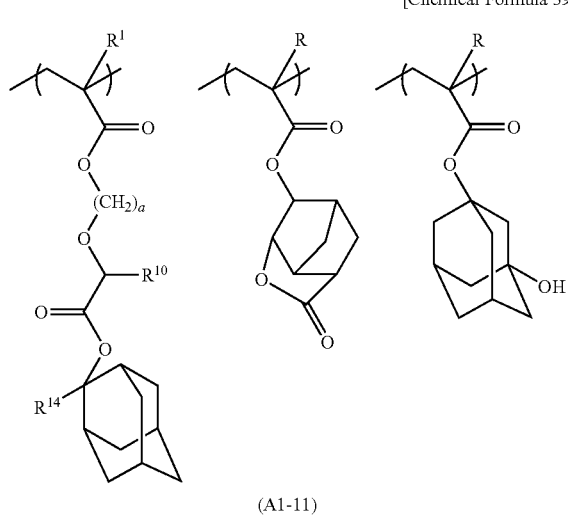

(A1-11)

where $R^1$, a, $R^{10}$ and $R^{14}$ are as defined above.

In formula (A1-11) above, $R^1$, a, $R^{10}$ and $R^{14}$ are respectively as defined for $R^1$, a, $R^{10}$ and $R^{14}$ in general formula (a0-1-1) above.

Further, R is as defined for R in the structural units (a2) and (a3), and the plurality of R may be the same or different.

The polymeric compound (A1) can be obtained, for example, by a conventional radical polymerization or the like of the compound (I) and, if desired, monomers corresponding with other structural units, using a radical polymerization initiator such as azobisisobutyronitrile (AIBN).

Furthermore, in the polymeric compound (A1), by using a chain transfer agent such as HS—$CH_2$—$CH_2CH_2$—$C(CF_3)_2$—OH, a —$C(CF_3)_2$—OH group can be introduced at the terminals of the polymeric compound (A1). Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

The weight average molecular weight (Mw) (the polystyrene equivalent value determined by gel permeation chromatography) of the polymeric compound (A1) is not particularly limited, but is preferably 2,000 to 50,000, more preferably 3,000 to 30,000, and most preferably 5,000 to 20,000. By making the weight average molecular weight no more than the upper limit of the above-mentioned range, the polymeric compound (A1) exhibits satisfactory solubility in a resist solvent when used as a resist. On the other hand, by making the weight average molecular weight at least as large as the lower limit of the above-mentioned range, dry etching resistance and cross-sectional shape of the resist pattern becomes satisfactory.

Further, the dispersity (Mw/Mn) is preferably 1.0 to 5.0, more preferably 1.0 to 3.0, and most preferably 1.2 to 2.5. Here, Mn is the number average molecular weight, The polymeric compound (A1) of the present invention is a novel compound conventionally unknown.

For example, in the case where the polymeric compound is blended with an acid-generator component (B) which generates acid upon exposure in a positive resist composition, when acid is generated from the acid-generator component (B) upon exposure (irradiation of radial rays), the bond between $R^2$ within the structural unit (a0) and the oxygen atom to which $R^2$ is bonded is broken by the action of the generated acid, and $R^2$ is dissociated. As a result, the solubility of the polymeric compound (A1) in an alkali developing solution is increased.

Therefore, the polymeric compound (A1) is useful as a base resin for a chemically amplified positive resist composition, and can be preferably used as the base component (A) for the positive resist composition of the present invention.

<<Positive Resist Composition>>

Next, the positive resist composition according to the first aspect of the present invention will be described.

The positive resist composition of the present invention includes a base component (A) (hereafter, referred to as "component (A)") which exhibits increased solubility in an alkali developing solution under action of acid and an acid-generator component (B) (hereafter, referred to as "component (B)") which generates acid upon exposure. Here, the term "base component" refers to an organic compound capable of forming a film.

In the positive resist composition, when radial rays are irradiated (when exposure is conducted), acid is generated from the component (B), and the solubility of the component (A) in an alkali developing solution is increased by the action of the generated acid. Therefore, in the formation of a resist pattern by conducting selective exposure of a resist film formed by using the positive resist composition of the present invention, the solubility of the exposed portions in an alkali developing solution is increased, whereas the solubility of the unexposed portions in an alkali developing solution is unchanged, and hence, a resist pattern can be formed by alkali developing.

<Component (A)>

The component (A) contains the aforementioned polymeric compound (A1) of the present invention.

In the component (A), as the polymeric compound (A1), one type of compound may be used, or a combination of two or more types may be used.

In the component (A), the amount of the polymeric compound (A1) based on the total amount of the component (A) is preferably 50 to 100% by weight, more preferably 80 to 100% by weight, and may be even 100% by weight.

The component (A) may contain "a base component which exhibits increased solubility in an alkali developing solution under action of acid" which is other than the polymeric compound (A1) (hereafter, referred to as "component (A2)"), as long as the effects of the present invention are not impaired.

The component (A2) is not particularly limited, and any of the multitude of conventional base components used within chemically amplified resist compositions (e.g., base resins used within chemically amplified resist compositions for ArF excimer lasers or KrF excimer lasers, preferably ArF excimer lasers) can be used. For example, as a base resin for ArF excimer laser, a base resin having the aforementioned structural unit (a1) as an essential component, and optionally the aforementioned structural units (a2) to (a4) can be mentioned.

As the component (A2), one type may be used, or a combination of two or more types may be used.

In the resist composition of the present invention, the amount of the component (A) can be appropriately adjusted depending on the thickness of the resist film to be formed, and the like.

<Component (B)>

As the component (B), there is no particular limitation, and any of the known acid generators used in conventional chemically amplified resist compositions can be used. Examples of these acid generators are numerous, and include onium salt-based acid generators such as iodonium salts and sulfonium salts; oxime sulfonate-based acid generators; diazomethane-based acid generators such as bisalkyl or bisaryl sulfonyl diazomethanes and poly(bis-sulfonyl)diazomethanes; nitrobenzylsulfonate-based acid generators; iminosulfonate-based acid generators; and disulfone-based acid generators.

As an onium salt-based acid generator, a compound represented by general formula (b-1) or (b-2) shown below can be used.

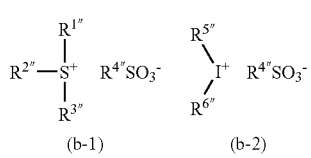

[Chemical Formula 40]

wherein $R^{1''}$ to $R^{3''}$, $R^{5''}$ and $R^{6''}$ each independently represents an aryl group or alkyl group, wherein two of $R^{1''}$ to $R^{3''}$ in formula (b-1) may be bonded to each other to form a ring with the sulfur atom; and $R^{4''}$ represents an alkyl group, a halogenated alkyl group, an aryl group or an alkenyl group which may have a substituent, with the proviso that at least one of $R^{1''}$ to $R^{3''}$ represents an aryl group, and at least one of $R^{5''}$ and $R^{6''}$ represents an aryl group.

In formula (b-1), $R^{1''}$ to $R^{3''}$ each independently represents an aryl group or an alkyl group. In formula (b-1), two of $R^{1''}$ to $R^{3''}$ in formula (b-1) may be bonded to each other to form a ring with the sulfur atom.

Further, among $R^{1''}$ to $R^{3''}$, at least one group represents an aryl group. Among $R^{1''}$ to $R^{3''}$, two or more groups are preferably aryl groups, and it is particularly desirable that all of $R^{1''}$ to $R^{3''}$ are aryl groups.

The aryl group for $R^{1''}$ to $R^{3''}$ is not particularly limited. For example, an aryl group having 6 to 20 carbon atoms may be used in which some or all of the hydrogen atoms of the aryl group may or may not be substituted with aryl groups, alkoxy groups, halogen atoms or hydroxyl groups.

The aryl group is preferably an aryl group having 6 to 10 carbon atoms because it can be synthesized at a low cost. Specific examples thereof include a phenyl group and naphthyl group.

The alkyl group, with which hydrogen atoms of the aryl group may be substituted, is preferably an alkyl group having 1 to 5 carbon atoms, and most preferably a methyl group, an ethyl group, a propyl group, an n-butyl group, or a tert-butyl group.

The alkoxy group, with which hydrogen atoms of the aryl group may be substituted, is preferably an alkoxy group having 1 to 5 carbon atoms, more preferably a methoxy group, an ethoxy group, n-propoxy group, iso-propoxy group, n-butoxy group or tert-butoxy group, and most preferably a methoxy group or an ethoxy group.

The halogen atom, with which hydrogen atoms of the aryl group may be substituted, is preferably a fluorine atom.

The alkyl group for $R^{1''}$ to $R^{3''}$ is not particularly limited and includes, for example, a linear, branched or cyclic alkyl group having 1 to 10 carbon atoms. In terms of achieving excellent resolution, the alkyl group preferably has 1 to 5 carbon atoms. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group, and a methyl group is most preferable because it is excellent in resolution and can be synthesized at a low cost.

When two of $R^{1''}$ to $R^{3''}$ in formula (b-1) are bonded to each other to form a ring with the sulfur atom, it is preferable that the two of $R^{1''}$ to $R^{3''}$ form a 3 to 10-membered ring including the sulfur atom, and it is particularly desirable that the two of $R^{1''}$ to $R^{3''}$ form a 5 to 7-membered ring including the sulfur atom.

When two of $R^{1''}$ to $R^{3''}$ in formula (b-1) are bonded to each other to form a ring with the sulfur atom, the remaining one of $R^{1''}$ to $R^{3''}$ is preferably an aryl group. As examples of the aryl group, the same as the above-mentioned aryl groups for $R^{1''}$ to $R^{3''}$ can be exemplified.

$R^{4''}$ represents an alkyl group, a halogenated alkyl group, an aryl group or an alkenyl group which may have a substituent.

The alkyl group for $R^{4''}$ may be any of linear, branched or cyclic.

The linear or branched alkyl group preferably has 1 to 10 carbon atoms, more preferably 1 to 8 carbon atoms, and most preferably 1 to 4 carbon atoms.

The cyclic alkyl group preferably has 4 to 15 carbon atoms, more preferably 4 to 10 carbon atoms, and most preferably 6 to 10 carbon atoms.

As the halogenated alkyl group for $R^{4''}$, a group in which a part or all of the hydrogen atoms of the aforementioned linear, branched or cyclic alkyl group have been substituted with halogen atoms can be exemplified. Examples of the halogen atom include a fluorine atom, a chlorine atom, a bromine atom and an iodine atom, and a fluorine atom is particularly desirable.

In the halogenated alkyl group, the percentage of the number of halogen atoms based on the total number of halogen atoms and hydrogen atoms (halogenation ratio (%)) is preferably 10 to 100%, more preferably 50 to 100%, and most preferably 100%. Higher halogenation ratio is preferable because the acid strength increases.

The aryl group for $R^{4''}$ is preferably an aryl group of 6 to 20 carbon atoms.

The alkenyl group for $R^{4''}$ is preferably an alkenyl group of 2 to 10 carbon atoms.

With respect to $R^{4''}$, the expression "may have a substituent" means that a part or all of the hydrogen atoms within the aforementioned linear, branched or cyclic alkyl group, halogenated alkyl group, aryl group or alkenyl group may be substituted with substituents (atoms other than hydrogen atoms, or groups).

$R^{4''}$ may have one substituent, or two or more substituents.

Examples of the substituent include a halogen atom, a hetero atom, an alkyl group, a group represented by the formula $R^5$—O— (wherein $R^5$ represents a monovalent aromatic organic group, a monovalent aliphatic hydrocarbon group or a hydroxyalkyl group), and a group represented by the formula $R^{51}$—O—C(O)— (wherein $R^{51}$ represents a monovalent aliphatic hydrocarbon group which may contain a hetero atom).

As the halogen atom and the alkyl group, the same as the halogen atom and alkyl group within the halogenated alkyl group for $R^{4"}$ may be exemplified.

Examples of the hetero atom include an oxygen atom, a nitrogen atom and a sulfur atom.

With respect to the group represented by the formula $R^5$—O—, examples of the monovalent aromatic organic group for $R^5$ include aryl groups in which one hydrogen atom has been removed from an aromatic hydrocarbon ring, such as a phenyl group, a biphenyl group, a fluorenyl group, a naphthyl group, an anthryl group, and a phenanthryl group; heteroaryl groups in which a part of the carbon atoms constituting the ring(s) of these groups are substituted with hetero atoms such as an oxygen atom, a sulfur atom, and a nitrogen atom; and arylalkyl groups such as a benzyl group, a phenethyl group, 1-naphthylmethyl group, a 2-naphthylmethyl group, a 1-naphthylethyl group and a 2-naphthylethyl group.

The alkyl chain with the arylalkyl group preferably has 1 to 4 carbon atom, more preferably 1 or 2, and most preferably 1.

These aryl groups, heteroaryl groups and arylalkyl groups may have a substituent such as an alkyl group of 1 to 10 carbon atoms, a halogenated alkyl group, an alkoxy group, a hydroxyl group or a halogen atom. The alkyl group or halogenated alkyl group as the substituent preferably has 1 to 8 carbon atoms, and more preferably 1 to 4 carbon atoms. The halogenated aryl group is preferably a fluorinated alkyl group, Examples of halogen atoms include a fluorine atom, a chlorine atom, a bromine atom and an iodine atom, and a fluorine atom is preferable.

As the monovalent aromatic organic group for $R^5$, an arylalkyl group is preferable, an arylmethyl group is more preferable, and a naphthylmethyl group is most preferable.

As the monovalent aliphatic hydrocarbon group for $R^5$, for example, a linear, branched or cyclic, monovalent saturated hydrocarbon group of 1 to 15 carbon atoms, or a linear or branched, monovalent unsaturated hydrocarbon group of 2 to 5 carbon atoms can be mentioned.

Examples of linear, monovalent saturated hydrocarbon groups include a methyl group, ethyl group, propyl group, butyl group, pentyl group, hexyl group, heptyl group, octyl group, nonyl group and decanyl group.

Examples of branched, monovalent saturated hydrocarbon groups include a 1-methylethyl group, 1-methylpropyl group, 2-methylpropyl group, 1-methylbutyl group, 2-methylbutyl group, 3-methylbutyl group, 1-ethylbutyl group, 2-ethylbutyl group, 1-methylpentyl group, 2-methylpentyl group, 3-methylpentyl group and 4-methylpentyl group.

The cyclic, monovalent saturated hydrocarbon group may be either a polycyclic group or a monocyclic group. For example, groups in which one hydrogen atom has been removed from a monocycloalkane or a polycycloalkane such as a bicycloalkane, tricycloalkane or tetracycloalkane can be mentioned. Specific examples include groups in which one hydrogen atom has been removed from a monocycloalkane such as cyclopentane, cyclohexane, cycloheptane or cyclooctane; and groups in which one hydrogen atom has been removed from a polycycloalkane such as adamantane, norbornane, isobornane, tricyclodecane or tetracyclododecane.

Examples of linear, monovalent unsaturated hydrocarbon group include a vinyl group, propenyl group (allyl group) and butynyl group.

Examples of branched, monovalent unsaturated hydrocarbon group include 1-methylpropenyl group and 2-methylpropenyl group.

The monovalent aliphatic hydrocarbon group for $R^5$ preferably has 2 to 4 carbon atoms, and it is particularly desirable that the monovalent aliphatic hydrocarbon group have 3 carbon atoms.

The hydroxyalkyl group for $R^5$ is a linear, branched or cyclic, monovalent saturated hydrocarbon group in which at least one hydrogen atom has been substituted with a hydroxyl group. Linear or branched, monovalent saturated hydrocarbon groups in which one or two hydrogen atoms have been substituted with hydroxyl groups are preferable. Specific examples include a hydroxymethyl group, hydroxyethyl group, 1-hydroxypropyl group, 2-hydoxypropyl group, 3-hydroxypropyl group and 2,3-dihydroxypropyl group.

The monovalent hydroxyalkyl group for $R^5$ preferably has 1 to 10 carbon atoms, more preferably 1 to 8 carbon atoms, still more preferably 1 to 6 carbon atoms, and most preferably 1 to 3 carbon atoms.

In the group represented by the formula $R^{51}$—O—C(O)—, as the monovalent aliphatic hydrocarbon group for $R^{51}$, the same as the monovalent aliphatic hydrocarbon group for $R^5$ may be exemplified, and a cyclic alkyl group is particularly desirable. The cyclic alkyl group may have a substituent.

Examples of the substituent include a lower alkyl group of 1 to 5 carbon atoms, a fluorine atom, a fluorinated alkyl group of 1 to 5 carbon atoms and an oxygen atom (=O).

The monovalent aliphatic hydrocarbon group may contain a hetero atom. Examples of cyclic alkyl groups containing a hetero atom include groups represented by formulas (L1) to (L5) and (S1) to (S4) shown below.

[Chemical Formula 41]

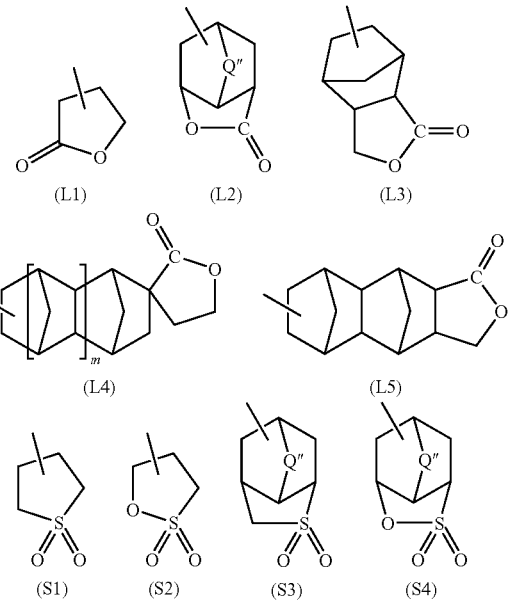

wherein Q" represents an alkylene group of 1 to 5 carbon atoms, —O—, —S—, —O—$R^{94}$— or —S—$R^{95}$— (wherein each of $R^{94}$ and $R^{95}$ independently represents an alkylene group of 1 to 5 carbon atoms); and m represents 0 or 1.

In formula (b-2), $R^{5"}$ and $R^{6"}$ each independently represents an aryl group or alkyl group. At least one of $R^{5"}$ and $R^{6"}$ represents an aryl group. It is preferable that both of $R^{5"}$ and $R^{6"}$ represent an aryl group.

As the aryl group for $R^{5"}$ and $R^{6"}$ the same as the aryl groups for $R^{1"}$ to $R^{3"}$ can be exemplified.

As the alkyl group for $R^{5'''}$ and $R^{6'''}$, the same as the alkyl groups for $R^{1'''}$ to $R^{3'''}$ can be exemplified.

It is particularly desirable that both of $R^{5'''}$ and $R^{6'''}$ represents a phenyl group.

As $R^{4'''}$ in formula (b-2), the same as those mentioned above for $R^{4'''}$ in formula (b-1) can be exemplified.

Specific examples of suitable onium salt-based acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate, 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate; heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

It is also possible to use onium salts in which the anion moiety of these onium salts are replaced by methanesulfonate, n-propanesulfonate, n-butanesulfonate, or n-octanesulfonate.

Further, onium salt-based acid generators in which the anion moiety in general formula (b-1) or (b-2) is replaced by an anion moiety represented by general formula (b-3) or (b-4) shown below (the cation moiety is the same as (b-1) or (b-2)) may be used.

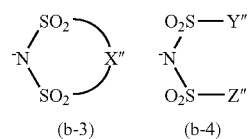

[Chemical Formula 42]

wherein X" represents an alkylene group of 2 to 6 carbon atoms in which at least one hydrogen atom has been substituted with a fluorine atom; and each of Y" and Z" independently represents an alkyl group of 1 to 10 carbon atoms in which at least one hydrogen atom has been substituted with a fluorine atom.

X" represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

Y" and Z" each independently represents a linear or branched alkyl group in which at least one hydrogen atom has been substituted with a fluorine atom, and the alkyl group has 1 to 10 carbon atoms, preferably 1 to 7 carbon atoms, and more preferably 1 to 3 carbon atoms.

The smaller the number of carbon atoms of the alkylene group of X" or those of the alkyl group of Y" and Z" within the range of the number of carbon atoms, the better the solubility in a resist solvent.

Further, in the alkylene group of X" or the alkyl group of Y" and Z", it is preferable that the number of hydrogen atoms substituted with fluorine atoms is as large as possible, as the acid strength increases, and the transparency to high energy radiation of 200 nm or less or electron beam is improved. The fluorination ratio of the alkylene group or alkyl group is preferably from 70 to 100%, more preferably from 90 to 100%, and it is particularly desirable that the alkylene group or alkyl group be a perfluoroalkylene group or perfluoroalkyl group in which all hydrogen atoms are substituted with fluorine atoms.

Furthermore, as an onium salt-based acid generator, a sulfonium salt having a cation moiety represented by general formula (b-5) or (b-6) shown below may be used.

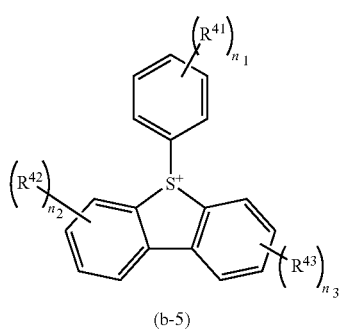

[Chemical Formula 43]

(b-5)

-continued

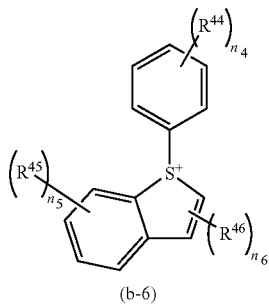

(b-6)

wherein each of $R^{41}$ to $R^{46}$ independently represents an alkyl group, an acetyl group, an alkoxy group, a carboxy group, a hydroxyl group or a hydroxyalkyl group; each of $n_1$ to $n_5$ independently represents an integer of 0 to 3; and represents an integer of 0 to 2.

With respect to $R^{41}$ to $R^{46}$, the alkyl group is preferably an alkyl group of 1 to 5 carbon atoms, more preferably a linear or branched alkyl group, and most preferably a methyl group, ethyl group, propyl group, isopropyl group, n-butyl group or tert butyl group.

The alkoxy group is preferably an alkoxy group of 1 to 5 carbon atoms, more preferably a linear or branched alkoxy group, and most preferably a methoxy group or ethoxy group.

The hydroxyalkyl group is preferably the aforementioned alkyl group in which one or more hydrogen atoms have been substituted with hydroxy groups, and examples thereof include a hydroxymethyl group, hydroxyethyl group and hydroxypropyl group.

When the subscripts $n_1$ to $n_6$ of $R^{41}$ to $R^{46}$ represent an integer of 2 or more, the plurality of $R^{41}$ to $R^{46}$ may be the same or different.

$n_1$ is preferably 0 to 2, more preferably 0 or 1, and still more preferably 0.

It is preferable that $n_2$ and $n_3$ each independently represent 0 or 1, and more preferably 0.

$n_4$ is preferably 0 to 2, and more preferably 0 or 1.

$n_5$ is preferably 0 or 1, and more preferably 0.

$n_6$ is preferably 0 or 1, and more preferably 1.

The anion moiety of the sulfonium salt having a cation moiety represented by general formula (b-5) or (b-6) is not particularly limited, and the same anion moieties for onium salt-based acid generators which have been proposed may be used. Examples of such anion moieties include fluorinated alkylsulfonic acid ions such as anion moieties ($R^{4'''}SO_3$) for onium salt-based acid generators represented by general formula (b-1) or (b-2) shown above; and anion moieties represented by general formula (b-3) or (b-4) shown above.

In the present description, an oximesulfonate-based acid generator is a compound having at least one group represented by general formula (B-1) shown below, and has a feature of generating acid by irradiation. Such oximesulfonate-based acid generators are widely used for a chemically amplified resist composition, and can be appropriately selected.

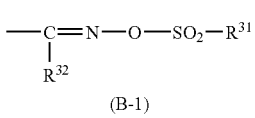

[Chemical Formula 44]

(B-1)

wherein each of $R^{31}$ and $R^{32}$ independently represents an organic group.

The organic group for $R^{31}$ and $R^{32}$ refers to a group containing a carbon atom, and may include atoms other than carbon atoms (e.g., a hydrogen atom, an oxygen atom, a nitrogen atom, a sulfur atom, a halogen atom (such as a fluorine atom and a chlorine atom) and the like).

As the organic group for $R^{31}$, a linear, branched, or cyclic alkyl group or aryl group is preferable. The alkyl group or the aryl group may have a substituent. The substituent is not particularly limited, and examples thereof include a fluorine atom and a linear, branched, or cyclic alkyl group having 1 to 6 carbon atoms. The expression "having a substituent" mean that some or all of the hydrogen atoms of the alkyl group or the aryl group are substituted with substituents.

The alkyl group preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which some of the hydrogen atoms are substituted with halogen atoms, and the "completely halogenated alkyl group" refers to an alkyl group in which all of the hydrogen atoms are substituted with halogen atoms. Examples of the halogen atom include a fluorine atom, a chlorine atom, a bromine atom and an iodine atom, and a fluorine atom is particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, partially or completely halogenated aryl group is particularly desirable. The "partially halogenated aryl group" refers to an aryl group in which some of the hydrogen atoms are substituted with halogen atoms, and the "completely halogenated aryl group" refers to an aryl group in which all of hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched, or cyclic alkyl group, aryl group, or cyano group is preferable. Examples of the alkyl group and the aryl group for $R^{32}$ are the same as those of the alkyl group and the aryl group for $R^{31}$.

As $R^{32}$, a cyano group, an alkyl group of 1 to 8 carbon atoms having no substituent or a fluorinated alkyl group of 1 to 8 carbon atoms is particularly desirable.

Preferred examples of the oxime sulfonate-based acid generator include compounds represented by general formula (B-2) or (B-3) shown below.

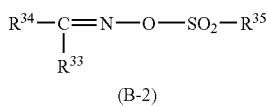

[Chemical Formula 45]

(B-2)

wherein $R^{33}$ represents a cyano group, an alkyl group having no substituent or a halogenated alkyl group; $R^{34}$ represents an aryl group; and $R^{35}$ represents an alkyl group having no substituent or a halogenated alkyl group.

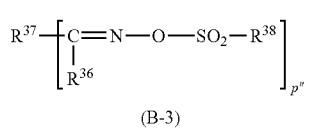

[Chemical Formula 46]

(B-3)

wherein $R^{36}$ represents a cyano group, an alkyl group having no substituent or a halogenated alkyl group; $R^{37}$ represents a divalent or trivalent aromatic hydrocarbon group; $R^{38}$ represents an alkyl group having no substituent or a halogenated alkyl group; and p" represents 2 or 3.

In general formula (B-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more, and most preferably 90% or more.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group, and a phenanthryl group, and heteroaryl groups in which some of the carbon atoms constituting the ring(s) of these groups are substituted with hetero atoms such as an oxygen atom, a sulfur atom, and a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group and halogenated alkyl group as the substituent preferably has 1 to 8 carbon atoms, and more preferably 1 to 4 carbon atoms. The halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms fluorinated, more preferably 70% or more, still more preferably 90% or more. A completely fluorinated alkyl group in which 100% of the hydrogen atoms are substituted with fluorine atoms is particularly desirable.

In general formula (B-3), the alkyl group having no substituent and the halogenated alkyl group for $R^{36}$ are the same as the alkyl group having no substituent and the halogenated alkyl group for $R^{33}$.

Examples of the divalent or trivalent aromatic hydrocarbon group for $R^{37}$ include groups in which one or two hydrogen atoms have been removed from the aryl group for $R^{34}$.

As the alkyl group having no substituent or the halogenated alkyl group for $R^{38}$, the same one as the alkyl group having no substituent or the halogenated alkyl group for $R^{35}$ can be used.

p" is preferably 2.

Specific examples of suitable oxime sulfonate-based acid generators include α-(p-toluenesulfonyloxyamino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)p-methylphenyl acetonitrile, and α-(methylsulfonyloxyimino)-p-bromophenyl acetonitrile.

Further, oxime sulfonate-based acid generators disclosed in Japanese Unexamined Patent Application, First Publication No. Hei 9-208554 (Chemical Formulas 18 and 19 shown in paragraphs [0012] to [0014]) and oxime sulfonate-based acid generators disclosed in WO 2004/074242A2 (Examples 1 to 40 described at pages 65 to 85) may be preferably used.

Further, as preferable examples, the following can be exemplified.

[Chemical Formula 47]

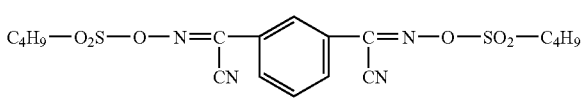

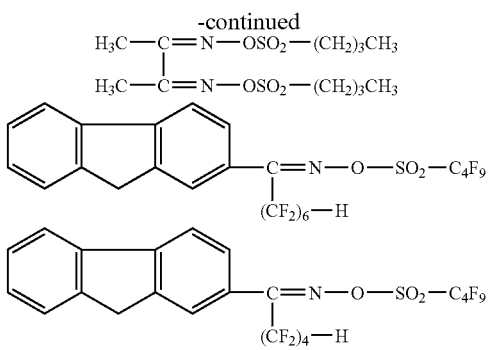

Of the aforementioned diazomethane-based acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane-based acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may be preferably used.

Furthermore, as poly(bis-sulfonyl)diazomethanes those disclosed in Japanese Unexamined Patent Application, First Publication No. Hei 11-322707, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane, may be exemplified.

As the component (B), one type of acid generator may be used, or two or more types may be used in combination.

In the present invention, as the component (B), it is preferable to use an onium salt having a fluorinated alkylsulfonic acid ion, which may have a substituent as the anion moiety.

In the resist composition for immersion exposure according to the present invention, the amount of the component (B) is preferably 0.5 to 30 parts by weight, and more preferably 1 to 10 parts by weight, relative to 100 parts by weight of the component (A). When the amount of the component (B) is within the above-mentioned range, formation of a resist pattern can be satisfactorily performed. Further, by virtue of the above-mentioned range, a uniform solution can be obtained and the storage stability becomes satisfactory.

<Optional Component>

In the positive resist composition of the present invention, for improving the resist pattern shape and the post exposure stability of the latent image formed by the pattern-wise exposure of the resist layer, a nitrogen-containing organic compound (D) (hereafter referred to as the component (D)) may be added as an optional component.

A multitude of these components (D) have already been proposed, and any of these known compounds may be used, although an aliphatic amine, and particularly a secondary aliphatic amine or tertiary aliphatic amine is preferable. The term "aliphatic cyclic group" refers to a monocyclic group or polycyclic group that has no aromaticity. An aliphatic amine is an amine having one or more aliphatic groups, and the aliphatic groups preferably have 1 to 20 carbon atoms.

Examples of these aliphatic amines include amines in which at least one hydrogen atom of ammonia ($NH_3$) has been substituted with an alkyl group or hydroxyalkyl group of no more than 20 carbon atoms (i.e., alkylamines or alkylalcoholamines), and cyclic amines.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, tri-n-octanolamine, stearyldiethanolamine and laurildiethanolamine.

Among these trialkylamines of 5 to 10 carbon atoms and alkylalcoholamines are preferable, tri-n-pentylamine, diethanolamine and stearyldiethanolamine are particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of other aliphatic amines include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine and tris[2-{2-(2-hydroxyethoxy)ethoxy}ethyl]amine.

These compounds can be used either alone, or in combinations of two or more different compounds.

The component (D) is typically used in an amount within a range from 0.01 to 5.0 parts by weight, relative to 100 parts by weight of the component (A).

Furthermore, in the positive resist composition of the present invention, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphorus oxo acid or derivative thereof can be added.

Examples of suitable organic carboxylic acids include acetic acid, malonic acid, citric acid, malic acid, succinic acid, benzoic acid, and salicylic acid.

Examples of phosphorus oxo acids or derivatives thereof include phosphoric acid, phosphonic acid and phosphinic acid. Among these, phosphonic acid is particularly desirable.

Examples of oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters such as phenylphosphinic acid.

As the component (E), one type may be used alone, or two or more types may be used in combination.

The component (E) is typically used in an amount within a range from 0.01 to 5.0 parts by weight, relative to 100 parts by weight of the component (A).

If desired, other miscible additives can also be added to the positive resist composition of the present invention. Examples of such miscible additives include additive resins for improving the performance of the resist film, surfactants for improving the applicability, dissolution inhibitors, plasticizers, stabilizers, colorants, halation prevention agents, and dyes.

<Organic Solvent (S)>

The positive resist composition of the present invention can be prepared by dissolving the materials for the resist composition in an organic solvent (hereafter, frequently referred to as "component (S)").

The component (S) may be any organic solvent which can dissolve the respective components to give a uniform solution, and any one or more kinds of organic solvents can be appropriately selected from those which have been conventionally known as solvents for a chemically amplified resist.

Examples thereof include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether; monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; and aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene.

These solvents can be used individually, or in combination as a mixed solvent.

Among these, propylene glycol monomethyl ether acetate (PGMEA), propylene glycol monomethyl ether (PGME) and ethyl lactate (EL) are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL is mixed as the polar solvent the PGMEA:EL weight ratio is preferably from 1:9 to 9:1, and more preferably from 2:8 to 8:2. Alternatively, when PGME is mixed as the polar solvent, the PGMEA:PGME is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

The amount of the organic solvent is not particularly limited, and is appropriately adjusted to a concentration which enables coating of a coating solution to a substrate, depending on the thickness of the coating film. In general, the organic solvent is used in an amount such that the solid content of the resist composition becomes within the range from 2 to 20% by weight, and preferably from 5 to 15% by weight.

The positive resist composition of the present invention is a novel resist composition which is conventionally unknown.

By using the positive resist composition of the present invention, a resist pattern having reduced line edge roughness (LER) can be formed on a substrate with high resolution.

Here, "LER" refers to the unevenness (roughness) of the side walls of a resist pattern. LER can cause distortions around the holes in a hole pattern, and fluctuations in the line width in line and space patterns, and consequently has the potential to adversely affect the formation of very fine semiconductor elements, and improvement of LER is desired.

The reason why the positive resist composition of the present invention can achieve the above-mentioned effects has not been elucidated yet, but it is presumed as follows. In the structural unit (a0), the side chain portion is long, and an oxygen atom (—O—) which is an electron attracting group is introduced into the side chain portion. As a result, it is presumed that the acid dissociable, dissolution group at the terminal of the side chain of the structural unit (a0) can be easily dissociated, and hence, the dissociation efficiency is improved.

<<Method of Forming a Resist Pattern>>

Next, the method of forming a resist pattern according to the second aspect of the present invention will be described.

The method of forming a resist pattern according to the present invention includes: applying a positive resist composition of the present invention to a substrate to form a resist film on the substrate; conducting exposure of the resist film; and alkali-developing the resist film to form a resist pattern.

More specifically, the method for forming a resist pattern according to the present invention can be performed, for example, as follows. Firstly, a positive resist composition of the present invention is applied onto a substrate using a spinner or the like, and a prebake (post applied bake (PAB)) is conducted under temperature conditions of 80 to 150° C. for 40 to 120 seconds, preferably 60 to 90 seconds to form a resist film. Then, for example, using an ArF exposure apparatus or the like, the resist film is selectively exposed to an ArF excimer laser beam through a desired mask pattern, followed by post exposure bake (PEB) under temperature conditions of 80 to 150° C. for 40 to 120 seconds, preferably 60 to 90 seconds. Subsequently, developing is conducted using an alkali developing solution such as a 0.1 to 10% by weight aqueous solution of tetramethylammonium hydroxide (TMAH), preferably followed by rinsing with pure water, and drying. If desired, bake treatment (post bake) can be conducted following the developing. In this manner, a resist pattern that is faithful to the mask pattern can be obtained.

The substrate is not specifically limited and a conventionally known substrate can be used. For example, substrates for electronic components, and such substrates having wiring patterns formed thereon can be exemplified. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-exemplified substrates provided with an inorganic and/or organic film on the surface thereof may be used. As the inorganic film, an inorganic antireflection film (inorganic BARC) can be exemplified. As the organic film, an organic antireflection film (organic BARC) can be exemplified.

The wavelength to be used for exposure is not particularly limited and the exposure can be conducted using radiations such as ArF excimer laser, KrF excimer laser, $F_2$ excimer laser, extreme ultraviolet rays (EUV), vacuum ultraviolet rays (VUV), electron beam (EB), X-rays, an soft X-rays. The positive resist composition of the present invention is effective to KrF excimer laser, ArF excimer laser, EB and EUV, and particularly effective to ArF excimer laser.

The exposure of the resist film can be either a general exposure (dry exposure) conducted in air or an inert gas such as nitrogen, or immersion exposure (immersion lithography).

In immersion lithography, exposure (immersion exposure) is conducted in a state where the region between the lens and the resist layer formed on a wafer (which was conventionally filled with air or an inert gas such as nitrogen) is filled with a solvent (a immersion medium) that has a larger refractive index than the refractive index of air.

More specifically, in immersion lithography, the region between the resist film formed in the above-described manner and lens at the lowermost portion of the exposure apparatus is filled with a solvent (a immersion medium) that has a larger refractive index than the refractive index of air, and in this state, the resist film is subjected to exposure (immersion exposure) through a desired mask pattern.

The immersion medium preferably exhibits a refractive index larger than the refractive index of air but smaller than the refractive index of the resist film to be subjected to immersion exposure. The refractive index of the immersion medium is not particularly limited as long at it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

EXAMPLES

As follows is a description of examples of the present invention, although the scope of the present invention is by no way limited by these examples.

Example 1

4.8 g of sodium hydride (NaH) was charged into a 1 L three-necked flask. While maintaining the temperature of the three-necked flask at 0° C. in an ice bath, 300 g of tetrahydrofuran (THF) was added, 124 g of a compound (1) was further added while stirring, and stirring was continued for 10 minutes. Then, 30 g of a compound (2) was added while stirring, and a reaction was effected for 12 hours. After the completion of the reaction, the reaction liquid was subjected to suction filtration, and THF was removed from the obtained filtrate by concentration under reduced pressure. Then, water and ethyl acetate was added to the concentrated liquid, and extraction was conducted. The resulting ethyl acetate solution was concentrated under reduced pressure, and purified by column chromatography ($SiO_2$, heptane:ethyl acetate=8:2). The obtained fraction was concentrated and dried under reduced pressure, thereby obtaining 12 g of a compound (3).

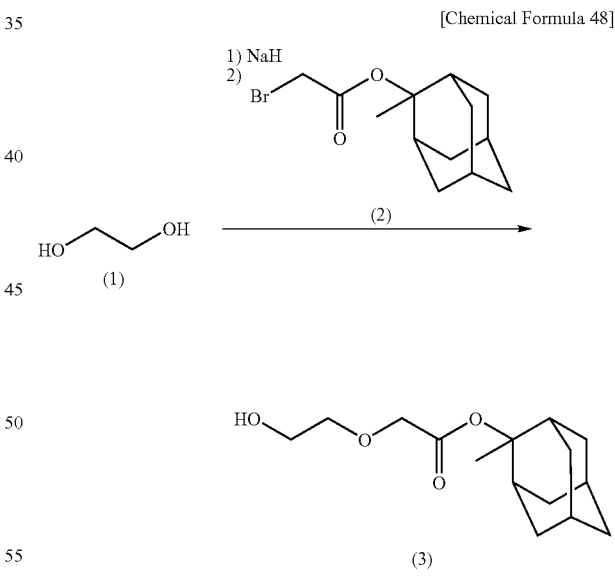

[Chemical Formula 48]

The obtained compound (3) was analyzed by $^1$H-NMR. The results are shown below.

$^1$H-NMR (solvent: $CDCl_3$, 400 MHz): δ(ppm)=4.09(s,2H ($H^a$)), 3.75(t,2H($H^b$)), 3.68(t,2H($H^c$)), 3.03(brs,2H($H^d$)), 1.51-2.35(m,17H($H^e$)).

From the results shown above, it was confirmed that the compound (3) had a structure shown below.

[Chemical Formula 49]

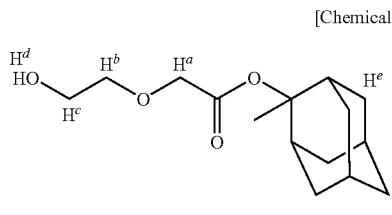

Example 2

5 g of the compound (3), 3.04 g of triethylamine ($Et_3N$) and 10 g of THF were charged into a 300 mL three-necked flask, and stirred for 10 minutes. Then, 2.09 g of a compound (4) and 10 g of THF were added to the three-necked flask, and a reaction was effected at room temperature for 12 hours. After the completion of the reaction, the reaction liquid was subjected to suction filtration, and THF was removed from the obtained filtrate by concentration under reduced pressure. Then, water and ethyl acetate was added to the concentrated liquid, and extraction was conducted. The resulting ethyl acetate solution was concentrated under reduced pressure, and purified by column chromatography ($SiO_2$, heptane:ethyl acetate=8:2). The obtained fraction was concentrated and dried under reduced pressure, thereby obtaining 4.9 g of a compound (5).

[Chemical Formula 50]

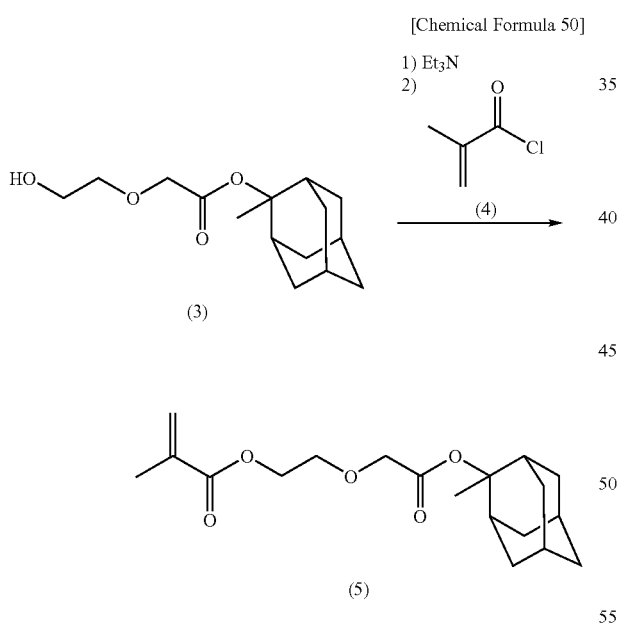

The obtained compound (5) was analyzed by $^1$H-NMR. The results are shown below.

$^1$H-NMR (solvent: $CDCl_3$, 400 MHz): δ(ppm)=6.15(s,1H ($H^a$)), 5.58(s,1H($H^b$)), 4.35(t,2H($H^c$)), 4.08(s,2H($H^d$)), 3.80 (t,2H($H^e$)), 1.51-2.35(m,20H($H^f$)).

From the results shown above, it was confirmed that the compound (5) had a structure shown below.

[Chemical Formula 51]

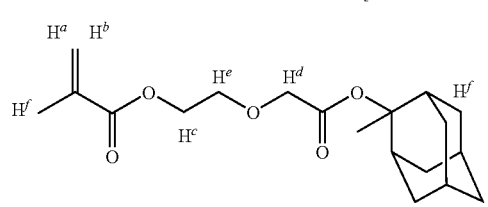

Example 3

4 g of NaH was charged into a 1 L three-necked flask. While maintaining the temperature of the three-necked flask at 0° C. in an ice bath, 100 g of THF was added, 10 g of a compound (6) was further added while stirring, and stirring was continued for 10 minutes. Then, 22.07 g of a compound (2) was added while stirring, and a reaction was effected for 12 hours. After the completion of the reaction, the reaction liquid was subjected to suction filtration, and THF was removed from the obtained filtrate by concentration under reduced pressure. Then, water and ethyl acetate was added to the concentrated liquid, and extraction was conducted. The resulting ethyl acetate solution was concentrated under reduced pressure, and purified by column chromatography ($SiO_2$, heptane:ethyl acetate=8:2). The obtained fraction was concentrated and dried under reduced pressure, thereby obtaining 10 g of a compound (5).

[Chemical Formula 52]

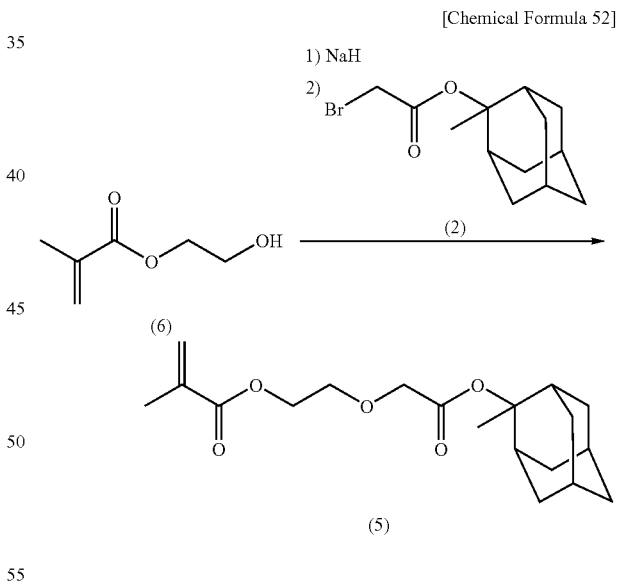

Example 4

Synthesis of Polymeric Compound (1)

1.18 g of a compound (6), 1.90 g of the compound (5) obtained in Example 2 and 0.67 g of a compound (7) were dissolved in 15.00 g of methyl ethyl ketone to obtain a solution. Then, 0.71 mmol of a polymerization initiator (product name: V-601, manufactured by Wako Pure Chemical Industries, Ltd.) was added and dissolved in the obtained solution. The resultant was dropwise added to 6.25 g of methyl ethyl ketone heated to 75° C. in a nitrogen atmosphere over 6 hours. The resulting reaction liquid was heated while stirring for 1 hour, and then cooled to room temperature. Thereafter, the reaction liquid was dropwise added to an excess amount of a methanol/water mixed solution, and an operation to deposit a reaction product was performed three times. The thus obtained reaction product was dried at room temperature under reduced pressure, thereby obtaining a white powder.

[Chemical Formula 53]

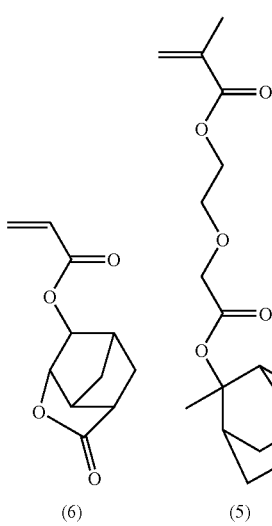

(6)   (5)   (7)

The obtained reaction product was designated as "polymeric compound (1)". The structure of the polymeric compound (1) is shown below.

The polymeric compound (1) was analyzed by carbon 13 nuclear magnetic resonance spectroscopy (600 MHz, $^{13}$C-NMR). As a result, it was found that the composition of the polymer (ratio (molar ratio) of the respective structural units within the structural formula) was l/m/n=38.7/38.0/23.3. Further, with respect to the polymeric compound (1), the weight average molecular weight and the dispersity were determined by the polystyrene equivalent value as measured by gel permeation chromatography (GPC). As a result, it was found that the weight average molecular weight was 23,200, and the dispersity was 2.31. From the results above, it was found that the polymeric compound (1) was a copolymer of the compound (6), the compound (5) and the compound (7).

[Chemical Formula 54]

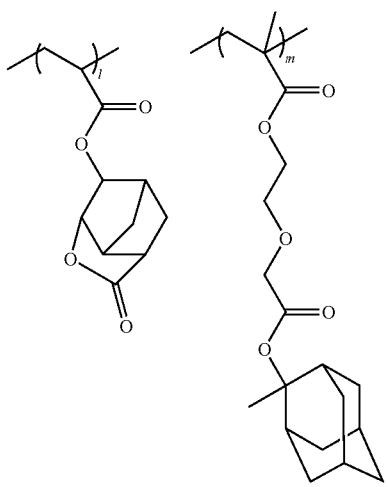

Polymeric compound (1)

Comparative Example 1

Synthesis of Polymeric Compound (2)

4.99 g of the compound (6), 7.00 g of a compound (8) shown below and 1.26 g of the compound (7) were dissolved in 53.00 g of methyl ethyl ketone to obtain a solution. Then, 5.86 mmol of a polymerization initiator (product name: V-601, manufactured by Wako Pure Chemical Industries, Ltd.) was added and dissolved in the obtained solution. The resultant was dropwise added to 22.08 g of methyl ethyl ketone heated to 75° C. in a nitrogen atmosphere over 6 hours. The resulting reaction liquid was heated while stirring for 1 hour, and then cooled to room temperature. Thereafter, the reaction liquid was dropwise added to an excess amount of a methanol/water mixed solution, and an operation to deposit a reaction product was performed three times. The thus obtained reaction product was dried at room temperature under reduced pressure, thereby obtaining a white powder.

[Chemical Formula 55]

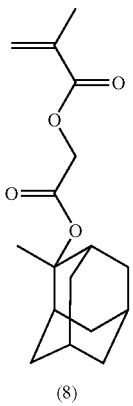

(8)

The obtained reaction product was designated as "polymeric compound (2)". The structure of the polymeric compound (2) is shown below.

The polymeric compound (2) was analyzed by carbon 13 nuclear magnetic resonance spectroscopy (600 MHz, $^{13}$C-NMR). As a result, it was found that the composition of the polymer (ratio (molar ratio) of the respective structural units within the structural formula) was l/m/n=45.0/44.9/10.1. Further, with respect to the polymeric compound (2), the weight average molecular weight and the dispersity were determined by the polystyrene equivalent value as measured by gel permeation chromatography (GPC). As a result, it was found that the weight average molecular weight was 8,400, and the dispersity was 1.96. From the results above, it was found that the polymeric compound (2) was a copolymer of the compound (6), the compound (8) and the compound (7).

[Chemical Formula 56]

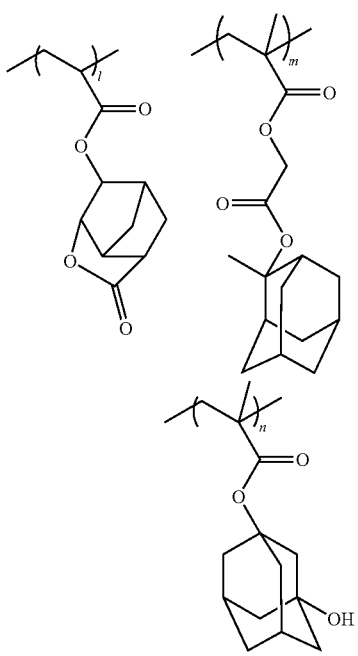

Polymeric compound (2)

Example 5 and Comparative Example 2

The components shown in Table 1 were mixed together and dissolved to obtain positive resist compositions.

TABLE 1

| | Component (A) | Component (B) | Component (D) | Component (S) | |
|---|---|---|---|---|---|
| Ex. 5 | (A)-1 [100] | (B)-1 [4.87] | (D)-1 [0.1] | (S)-1 [1200] | (S)-2 [800] |
| Comp. Ex. 2 | (A)-2 [100] | (B)-1 [4.87] | (D)-1 [0.1] | (S)-1 [1200] | (S)-2 [800] |

In Table 1, the values in brackets [ ] indicate the amount (in terms of parts by weight) of the component added. Further, the reference characters indicate the following.

(A)-1: polymeric compound (1)
(A)-2: polymeric compound (2)
(B)-1: an acid generator represented by chemical formula (B)-1 shown below
(D)-1: tri-n-pentylamine
(S)-1: PGMEA
(S)-2: PGME

[Chemical Formula 57]

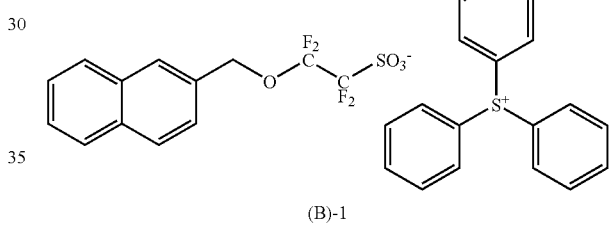

(B)-1

The acid generator (B)-1 was produced as follows. 6.99 g of triphenylsulfoniumbromide was dissolved in 125 ml of pure water to obtain a solution. 5.50 g of a lithium salt of 2-naphthylmethyloxytetrafluoroethanesulfonic acid was added to the obtained solution and stirred at room temperature for 19 hours. Then, 125 g of dichloromethane was added to the resultant, and the organic phase was separated and taken out. The organic phase was washed with 40 ml of pure water, and the organic phase was separated and taken out. The organic phase was concentrated and dried, thereby obtaining the acid generator (B)-1.

Using the obtained positive resist compositions, resist patterns were formed in the following manner, and lithography properties were evaluated.

[Resolution·sensitivity]

An organic anti-reflection film composition (product name: ARC29A, manufactured by Brewer Science Ltd.) was applied onto an 8-inch silicon wafer using a spinner, and the composition was then baked at 205° C. for 60 seconds, thereby forming an organic anti-reflection film having a film thickness of 77 nm. Then, a positive resist composition obtained above was applied onto the anti-reflection film using a spinner, and was then prebaked (PAB) on a hotplate at 110° C. for 60 seconds and dried, thereby forming a resist film having a film thickness of 120 nm.

Subsequently, the resist film was selectively irradiated with an ArF excimer laser (193 nm) through a mask pattern (6% halftone), using an ArF exposure apparatus NSR-S302

(manufactured by Nikon Corporation, NA (numerical aperture)=0.60, ⅔ annular illumination). Thereafter, a post exposure bake (PEB) treatment was conducted at 100° C. for 60 seconds, followed by development for 30 seconds at 23° C. in a 2.38% by weight aqueous solution of tetramethylammonium hydroxide. Then, the resist was washed for 30 seconds with pure water, followed by drying by shaking, thereby forming a resist pattern.

As a result, in each of the examples, a contact hole pattern with a hole diameter of 130 nm and a pitch of 260 nm was formed. The optimum exposure dose (Eop, mJ/cm$^2$) with which the contact hole pattern was formed, i.e., sensitivity, was determined. The results are shown in Table 2.

[Circularity]

Each of the C/H patterns with a hole diameter of 130 nm and a pitch of 260 nm formed was observed from the upper side thereof using a scanning electron microscope, and the circularity was evaluated with the following criteria. The results are shown in Table 2.

TABLE 2

| | Eop (mJ/cm$^2$) | Circularity |
|---|---|---|
| Ex. 5 | 26.3 | ○ |
| Comp. Ex. 2 | 29.7 | Δ |

○: high circularity
Δ: low circularity

As shown by the results above, in Example 5, the circularity of the hole pattern was high, and sensitivity was excellent.

Example 6

Synthesis of Polymeric Compound (3)

6.19 g (29.76 mmol) of the compound (6), 10.00 g (29.76 mmol) of the compound (5) and 3.51 g (14.88 mmol) of the compound (7) were dissolved in 78.80 g of methyl ethyl ketone to obtain a solution. Then, 11.16 mmol of a polymerization initiator (product name: V-601, manufactured by Wako Pure Chemical Industries, Ltd.) was added and dissolved in the obtained solution. The resultant was dropwise added to 32.83 g of methyl ethyl ketone heated to 75° C. in a nitrogen atmosphere over 6 hours. The resulting reaction liquid was heated while stirring for 1 hour, and then cooled to room temperature.

The obtained polymer solution (reaction liquid) was concentrated to a solid content of 30% by weight, and dropwise added to 370 ml of n-heptane at room temperature to deposit a copolymer. Then, 66 g of a THF solution of the copolymer was prepared, and the THF solution was dropwise added to 370 ml of n-heptane to deposit a copolymer.

The copolymer was dispersed in a mixed solution of methanol/water=60/40 (volume ratio) to wash the copolymer, and then, the copolymer was dispersed in a mixed solution of methanol/water=70/30 (volume ratio) to wash the copolymer. Thereafter, the copolymer was recovered by filtration.

The thus obtained copolymer was dried at 40° C. for 3 days, thereby obtaining 13.0 g of a white powder (yield: 66%).

The obtained copolymer was designated as "polymeric compound (3)". The structure of the polymeric compound (3) is shown below. The polymeric compound (3) was analyzed by carbon 13 nuclear magnetic resonance spectroscopy (600 MHz, $^{13}$C-NMR). As a result, it was found that the composition of the polymer (ratio (molar ratio) of the respective structure units within the structural formula) was l/m/n=40.4/39.1/20.5. Further, with respect to the polymeric compound (3), the weight average molecular weight and the dispersity were determined by the polystyrene equivalent value as measured by gel permeation chromatography (GPC). As a result, it was found that the weight average molecular weight was 8,700, and the dispersity was 2.18.

From the results above, it was found that the polymeric compound (3) was a copolymer of the compound (6), the compound (5) and the compound (7).

[Chemical Formula 58]

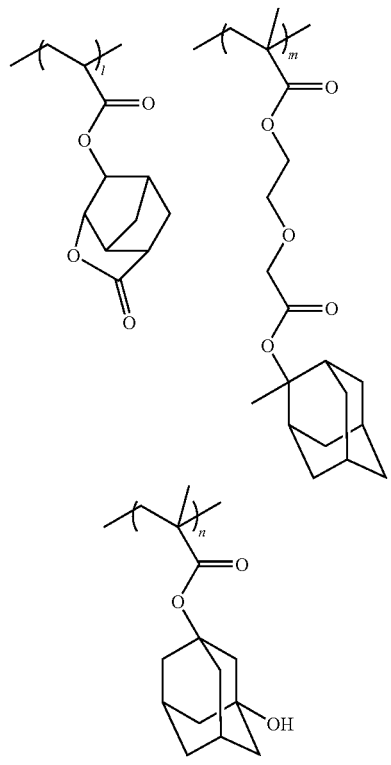

Polymeric compound (3)

Example 7

Synthesis of Polymeric Compound (4)

6.19 g (29.76 mmol) of the compound (6), 10.00 g (29.76 mmol) of the compound (5) and 3.51 g (14.88 mmol) of the compound (7) were dissolved in 78.80 g of methyl ethyl ketone to obtain a solution. Then, 13.39 mmol of a polymerization initiator (product name: V-601, manufactured by Wako Pure Chemical Industries, Ltd.) was added and dissolved in the obtained solution. The resultant was dropwise added to 32.83 g of methyl ethyl ketone heated to 75° C. in a nitrogen atmosphere over 6 hours. The resulting reaction liquid was heated while stirring for 1 hour, and then cooled to room temperature.

The obtained polymer solution (reaction liquid) was concentrated to a solid content of 30% by weight, and dropwise added to 370 ml of n-heptane at room temperature to deposit a copolymer. Then, 66 g of a THF solution of the copolymer was prepared, and the THF solution was dropwise added to 370 ml of n-heptane to deposit a copolymer.

The copolymer was dispersed in a mixed solution of methanol/water=60/40 (volume ratio) to wash the copolymer, and then, the copolymer was dispersed in a mixed solution of methanol/water=70/30 (volume ratio) to wash the copolymer. Thereafter, the copolymer was recovered by filtration.

The thus obtained copolymer was dried at 40° C. for 3 days, thereby obtaining 14.9 g of a white powder (yield: 76%).

The obtained copolymer was designated as "polymeric compound (4)". The structure of the polymeric compound (4) is shown below. The polymeric compound (4) was analyzed by carbon 13 nuclear magnetic resonance spectroscopy (600 MHz, $^{13}$C-NMR). As a result, it was found that the composition of the polymer (ratio (molar ratio) of the respective structural units within the structural formula) was l/m/a=42.4/37.2/19.9. Further, with respect to the polymeric compound (4), the weight average molecular weight and the dispersity were determined by the polystyrene equivalent value as measured by gel permeation chromatography (GPC). As a result, it was found that the weight average molecular weight was 6,400, and the dispersity was 1.80.

From the results above, it was found that the polymeric compound (4) was a copolymer of the compound (6), the compound (5) and the compound (7).

[Chemical Formula 59]

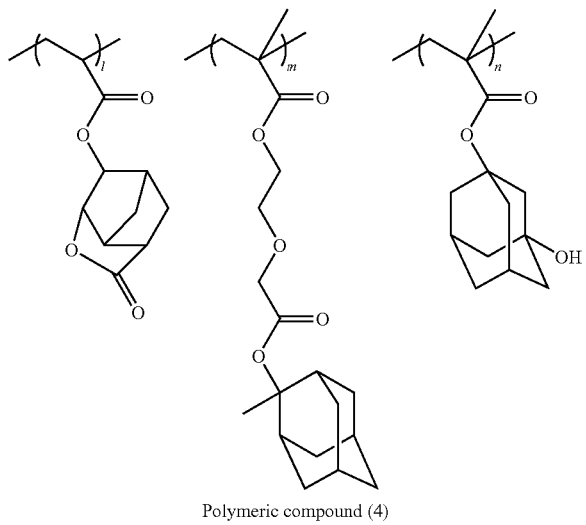

Polymeric compound (4)

Example 8

Synthesis of Polymeric Compound (5)

3.94 g (18.94 mmol) of the compound (6), 10.00 g (29.76 mmol) of the compound (5) and 4.47 g (18.94 mmol) of the compound (7) were dissolved in 73.64 g of methyl ethyl ketone to obtain a solution. Then, 12.17 mmol of a polymerization initiator (product name: V-601, manufactured by Wako Pure Chemical Industries, Ltd.) was added and dissolved in the obtained solution. The resultant was dropwise added to 30.68 g of methyl ethyl ketone heated to 75° C. in a nitrogen atmosphere over 6 hours. The resulting reaction liquid was heated while stirring for 1 hour, and then cooled to room temperature.

The obtained polymer solution (reaction liquid) was concentrated to a solid content of 30% by weight, and dropwise added to 340 ml of n-heptane at room temperature to deposit a copolymer. Then, 61 g of a THF solution of the copolymer was prepared, and the THF solution was dropwise added to 340 ml of n-heptane to deposit a copolymer.

The copolymer was dispersed in a mixed solution of methanol/water=60/40 (volume ratio) to wash the copolymer, and then, the copolymer was dispersed in a mixed solution of methanol/water=70/30 (volume ratio) to wash the copolymer. Thereafter, the copolymer was recovered by filtration.

The thus obtained copolymer was dried at 40° C. for 3 days, thereby obtaining 13.8 g of a white powder (yield: 75%).

The obtained copolymer was designated as "polymeric compound (5)". The structure of the polymeric compound (5) is shown below. The polymeric compound (5) was analyzed by carbon 13 nuclear magnetic resonance spectroscopy (600 MHz, $^{13}$C-NMR). As a result, it was found that the composition of the polymer (ratio (molar ratio) of the respective structural units within the structural formula) was l/m/n=30.5/39.0/30.5. Further, with respect to the polymeric compound (5), the weight average molecular weight and the dispersity were determined by the polystyrene equivalent value as measured by gel permeation chromatography (GPC). As a result, it was found that the weight average molecular weight was 6,700, and the dispersity was 1.99.

From the results above, it was found that the polymeric compound (5) was a copolymer of the compound (6), the compound (5) and the compound (7).

[Chemical Formula 60]

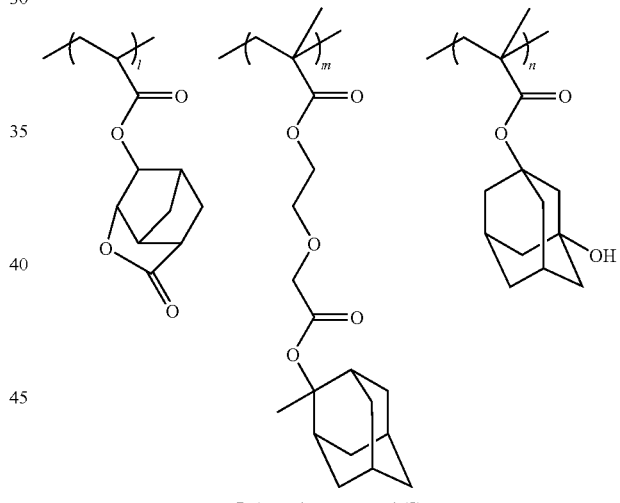

Polymeric compound (5)

Example 9

Synthesis of Polymeric Compound (6)

4.99 g (23.99 mmol) of the compound (6), 7.00 g (20.83 mmol) of the compound (5) and 4.32 g (18.31 mmol) of the compound (7) were dissolved in 65.24 g of methyl ethyl ketone to obtain a solution. Then, 11.68 mol of a polymerization initiator (product name: V-601, manufactured by Wako Pure Chemical Industries, Ltd.) was added and dissolved in the obtained solution. The resultant was dropwise added to 27.18 g of methyl ethyl ketone heated to 75° C. in a nitrogen atmosphere over 6 hours. The resulting reaction liquid was heated while stirring for 1 hour, and then cooled to room temperature.

The obtained polymer solution (reaction liquid) was concentrated to a solid content of 30% by weight and dropwise added to 320 ml of n-heptane at room temperature to deposit a copolymer. Then, 54 g of a THF solution of the copolymer was prepared, and the THF solution was dropwise added to 320 ml of n-heptane to deposit a copolymer.

The copolymer was dispersed in a mixed solution of methanol/water=60/40 (volume ratio) to wash the copolymer, and then, the copolymer was dispersed in a mixed solution of methanol/water=70/30 (volume ratio) to wash the copolymer. Thereafter, the copolymer was recovered by filtration.

The thus obtained copolymer was dried at 40° C. for 3 days, thereby obtaining 12.0 g of a white powder (yield: 74%).

The obtained copolymer was designated as "polymeric compound (6)". The structure of the polymeric compound (6) is shown below. The polymeric compound (6) was analyzed by carbon 13 nuclear magnetic resonance spectroscopy (600 MHz, $^{13}$C-NMR). As a result, it was found that the composition of the polymer (ratio (molar ratio) of the respective structural units within the structural formula) was l/m/n=43.2/29.9/26.9. Further, with respect to the polymeric compound (6), the weight average molecular weight and the dispersity were determined by the polystyrene equivalent value as measured by gel permeation chromatography (GPC). As a result, it was found that the weight average molecular weight was 7,500, and the dispersity was 2.24.

From the results above, it was found that the polymeric compound (6) was a copolymer of the compound (6), the compound (5) and the compound (7).

[Chemical Formula 61]

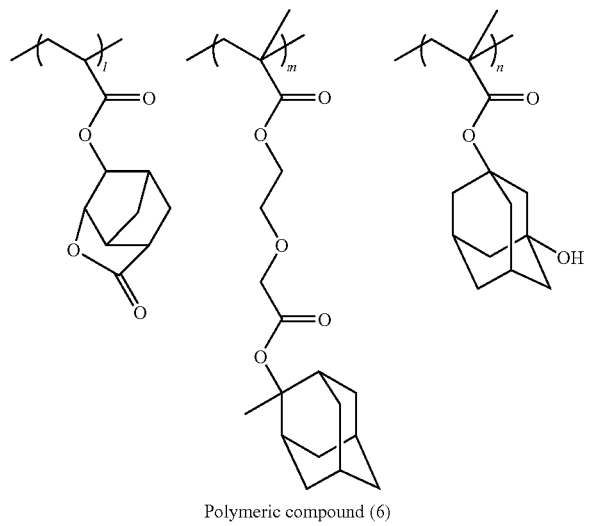

Polymeric compound (6)

Example 10

Synthesis of Polymeric Compound (7)

6.30 g (30.30 mmol) of the compound (6), 7.00 g (20.83 mmol) of the compound (5) and 2.83 g (11.99 mmol) of the compound (7) were dissolved in 64.52 g of methyl ethyl ketone to obtain a solution. Then, 11.68 mmol of a polymerization initiator (product name: V-601, manufactured by Wako Pure Chemical Industries, Ltd.) was added and dissolved in the obtained solution. The resultant was dropwise added to 26.88 g of methyl ethyl ketone heated to 75° C. in a nitrogen atmosphere over 6 hours. The resulting reaction liquid was heated while stirring for 1 hour, and then cooled to room temperature.

The obtained polymer solution (reaction liquid) was concentrated to a solid content of 30% by weight, and dropwise added to 320 ml of n-heptane at room temperature to deposit a copolymer. Then, 54 g of a THF solution of the copolymer was prepared, and the THF solution was dropwise added to 320 ml of n-heptane to deposit a copolymer.

The copolymer was dispersed in a mixed solution of methanol/water=60/40 (volume ratio) to wash the copolymer, and then, the copolymer was dispersed in a mixed solution of methanol/water=70/30 (volume ratio) to wash the copolymer. Thereafter, the copolymer was recovered by filtration.

The thus obtained copolymer was dried at 40° C. for 3 days, thereby obtaining 12.0 g of a white powder (yield: 74%).

The obtained copolymer was designated as "polymeric compound (7)". The structure of the polymeric compound (7) is shown below. The polymeric compound (7) was analyzed by carbon 13 nuclear magnetic resonance spectroscopy (600 MHz, $^{13}$C-NMR). As a result, it was found that the composition of the polymer (ratio (molar ratio) of the respective structural units within the structural formula) was l/m/n=52.6/27.5/19.9. Further, with respect to the polymeric compound (7), the weight average molecular weight and the dispersity were determined by the polystyrene equivalent value as measured by gel permeation chromatography (GPC). As a result, it was found that the weight average molecular weight was 5,300, and the dispersity was 1.97.

From the results above, it was found that the polymeric compound (7) was a copolymer of the compound (6), the compound (5) and the compound (7).

[Chemical Formula 62]

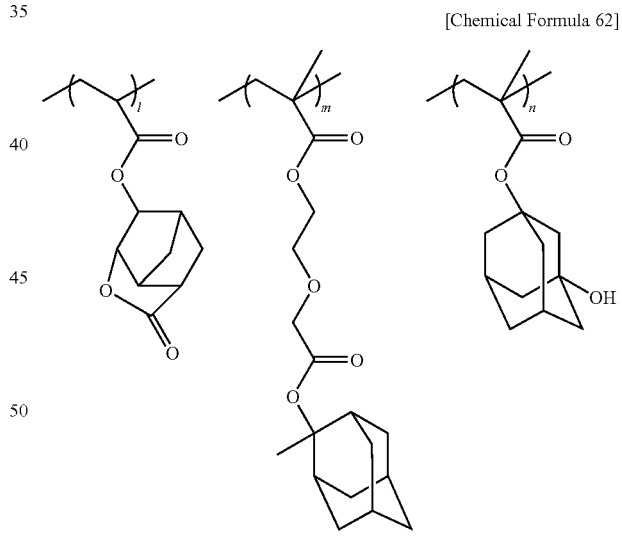

Polymeric compound (7)

Example 11

Synthesis of Polymeric Compound (8)

2.94 g (13.26 mmol) of a compound (9) shown below, 7.00 g (20.83 mmol) of the compound (5) and 3.13 g (13.26 mmol) of the compound (7) were dissolved in 51.56 g of methyl ethyl ketone to obtain a solution. Then, 8.76 mmol of a polymerization initiator (product name: V-601, manufactured by Wako Pure Chemical Industries, Ltd.) was added and dissolved in the obtained solution. The resultant was dropwise added to 21.48 g of methyl ethyl ketone heated to 75° C. in a nitrogen atmosphere over 6 hours. The resulting reaction liquid was heated while stirring for 1 hour, and then cooled to room temperature.

The obtained polymer solution (reaction liquid) was concentrated to a solid content of 30% by weight, and dropwise added to 250 ml of n-heptane at room temperature to deposit a copolymer. Then, 44 g of a THF solution of the copolymer was prepared, and the THF solution was dropwise added to 250 ml of n-heptane to deposit a copolymer.

The copolymer was dispersed in a mixed solution of methanol/water=60/40 (volume ratio) to wash the copolymer, and then, the copolymer was dispersed in a mixed solution of methanol/water=70/30 (volume ratio) to wash the copolymer. Thereafter, the copolymer was recovered by filtration.

The thus obtained copolymer was dried at 40° C. for 3 days, thereby obtaining 9.3 g of a white powder (yield: 71%).

[Chemical Formula 63]

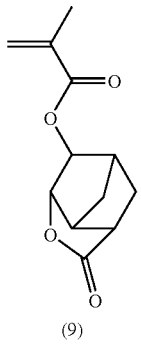

(9)

The obtained copolymer was designated as "polymeric compound (8)". The structure of the polymeric compound (8) is shown below. The polymeric compound (8) was analyzed by carbon 13 nuclear magnetic resonance spectroscopy (600 MHz, $^{13}$C-NMR). As a result, it was found that the composition of the polymer (ratio (molar ratio) of the respective structural units within the structural formula) was l/m/n=31.5/38.3/30.2. Further, with respect to the polymeric compound (8), the weight average molecular weight and the dispersity were determined by the polystyrene equivalent value as measured by gel permeation chromatography (GPC). As a result, it was found that the weight average molecular weight was 7,900, and the dispersity was 2.13.

From the results above, it was found that the polymeric compound (8) was a copolymer of the compound (9), the compound (5) and the compound (7).

[Chemical Formula 64]

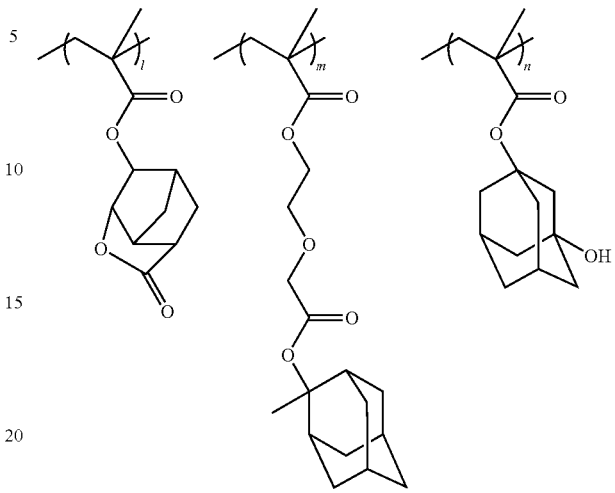

Polymeric compound (8)

Example 12

Synthesis of Polymeric Compound (9)

2.94 g (13.26 mmol) of a compound (10) shown below, 7.00 g (20.83 mmol) of the compound (5) and 3.13 g (13.26 mmol) of the compound (7) were dissolved in 19.61 g of ethyl lactate to obtain a solution. Then, 3.3 mmol of a polymerization initiator product name: V-601, manufactured by Wako Pure Chemical Industries, Ltd.) was added and dissolved in the obtained solution. The resultant was dropwise added to 10.89 g of ethyl lactate heated to 80° C. in a nitrogen atmosphere over 6 hours. The resulting reaction liquid was heated while stirring for 1 hour, and then cooled to room temperature.

The obtained polymer solution (reaction liquid) was dropwise added to 250 ml of n-heptane at room temperature to deposit a copolymer. Then, 44 g of a THF solution of the copolymer was prepared, and the THF solution was dropwise added to 250 ml of n-heptane to deposit a copolymer.

The copolymer was dispersed in a mixed solution of methanol/water=60/40 (volume ratio) to wash the copolymer, and then, the copolymer was dispersed in a mixed solution of methanol/water=70/30 (volume ratio) to wash the copolymer. Thereafter, the copolymer was recovered by filtration.

The thus obtained copolymer was dried at 40° C. for 3 days, thereby obtaining 9.5 g of a white powder (yield: 73%).

[Chemical Formula 65]

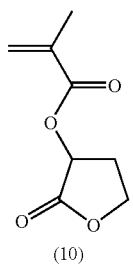

(10)

The obtained copolymer was designated as "polymeric compound (9)". The structure of the polymeric compound (9) is shown below. The polymeric compound (9) was analyzed by carbon 13 nuclear magnetic resonance spectroscopy (600 MHz, $^{13}$C-NMR). As a result, it was found that the composition of the polymer (ratio (molar ratio) of the respective structural units within the structural formula) was l/m/n=31.4/38.4/30.2. Further, with respect to the polymeric compound (9), the weight average molecular weight and the dispersity were determined by the polystyrene equivalent value as measured by gel permeation chromatography (GPC). As a result, it was found that the weight average molecular weight was 7,800, and the dispersity was 2.01.

From the results above, it was found that the polymeric compound (9) was a copolymer of the compound (10), the compound (5) and the compound (7).

The obtained copolymer was designated as "polymeric compound (10)". The structure of the polymeric compound (10) is shown below. The polymeric compound (10) was analyzed by carbon 13 nuclear magnetic resonance spectroscopy (600 MHz, $^{13}$C-NMR). As a result, it was found that the composition of the polymer (ratio (molar ratio) of the respective structural units within the structural formula) was l/m/n=51.6/28.5/19.9. Further, with respect to the polymeric compound (10), the weight average molecular weight and the dispersity were determined by the polystyrene equivalent value as measured by gel permeation chromatography (GPC). As a result, it was found that the weight average molecular weight was 7,300, and the dispersity was 2.07.

From the results above, it was found that the polymeric compound (10) was a copolymer of the compound (10), the compound (5) and the compound (7).

[Chemical Formula 66]

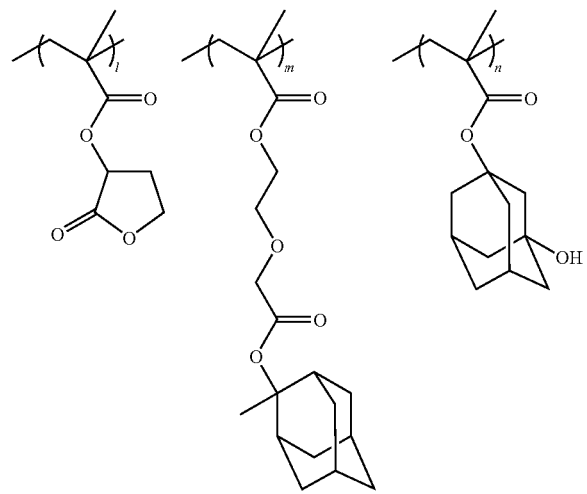

Polymeric compound (9)

[Chemical Formula 67]

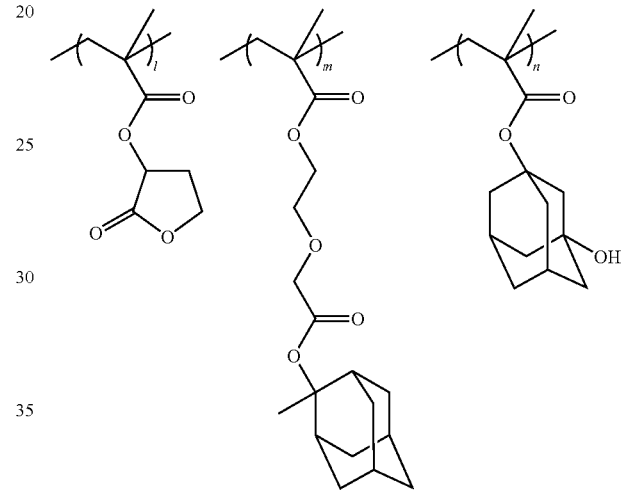

Polymeric compound (10)

Example 13

Synthesis of Polymeric Compound (10)

6.30 g (30.30 mmol) of the compound (10), 7.00 g (20.83 mmol) of the compound (5) and 2.83 g (11.99 mmol) of the compound (7) were dissolved in 24.20 g of ethyl lactate to obtain a solution. Then, 4.5 mmol of a polymerization initiator (product name: V-601, manufactured by Wako Pure Chemical Industries, Ltd.) was added and dissolved in the obtained solution. The resultant was dropwise added to 13.44 g of ethyl lactate heated to 80° C. in a nitrogen atmosphere over 6 hours. The resulting reaction liquid was heated while stirring for 1 hour, and then cooled to room temperature.

The obtained polymer solution (reaction liquid) was dropwise added to 320 ml of n-heptane at room temperature to deposit a copolymer. Then, 54 g of a THF solution of the copolymer was prepared, and the THF solution was dropwise added to 320 ml of n-heptane to deposit a copolymer.

The copolymer was dispersed in a mixed solution of methanol/water=60/40 (volume ratio) to wash the copolymer, and then, the copolymer was dispersed in a mixed solution of methanol/water=70/30 (volume ratio) to wash the copolymer. Thereafter, the copolymer was recovered by filtration.

The thus obtained copolymer was dried at 40° C. for 3 days, thereby obtaining 12.0 g of a white powder (yield: 74%).

Example 14

Synthesis of Polymeric Compound (11)

4.99 g (23.99 mmol) of the compound (10), 7.00 g (20.83 mmol of the compound (5) and 4.32 g (18.31 mmol) of the compound (7) were dissolved in 24.47 g of ethyl lactate to obtain a solution. Then, 4.4 mmol of a polymerization initiator (product name: V-601, manufactured by Wako Pure Chemical Industries, Ltd.) was added and dissolved in the obtained solution. The resultant was dropwise added to 13.59 g of ethyl lactate treated to 80° C. in a nitrogen atmosphere over 6 hours. The resulting reaction liquid was heated while stirring for 1 hour, and then cooled to room temperature.

The obtained polymer solution (reaction liquid) was dropwise added to 320 ml of n-heptane at room temperature to deposit a copolymer. Then, 54 g of a THF solution of the copolymer was prepared, and the THF solution was dropwise added to 320 ml of n-heptane to deposit a copolymer.

The copolymer was dispersed in a mixed solution of methanol/water=60/40 (volume ratio) to wash the copolymer, and then, the copolymer was dispersed in a mixed solution of methanol/water=70/30 (volume ratio) to wash the copolymer. Thereafter, the copolymer was recovered by filtration.

The thus obtained copolymer was dried at 40° C. for 3 days, thereby obtaining 12.0 g of a white powder (yield: 74%).

The obtained copolymer was designated as "polymeric compound (11)". The structure of the polymeric compound (11) is shown below. The polymeric compound (11) was analyzed by carbon 13 nuclear magnetic resonance spectroscopy (600 MHz, $^{13}$C-NMR). As a result, it was found that the composition of the polymer (ratio (molar ratio) of the respective structural units within the structural formula) was l/m/n=42.2/30.9/26.9. Further, with respect to the polymeric compound (11), the weight average molecular weight and the dispersity were determined by the polystyrene equivalent value as measured by gel permeation chromatography (GPC). As a result, it was found that the weight average molecular weight was 7,600, and the dispersity was 2.14.

From the results above, it was found that the polymeric compound (11) was a copolymer of the compound (10), the compound (5) and the compound (7).

The obtained copolymer was designated as "polymeric compound (12)". The structure of the polymeric compound (12) is shown below. The polymeric compound (12) was analyzed by carbon 13 nuclear magnetic resonance spectroscopy (600 MHz, $^{13}$C-NMR). As a result, it was found that the composition of the polymer (ratio (molar ratio) of the respective structure units within the structural formula) was l/m/n=40.4/40.1/19.5. Further, with respect to the polymeric compound (12), the weight average molecular weight and the dispersity were determined by the polystyrene equivalent value as measured by gel permeation chromatography (GPC). As a result, it was found that the weight average molecular weight was 7,700, and the dispersity was 2.11. From the results above, it was found at the polymeric compound (12) was a copolymer of the compound (10), the compound (5) and the compound (7).

[Chemical Formula 68] [Chemical Formula 69]

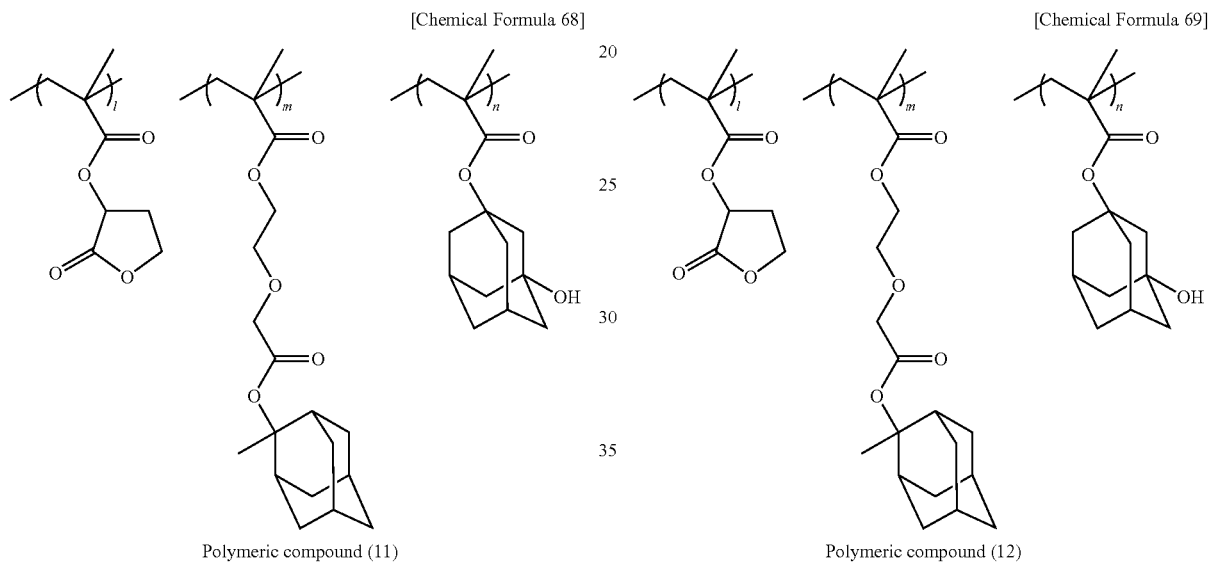

Polymeric compound (11)

Polymeric compound (12)

Example 15

Synthesis of Polymeric Compound (12)

6.19 g (29.76 mmol) of the compound (10), 10.00 g (29.76 mmol) of the compound (5) and 3.51 g (14.88 mmol) of the compound (7) were dissolved in 29.55 g of ethyl lactate to obtain a solution. Then, 5.2 mmol of a polymerization initiator (product name: V-601, manufactured by Wako Pure Chemical Industries, Ltd.) was added and dissolved in the obtained solution. The resultant was dropwise added to 16.42 g of ethyl lactate heated to 80° C. in a nitrogen atmosphere over 6 hours. The resulting reaction liquid was heated while stirring for 1 hour, and then cooled to room temperature.

The obtained polymer solution (reaction liquid) was dropwise added to 370 ml of n-heptane at room temperature to deposit a copolymer. Then, 66 g of a THF solution of the copolymer was prepared, and the THF solution was dropwise added to 370 ml of n-heptane to deposit a copolymer.

The copolymer was dispersed in a mixed solution of methanol/water=60/40 (volume ratio) to wash the copolymer, and then, the copolymer was dispersed in a mixed solution of methanol/water=70/30 (volume ratio) to wash the copolymer. Thereafter, the copolymer was recovered by filtration.

The thus obtained copolymer was dried at 40° C. for 3 days, thereby obtaining 14.8 g of a white powder (yield: 75%).

Example 16

Synthesis of Polymeric Compound (13)

2.94 g (13.26 mmol) of a compound (11) shown below, 7.00 g (20.83 mmol) of the compound (5) and 3.13 g (13.26 mmol) of the compound (7) were dissolved in 19.61 g of ethyl lactate to obtain a solution. Then, 3.3 mmol of a polymerization initiator (product name: V-601, manufactured by Wako Pure Chemical Industries, Ltd.) was added and dissolved in the obtained solution. The resultant was dropwise added to 10.89 g of ethyl lactate heated to 80° C. in a nitrogen atmosphere over 6 hours. The resulting reaction liquid was heated while stirring for 1 hour, and then cooled to room temperature.

The obtained polymer solution (reaction liquid) was dropwise added to 250 ml of n-heptane at room temperature to deposit a copolymer. Then, 44 g of a THF solution of the copolymer was prepared, and the THF solution was dropwise added to 250 ml of n-heptane to deposit a copolymer.

The copolymer was dispersed in a mixed solution of methanol/water=60/40 (volume ratio) to wash the copolymer, and then, the copolymer was dispersed in a mixed solution of methanol/water=70/30 (volume ratio) to wash the copolymer. Thereafter, the copolymer was recovered by filtration.

The thus obtained copolymer was dried at 40° C. for 3 days, thereby obtaining 9.1 g of a white powder (yield: 70%).

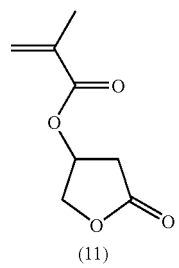

[Chemical Formula 70]

(11)

The obtained copolymer was designated as "polymeric compound (13)". The structure of the polymeric compound (13) is shown below. The polymeric compound (13) was analyzed by carbon 13 nuclear magnetic resonance spectroscopy (600 MHz, $^{13}$C-NMR). As a result, it was found that the composition of the polymer (ratio (molar ratio) of the respective structural units within the structural formula) was l/m/n=31.0/39.4/29.6. Further, with respect to the polymeric compound (13), the weight average molecular weight and the dispersity were determined by the polystyrene equivalent value as measured by gel permeation chromatography (GPC). As a result, it was found that the weight average molecular weight was 7,700, and the dispersity was 2.06. From the results above, it was found that the polymeric compound (13) was a copolymer of the compound (11), the compound (5) and the compound (7).

[Chemical Formula 71]

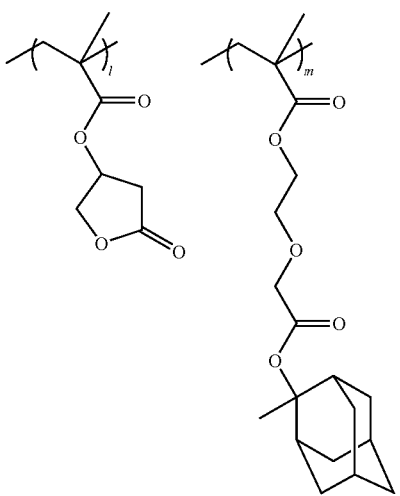

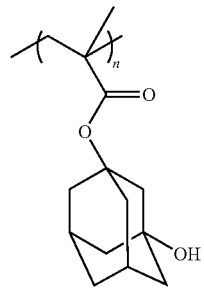

Polymeric compound (13)

Example 17

Synthesis of Polymeric Compound (14)

6.30 g (30.30 mmol) of the compound (11), 7.00 g (20.83 mmol) of the compound (5) and 2.83 g (11.99 mmol) of the compound (7) were dissolved in 24.20 g of ethyl lactate to obtain a solution. Then, 4.5 mmol of a polymerization initiator (product name: V-601, manufactured by Wako Pure Chemical Industries, Ltd.) was added and dissolved in the obtained solution. The resultant was dropwise added to 13.44 g of ethyl lactate heated to 80° C. in a nitrogen atmosphere over 6 hours. The resulting reaction liquid was heated while stirring for 1 hour, and then cooled to room temperature.

The obtained polymer solution (reaction liquid) was dropwise added to 320 ml of n-heptane at room temperature to deposit a copolymer. Then, 54 g of a THF solution of the copolymer was prepared and the THF solution was dropwise added to 320 ml of n-heptane to deposit a copolymer.

The copolymer was dispersed in a mixed solution of methanol/water 60/40 (volume ratio) to wash the copolymer, and then, the copolymer was dispersed in a mixed solution of methanol/water=70/30 (volume ratio) to wash the copolymer. Thereafter, the copolymer was recovered by filtration.

The thus obtained copolymer was dried at 40° C. for 3 days, thereby obtaining 12.2 g of a white powder (yield: 76%).

The obtained copolymer was designated as "polymeric compound (14)". The structure of the polymeric compound (14) is shown below. The polymeric compound (14) was analyzed by carbon 13 nuclear magnetic resonance spectroscopy (600 MHz, $^{13}$C-NMR). As a result, it was found that the composition of the polymer (ratio (molar ratio) of the respective structural units within the structural formula) was l/m/n=51.9/28.8/19.3. Further with respect to the polymeric compound (14), the weight average molecular weight and the dispersity were determined by the polystyrene equivalent value as measured by gel permeation chromatography (GPC). As a result, it was found that the weight average molecular weight was 7,300, and the dispersity was 2.07. From the results above, it was found that the polymeric compound (14) was a copolymer of the compound (11), the compound (5) and the compound (7).

[Chemical Formula 72]

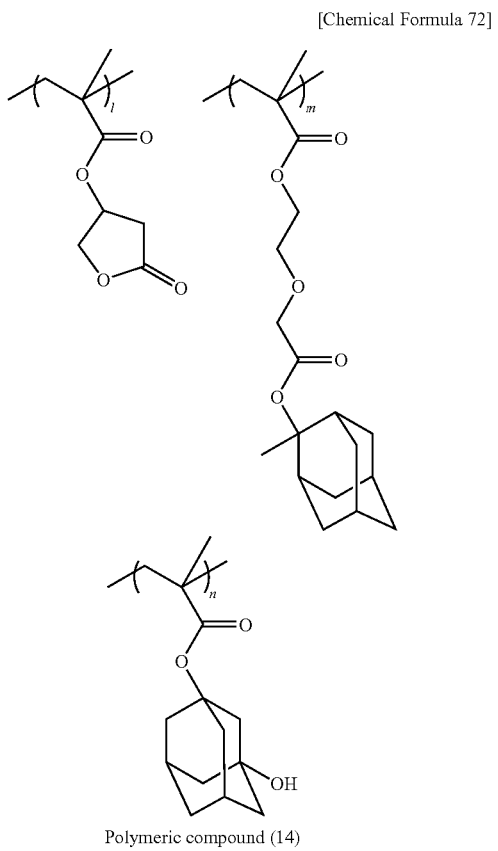

Polymeric compound (14)

Example 18

Synthesis of Polymeric Compound (15)

4.99 g (23.99 mmol) of the compound (11), 7.00 g (20.83 mmol) of the compound (5) and 4.32 g (18.31 mmol) of the compound (7) were dissolved in 24.47 g of ethyl lactate to obtain a solution. Then, 4.4 mmol of a polymerization initiator (product name: V-601, manufactured by Wako Pure Chemical Industries, Ltd.) was added and dissolved in the obtained solution. The resultant was dropwise added to 13.59 g of ethyl lactate heated to 80° C. in a nitrogen atmosphere over 6 hours. The resulting reaction liquid was heated while stirring for 1 hour, and then cooled to room temperature.

The obtained polymer solution (reaction liquid) was dropwise added to 320 ml of n-heptane at room temperature to deposit a copolymer. Then, 54 g of a THF solution of the copolymer was prepared, and the THF solution was dropwise added to 320 ml of n-heptane to deposit a copolymer.

The copolymer was dispersed in a mixed solution of methanol/water=60/40 (volume ratio) to wash the copolymer, and then, the copolymer was dispersed in a mixed solution of methanol/water=70/30 (volume ratio) to wash the copolymer. Thereafter, the copolymer was recovered by filtration.

The thus obtained copolymer was dried at 40° C. for 3 days, thereby obtaining 11.6 g of a white powder (yield: 71%).

The obtained copolymer was designated as "polymeric compound (15)". The structure of the polymeric compound (15) is shown below. The polymeric compound (15) was analyzed by carbon 13 nuclear magnetic resonance spectroscopy (600 MHz, $^{13}$C-NMR). As a result, it was found that the composition of the polymer (ratio (molar ratio) of the respective structural units within the structural formula) was l/m/n=42.8/30.4/26.8. Further, with respect to the polymeric compound (15), the weight average molecular weight and the dispersity were determined by the polystyrene equivalent value as measured by gel permeation chromatography (GPC). As a result, it was found that the weight average molecular weight was 7,200, and the dispersity was 2.18. From the results above, it was found that the polymeric compound (15) was a copolymer of the compound (11), the compound (5) and the compound (7).

[Chemical Formula 73]

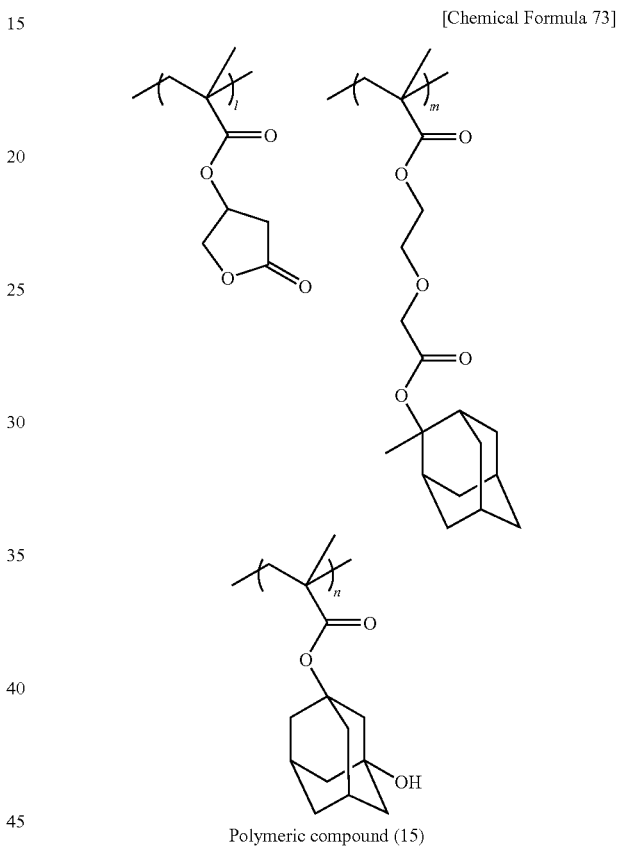

Polymeric compound (15)

Example 19

Synthesis of Polymeric Compound (16)

6.19 g (29.76 mmol) of the compound (11), 10.00 g (29.76 mmol) of the compound (5) and 3.51 g (14.88 mmol) of the compound (7) were dissolved in 29.55 g of ethyl lactate to obtain a solution. Then, 5.2 mmol of a polymerization initiator (product name: V-601, manufactured by Wako Pure Chemical Industries, Ltd.) was added and dissolved in the obtained solution. The resultant was dropwise added to 16.42 g of ethyl lactate heated to 80° C. in a nitrogen atmosphere over 6 hours. The resulting reaction liquid was heated while stirring for 1 hour, and then cooled to room temperature.

The obtained polymer solution (reaction liquid) was dropwise added to 370 ml of n-heptane at room temperature to deposit a copolymer. Then, 66 g of a THF solution of the copolymer was prepared, and the THF solution was dropwise added to 370 ml of n-heptane to deposit a copolymer.

The copolymer was dispersed in a mixed solution of methanol/water=60/40 (volume ratio) to wash the copolymer, and then, the copolymer was dispersed in a mixed solution of methanol/water=70/30 (volume ratio) to wash the copolymer. Thereafter, the copolymer was recovered by filtration.

The thus obtained copolymer was dried at 40° C. for 3 days, thereby obtaining 13.8 g of a white powder (yield: 70%).

The obtained copolymer was designated as "polymeric compound (16)". The structure of the polymeric compound (16) is shown below. The polymeric compound (16) was analyzed by carbon 13 nuclear magnetic resonance spectroscopy (600 MHz, $^{13}$C-NMR). As a result, it was found that the composition of the polymer (ratio (molar ratio) of the respective structural units within the structural formula) was l/m/n=40.9/39.8/19.3. Further, with respect to the polymeric compound (16), the weight average molecular weight and the dispersity were determined by the polystyrene equivalent value as measured by gel permeation chromatography (GPC). As a result, it was found that the weight average molecular weight was 7,700, and the dispersity was 2.11. From the results above, it was found that the polymeric compound (16) was a copolymer of the compound (11), the compound (5) and the compound (7).

[Chemical Formula 74]

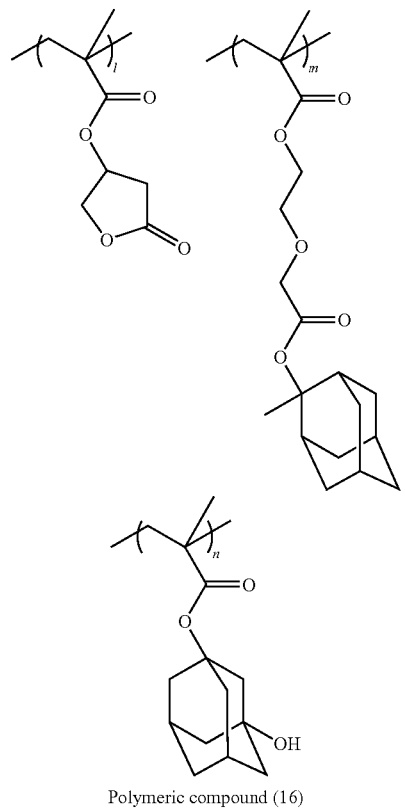

Polymeric compound (16)

Examples 20 to 33

The components shown in Table 3 were mixed together and dissolved to obtain positive resist compositions.

TABLE 3

|  | Component (A) | Component (B) | Component (D) | Component (S) | | PAB (° C.) | PEB (° C.) | Sensitivity (mJ/cm$^2$) | Circularity |
|---|---|---|---|---|---|---|---|---|---|
| Ex. 20 | (A)-3 [100] | (B)-1 [4.87] | — | (S)-1 [1200] | (S)-2 [800] | 90 | 90 | 12.9 | ⊚ |
| Ex. 21 | (A)-3 [100] | (B)-1 [4.87] | (D)-1 [0.10] | (S)-1 [1200] | (S)-2 [800] | 90 | 90 | 17 | ⊚ |
| Ex. 22 | (A)-3 [100] | (B)-1 [4.87] | (D)-2 [0.05] | (S)-1 [1200] | (S)-2 [800] | 90 | 90 | 15.1 | ⊚ |
| Ex. 23 | (A)-3 [100] | (B)-1 [4.87] | (D)-2 [0.50] | (S)-1 [1200] | (S)-2 [800] | 90 | 90 | 47 | ⊚ |
| Ex. 24 | (A)-3 [100] | (B)-2 [4.50] | — | (S)-1 [1200] | (S)-2 [800] | 90 | 90 | 4.5 | ⊚ |
| Ex. 25 | (A)-3 [100] | (B)-2 [4.50] | (D)-1 [0.10] | (S)-1 [1200] | (S)-2 [800] | 90 | 90 | 10.5 | ○ |
| Ex. 26 | (A)-3 [100] | (B)-2 [4.50] | (D)-2 [0.05] | (S)-1 [1200] | (S)-2 [800] | 90 | 90 | 9 | ○ |
| Ex. 27 | (A)-3 [100] | (B)-2 [4.50] | (D)-2 [0.50] | (S)-1 [1200] | (S)-2 [800] | 90 | 90 | 35.5 | ○ |
| Ex. 28 | (A)-3 [100] | (B)-3 [4.79] | — | (S)-1 [1200] | (S)-2 [800] | 90 | 90 | 15 | ⊚ |

TABLE 3-continued

| | Component (A) | Component (B) | Component (D) | Component (S) | | PAB (° C.) | PEB (° C.) | Sensitivity (mJ/cm²) | Circularity |
|---|---|---|---|---|---|---|---|---|---|
| Ex. 29 | (A)-3 [100] | (B)-3 [4.79] | (D)-1 [0.10] | (S)-1 [1200] | (S)-2 [800] | 90 | 90 | 20 | ⊚ |
| Ex. 30 | (A)-3 [100] | (B)-3 [4.79] | (D)-2 [0.05] | (S)-1 [1200] | (S)-2 [800] | 90 | 90 | 37 | ⊚ |
| Ex. 31 | (A)-3 [100] | (B)-3 [4.79] | (D)-2 [0.50] | (S)-1 [1200] | (S)-2 [800] | 90 | 90 | 46 | ⊚ |
| Ex. 32 | (A)-3 [100] | (B)-1 [4.87] | (D)-3 [0.12] | (S)-1 [1200] | (S)-2 [800] | 100 | 100 | 9.5 | ○ |
| Ex. 33 | (A)-3 [100] | (B)-1 [4.87] | (D)-4 [0.18] | (S)-1 [1200] | (S)-2 [800] | 100 | 100 | 9 | ⊚ |

In Table 3, the values in brackets [ ] indicate the amount (in terms of parts by weight) of the component added. Further, the reference characters indicate the following.

(A)-3: polymeric compound (4)
(B)-1: an acid generator represented by chemical formula (B)-1 above
(B)-2: an acid generator represented by chemical formula (B)-2 shown below
(B)-3: an acid generator represented by chemical formula (B)-3 shown below
(D)-1: tri-n-pentylamine
(D)-2: diethanolamine
(D)-3: tris(2-methoxymethoxyethyl)amine
(D)-4: tris{2-(2-methoxyethoxymethoxy)ethyl}amine
(S)-1: PGMEA
(S)-2: PGME

[Chemical Formula 75]

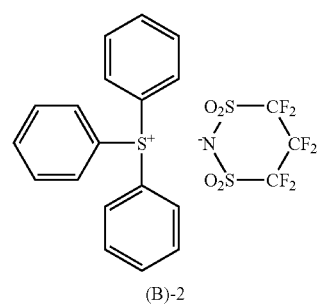

(B)-2

[Chemical Formula 76]

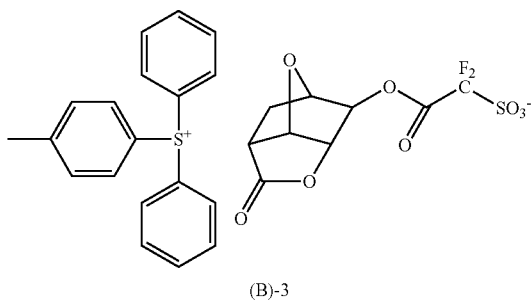

(B)-3

Using the obtained positive resist compositions, resist patterns were formed in the following manner, and lithography properties were evaluated.

[Resolution·sensitivity]

An organic anti-reflection film composition (product name: ARC29A, manufactured by Brewer Science Ltd.) was applied onto an 8-inch silicon wafer using a spinner, and the composition was then baked at 205° C. for 60 seconds, thereby forming an organic anti-reflection film having a film thickness of 77 nm. Then, a positive resist composition obtained above was applied onto the anti-reflection film using a spinner, and was then prebaked (PAB) on a hotplate at a temperature indicated in Table 3 for 60 seconds and dried, thereby forming a resist film having a film thickness of 120 nm.

Subsequently, the resist film was selectively irradiated with an ArF excimer laser (193 nm) through a mask pattern (6% halftone), using an ArF exposure apparatus NSR-S302 (manufactured by Nikon Corporation, NA (numerical aperture)=0.60, ⅔ annular illumination). Thereafter, a post exposure bake (PEB) treatment was conducted at a temperature indicated in Table 3 for 60 seconds, followed by development for 30 seconds at 23° C. in a 2.38% by weight aqueous solution of tetramethylammonium hydroxide. Then, the resist was washed for 30 seconds with pure water, followed by drying by shaking, thereby forming a resist pattern.

As a result, in each of the examples, a contact hole pattern with a hole diameter of 140 nm and a pitch of 280 nm was formed. The optimum exposure dose (Eop, mJ/cm²) with which the contact hole pattern was formed, i.e., sensitivity, was determined. The results are shown in Table 3.

[Circularity]

Each of the C/H patterns with a hole diameter of 140 nm and a pitch of 280 nm formed was observed from the upper side thereof using a scanning electron microscope, and the circularity was evaluated with the following criteria. The results are shown in Table 3.

⊚: extremely high circularity (no unevenness was observed at the circumferential portions of the hole pattern when the hole pattern was observed from the upper side thereof, and the shape of the pattern was excellent)

○: high circularity (although slight unevenness was observed at the circumferential portions of the hole pattern when the hole pattern was observed from the upper side thereof, the pattern as a whole had a high level of circularity)

Examples 34 to 36

The components shown in Table 4 were mixed together and dissolved to obtain positive resist compositions.

TABLE 4

|  | Component (A) | Component (B) | Component (D) | Component (S) | | Sensitivity (mJ/cm$^2$) | Circularity |
|---|---|---|---|---|---|---|---|
| Ex. 34 | (A)-4 [100] | (B)-3 [7.50] | (D)-5 [0.50] | (S)-1 [1200] | (S)-2 [800] | 30.4 | ○ |
| Ex. 35 | (A)-5 [100] | (B)-3 [7.50] | (D)-5 [0.50] | (S)-1 [1200] | (S)-2 [800] | 18.5 | ○ |
| Ex. 36 | (A)-6 [100] | (B)-3 [7.50] | (D)-5 [0.50] | (S)-1 [1200] | (S)-2 [800] | 33.5 | ⊙ |

In Table 4, the values in brackets [ ] indicate the amount (in terms of parts by weight) of the component added. Further, the reference characters indicate the following.

(A)-4: polymeric compound (6)
(A)-5: polymeric compound (7)
(A)-6: polymeric compound (8)
(B)-3: an acid generator represented by chemical formula (B)-3 above
(D)-5: stearyldiethanolamine
(S)-1: PGMEA
(S)-2: PGME Using the obtained positive resist compositions, resist patterns were formed in the following manner, and the lithography properties were evaluated.

[Resolution-sensitivity]

An organic anti-reflection film composition (product name; ARC29A, manufactured by Brewer Science Ltd.) was applied onto an 8-inch silicon wafer using a spinner, and the composition was then baked at 205° C. for 60 seconds, thereby forming an organic anti-reflection film having a film thickness of 89 nm. Then, a positive resist composition obtained above was applied onto the anti-reflection film using a spinner, and was then prebaked (PAB) on a hotplate at 90° C. for 60 seconds and dried, thereby forming a resist film having a film thickness of 120 nm.

Subsequently, a coating solution for forming a protection film (product name: TSRC-002; manufactured by Tokyo Ohka Kogyo Co., Ltd.) was applied onto the resist film using a spinner, and then heated at 90° C. for 60 seconds, thereby forming a top coat with a film thickness of 28 nm.

Thereafter, using an ArF exposure apparatus for immersion lithography (product name; NSR-S609B, manufactured by Nikon Corporation, NA (numerical aperture)=1.07, ⅔ annular illumination, reduction ratio: 1/4, immersion medium: water), the resist film having a top coat formed thereon was selectively irradiated with an ArF excimer laser (193 nm) through a mask pattern (6% halftone).

Next, the top coat was removed using a protection-film removing solution (product name: TS-Rememover-S; manufactured by Tokyo Ohka Kogyo Co., Ltd.). Then, a post exposure bake (PEB) treatment was conducted at 90° C. for 60 seconds, followed by development for 30 seconds at 23° C. in a 2.38% by weight aqueous solution of tetramethylammonium hydroxide (product name; NMD-W; manufactured by Tokyo Ohka Kogyo Co., Ltd.). Then, the resist film was rinsed for 25 seconds with pure water, followed by drying by shaking.

As a result, in each of the examples, a contact hole pattern with a hole diameter of 70 nm and a pitch of 150 nm was formed. The optimum exposure dose (Eop, mJ/cm$^2$) with which the contact hole pattern was formed, i.e., sensitivity, was determined. The results are shown in Table 4.

[Circularity]

Each of the C/H patterns with a hole diameter of 70 nm and a pitch of 150 nm formed was observed from the upper side thereof using a scanning electron microscope, and the circularity was evaluated with the following criteria. The results are shown in Table 4.

⊙: extremely high circularity (no unevenness was observed at the circumferential portions of the hole pattern when the hole pattern was observed from the upper side thereof, and the shape of the pattern was excellent)

○: high circularity (although slight unevenness was observed at the circumferential portions of the hole pattern when the hole pattern was observed from the upper side thereof, the pattern as a whole had a high level of circularity)

The invention claimed is:

1. A positive resist composition comprising a base component (A) which exhibits increased solubility in an alkali developing solution under action of acid and an acid-generator component (B) which generates acid upon exposure, said base component (A) comprising a polymeric compound (A1) having a structural unit (a0) represented by general formula (a0-1) shown below:

[Chemical Formula 1]

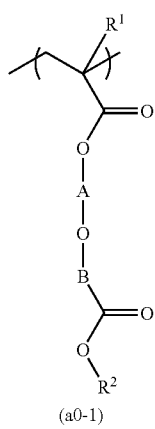

(a0-1)

wherein $R^1$ represents a hydrogen atom, a lower alkyl group or a halogenated lower alkyl group; A represents a divalent hydrocarbon group of 2 or more carbon atoms which may have a substituent; B represents a divalent hydrocarbon group of 1 or more carbon atoms which may have a substituent; and $R^2$ represents an acid dissociable, dissolution inhibiting group.

2. The positive resist composition according to claim 1, wherein said polymeric compound (A1) further has a structural unit (a2) derived from an acrylate ester containing a lactone-containing cyclic group. 3. The positive resist composition according to claim 1, wherein said polymeric compound (A1) further has a structural unit (a3) derived from an acrylate ester containing a polar group-containing aliphatic hydrocarbon group.

4. The positive resist composition according to claim 1, which further comprises a nitrogen-containing organic compound (D).

5. A method of forming a resist pattern, comprising: applying a positive resist composition of any one of claims 1 to 4 to a substrate to form a resist film on the substrate; conducting exposure of said resist film; and alkali-developing said resist film to form a resist pattern.

6. A polymeric compound having a structural unit (a0) represented by general formula (a0-1) shown below:

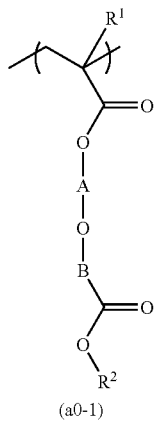

(a0-1)

[Chemical Formula 2]

wherein $R^1$ represents a hydrogen atom, a lower alkyl group or a halogenated lower alkyl group; A represents a divalent hydrocarbon group of 2 or more carbon atoms which may have a substituent; B represents a divalent hydrocarbon group of 1 or more carbon atoms which may have a substituent; and $R^2$ represents an acid dissociable, dissolution inhibiting group.

7. The polymeric compound according to claim 6, which further has a structural unit (a2) derived from an acrylate ester containing a lactone-containing cyclic group.

8. The polymeric compound according to claim 6 or 7, which further has a structural unit (a3) derived from an acrylate ester containing a polar group-containing aliphatic hydrocarbon group.

\* \* \* \* \*

UNITED STATES PATENT AND TRADEMARK OFFICE
CERTIFICATE OF CORRECTION

PATENT NO. : 7,604,920 B2
APPLICATION NO. : 12/186233
DATED : October 20, 2009
INVENTOR(S) : Shiono et al.

It is certified that error appears in the above-identified patent and that said Letters Patent is hereby corrected as shown below:

Column 2, Line 16, after "2003-241385" insert --.--.

Column 8, Line 35, change "Further" to --Further,--.

Column 9, Line 59, change "a" to --and--.

Column 13, Line 18, change "Next" to --Next,--.

Column 14, Line 43, change "solvent" to --solvent,--.

Column 15, Line 7, before "absorption" insert --infrared--.

Column 15, Line 29 (Approx.), change ""Step 1"" to --"Step 1"--.

Column 16, Line 11, change "above," to --above.--.

Column 28, Line 6, change "norbonyl" to --norbornyl--.

Column 28, Line 10, change "2-norbonyl" to --2-norbornyl--.

Column 28, Line 10, change "3-norbonyl" to --3 norbornyl--.

Column 28, Line 14, change "norbonyl" to --norbornyl--.

Column 28, Line 36, change "with" to --within--.

Column 57, Line 2, change "20" to --10--.

Column 58, Line 6, change "weight," to --weight.--.

Column 58, Line 39, change "pattern" to --pattern,--.

Column 61, Line 21, change "with" to --within--.

Column 61, Line 29, change "aryl" to --alkyl--.

Column 61, Line 30, change "Examples" to --examples--.

Column 61, Line 64, change "butynyl" to --butenyl--.

Column 62, Line 12, change "2-hydoxypropyl" to --2-hydroxypropyl--.

Column 62, Line 13, change "3-dihdroxypropyl" to --3-dihydroxypropyl--.

Column 65, Line 20, before "represents" insert --$n_6$--.

Column 66, Line 23, change "mean" to --means--.

Column 69, Line 46, change "substituent" to --substituent,--.

Column 70, Line 17, change "tri-n-decanylamine," to --tri-n-decylamine,--.

Column 72, Line 4, change "solvent" to --solvent,--.

Column 73, Line 21, change "an" to --and--.

Column 90, Line 53, change "treated" to --heated--.

Column 100, Line 62, after ")" insert --.--.

Column 101, Line 47(Approx.), change "name;" to --name:--.

Column 103, Lines 11-18, in Claim 2, "The positive resist composition according to claim 1, wherein said polymeric compound (A1) further has a structural unit (a2) derived from an acrylate ester containing a lactone-containing cyclic group. 3. The positive resist composition according to claim 1, wherein said polymeric compound (A1) further has a structural unit (a3) derived from an acrylate ester containing a polar group-containing aliphatic hydrocarbon group."

CERTIFICATE OF CORRECTION (continued)
U.S. Pat. No. 7,604,920 B2 should read --2. The positive resist composition according to claim 1, wherein said polymeric compound (A1) further has a structural unit (a2) derived from an acrylate ester containing a lactone-containing cyclic group.

3. The positive resist composition according to claim 1, wherein said polymeric compound (A1) further has a structural unit (a3) derived from an acrylate ester containing a polar group-containing aliphatic hydrocarbon group.--.

Signed and Sealed this

Thirtieth Day of March, 2010

David J. Kappos
*Director of the United States Patent and Trademark Office*